(12) United States Patent
Assmann et al.

(10) Patent No.: US 9,434,957 B2
(45) Date of Patent: Sep. 6, 2016

(54) METHODS OF IMPROVING DROUGHT TOLERANCE AND SEED PRODUCTION IN RICE

(71) Applicant: The Penn State Research Foundation, University Park, PA (US)

(72) Inventors: Sarah Assmann, State College, PA (US); Angel Ferrero-Serrano, State College, PA (US); David Chakravorty, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 336 days.

(21) Appl. No.: 13/866,401

(22) Filed: Apr. 19, 2013

(65) Prior Publication Data

US 2014/0007266 A1    Jan. 2, 2014

Related U.S. Application Data

(60) Provisional application No. 61/665,385, filed on Jun. 28, 2012.

(51) Int. Cl.
| | |
|---|---|
| *C12N 15/82* | (2006.01) |
| *C12N 9/14* | (2006.01) |
| *C07K 14/415* | (2006.01) |
| *C12N 9/16* | (2006.01) |

(52) U.S. Cl.
CPC .......... *C12N 15/8273* (2013.01); *C07K 14/415* (2013.01); *C12N 9/14* (2013.01); *C12N 9/16* (2013.01); *C12N 15/8261* (2013.01)

(58) Field of Classification Search
None
See application file for complete search history.

(56) References Cited

U.S. PATENT DOCUMENTS 6,501,007 B1 * 12/2002 Ashikari et al. .............. 800/290

OTHER PUBLICATIONS

Perfus-Barbeoch et al., 2004, Current Opinion in Plant Biology 7: 719-731.*
Nilson et al., 2009, New Phytologist 185: 734-746.*
Ashikari et al., 1999, Proc. Natl. Acad. Sci. USA 96: 10284-10289.*
Harb et al., 2010, Plant Physiology 154: 1254-1271.*
Nilson, Sarah E., et al., "Heterotrimeric G Proteins Regulate Reproductive Trait Plasticity in Response to Water Availability", New Phytologist (2009), pp. 1-13.
Hu, H., et al. "P13 CO2 Regulation of Stomatal Development by Carbonic Anhydrases", Division of Biological Sciences, Cell and Developmental Biology Section, University of California, Jun. 1, 2012, p. 42.
Perfus-Barbeoch, Laetitia, et al., "Plant Heterotrimeric G Protein Function: Insights From Arabidopsis and Rice Mutants", Science Direct, Current Opinion in Plant Biology, 2004, 7, pp. 719-731.

* cited by examiner

Primary Examiner — David T Fox
Assistant Examiner — Bratislav Stankovic
(74) Attorney, Agent, or Firm — McKee, Voorhees & Sease, PLC

(57) ABSTRACT

The invention provides for compositions and methods for producing plants that have higher yield in drought conditions by manipulating the G-proteins such as the rice alpha subunit gene, RGA1. In particular, the present invention provides for plants, varieties, lines, and hybrids, as well as plant tissues and plant seeds that contain modified G-protein activity, particularly RGA1 activity to engineer drought tolerance and improved seed production in plants, as well as improved tolerance to high density planting

9 Claims, 18 Drawing Sheets
(8 of 18 Drawing Sheet(s) Filed in Color)

WT Well-Watered
WT Medium-Water
WT Low Water d1 Well-Watered
d1 Medium-Water
d1 Low Water

*Estimated grain yield =
number of panicles per plant \*average number of filled seeds per panicle \*average seed weight*

Alignment:

```
Genbank    ATGGGCTCATCCTGTAGCAGATCTCATTCTTTAAGTGAGGCTGAAACAACCAAAAATGCA 60
d1         ATGGGCTCATCCTGTAGCAGATCTCATTCTTTAAGTGAGGCTGAAACAACCAAAAATGCA 60
           ************************************************************

Genbank    AAATCTGCAGACATTGACAGGCGAATTTTGCAAGAGACAAAAGCAGAGCAACACATCCAC 120
d1         AAATCTGCAGACATTGACAGGCGAATTTTGCAAGAGACAAAAGCAGAGCAACACATCCAC 120
           ************************************************************

Genbank    AAGCTCTTACTTCTTGGTGCGGGAGAATCAGGGAAGTCTACGATATTTAAACAGATTAAG 180
d1         AAGCTCTTACTTCTTGGTGCGGGAGAATCAGGGAAGTCTACGATATTTAAACAGATTAAG 180
           ************************************************************

Genbank    CTCCTTTTCCAAACTGGCTTTGATGAGGCAGAACTTAGGAGCTACACATCAGTTATCCAT 240
d1         CTCCTTTTCCAAACTGGCTTTGATGAGGCAGAACTTAGGAGCTACACATCAGTTATCCAT 240
           ************************************************************

Genbank    GCAAACGTCTATCAGACAATTAAAATACTATATGAAGGAGCAAAAGAACTCTCACAAGTG 300
d1         GCAAACGTCTATCAGACAATTAAAATACTATATGAAGGAGCAAAAGAACTCTCACAAGTG 300
           ************************************************************

Genbank    GAATCAGATTCCTCAAAGTATGTTATATCCCCAGATAACCAGGAAATTGGAGAAAAACTA 360
d1         GAATCAGATTCCTCAAAGTATGTTATATCCCCAGATAACCAGGAAATTGGAGAAAAACTA 360
           ************************************************************

Genbank    TCAGATATTGATGGCAGGTTGGATTATCCACTGCTGAACAAAGAACTTGTACTCGATGTA 420
d1         TCAGATATTGATGGCAGGTTGGATTATCCACTGCTGAACAAAGAACTTGTACTCGATGTA 420
           ************************************************************

Genbank    AAAAGGTTATGGCAAGACCCAGCCATTCAGGAAACTTACTTACGTGGAAGTATTCTGCAA 480
```

FIG. 12A

```
d1        AAAAGGTTATGGCAAGACCCAGCCATTCAGGAAACTTACTTACGTGGAAGTATTCTGCAA 480
          ************************************************************

Genbank   CTTCCTGATTGTGCACAATACTTCATGGAAAATTTGGATCGATTAGCTGAAGCAGGTTAT 540
d1        CTTCCTGATTGTGCACAATACTTCATGGAAAATTTGGATCGATTAGCTGAAGCAGGTTAT 540
          ************************************************************

Genbank   GTGCCAACAAAGGAGGATGTGCTTTATGCAAGAGTACGGACAAATGGTGTTGTACAAATA 600
d1        GTGCCAACAAAGGAGGATGTGCTTTATGCAAGAGTACGGACAAATGGTGTTGTACAAATA 600
          ************************************************************

Genbank   CAATTTAGTCCTGTTGGAGAAAACAAAAGAGGTGGAGAGGTATATAGGTTGTATGATGTA 660
d1        CAATTTAGTCCTGTTGGAGAAAACAAAAGAGGTGGAGAGGTATATAGGTTGTATGATGTA 660
          ************************************************************

Genbank   GGAGGCCAGAGGAATGAGAGGAGAAAGTGGATTCATCTTTTTGAAGGTGTTAATGCGGTA 720
d1        GGAGGCCAGAGGAATGAGAGGAGAAAGTGGATTCATCTTTTTGAAGGTGTTAATGCGGTA 720
          ************************************************************

Genbank   ATCTTTTGTGCTGCCATTAGCGAATATGATCAGATGCTATTTGAAGATGAGACAAAAAAC 780
d1        ATCTTTTGTGCTGCCATTAGCGAATATGATCAGATGCTATTTGAAGATGAGACAAAAAAC 780
          ************************************************************

Genbank   AGAATGATGGAGACCAAGGAACTCTTTGACTGGGTTTTAAAGCAAAGATGTTTTGAGAAA 840
d1        AGAATGATGGAGACCAAGGAACTCTTTGACTGGGTTTTAAAGCAAAGATGTTTTGAGAAA 840
          ************************************************************

Genbank   ACATCATTCATTCTGTTTCTCAACAAATTTGATATATTCGAGAAGAAAATACAAAAGGTT 900
d1        ACATCATTCATTCTGTTTCTCAACAAATTTGATATATTCGAGAAGAAAATACAAAAGGTT 900
          ************************************************************

Genbank   CCTTTAAGTGTG  CGAGTGGTTTAAAGACTACCAGCCTATTGCACCTGGGAAACAGGAG 960
d1        CCTTTAAGTGTG  CGAGTGGTTTAAAGACTACCAGCCTATTGCACCTGGGAAACAGGAG 958
          ************  **********************************************

Genbank   GTTGAACATGCATATGAGTTTGTCAAGAAGAAGTTTGAAGAGCTCTACTTCCAGAGCAGC 1020
d1        GTTGAACATGCATATGAGTTTGTCAAGAAGAAGTTTGAAGAGCTCTACTTCCAGAGCAGC 1018
          ************************************************************

Genbank   AAGCCTGACCGTGTGGACCGCGTCTTCAAAATCTACAGAACTACGGCCCTAGACCAGAAA 1080
d1        AAGCCTGACCGTGTGGACCGCGTCTTCAAAATCTACAGAACTACGGCCCTAGACCAGAAA 1078
          ************************************************************

Genbank   CTTGTAAAGAAGACATTCAAGTTGATTGATGAGAGCATGAGACGCTCCAGGGAAGGAACT 1140
d1        CTTGTAAAGAAGACATTCAAGTTGATTGATGAGAGCATGAGACGCTCCAGGGAAGGAACT 1138
          ************************************************************

Genbank   TGA 1143
d1        TGA 1141
          ***
```

*FIG. 12B*

Alignment:

```
Genbank   MGSSCSRSHSLSEAETTKNAKSADIDRRILQETKAEQHIHKLLLLGAGESGKSTIFKQIK 60
d1        MGSSCSRSHSLSEAETTKNAKSADIDRRILQETKAEQHIHKLLLLGAGESGKSTIFKQIK 60
          ************************************************************

Genbank   LLFQTGFDEAELRSYTSVIHANVYQTIKILYEGAKELSQVESDSSKYVISPDNQEIGEKL 120
d1        LLFQTGFDEAELRSYTSVIHANVYQTIKILYEGAKELSQVESDSSKYVISPDNQEIGEKL 120
          ************************************************************

Genbank   SDIDGRLDYPLLNKELVLDVKRLWQDPAIQETYLRGSILQLPDCAQYFMENLDRLAEAGY 180
d1        SDIDGRLDYPLLNKELVLDVKRLWQDPAIQETYLRGSILQLPDCAQYFMENLDRLAEAGY 180
          ************************************************************

Genbank   VPTKEDVLYARVRTNGVVQIQFSPVGENKRGGEVYRLYDVGGQRNERRKWIHLFEGVNAV 240
d1        VPTKEDVLYARVRTNGVVQIQFSPVGENKRGGEVYRLYDVGGQRNERRKWIHLFEGVNAV 240
          ************************************************************

Genbank   IFCAAISEYDQMLFEDETKNRMMETKELFDWVLKQRCFEKTSFILFLNKFDIFEKKIQKV 300
d1        IFCAAISEYDQMLFEDETKNRMMETKELFDWVLKQRCFEKTSFILFLNKFDIFEKKIQKV 300
          ************************************************************

Genbank   PLSV    KDYQPIAPGKQEVEHAYEFVKKKFEELYFQSSKPDRVDRVFKIYRTTALDQK 360
d1        PLSV    ------------------------------------------------------ 307
          ****

Genbank   LVKKTFKLIDESMRRSREGT 380
d1        --------------------
```

FIG. 13

Alignment:

```
MSU    ATGGGCTCATCCTGTAGCAGATCTCATTCTTTAAGTGAGGCTGAAACAACCAAAAATGCA 60
d1     ATGGGCTCATCCTGTAGCAGATCTCATTCTTTAAGTGAGGCTGAAACAACCAAAAATGCA 60
       ************************************************************

MSU    AAAGTAAGTTAGCACTCGGACTTATTGAACAAGTAAATGCTAACTCAATTCTTGATTTCA 120
d1     AAAGTAAGTTAGCACTCGGACTTATTGAACAAGTAAATGCTAACTCAATTCTTGATTTCA 120
       ************************************************************

MSU    GAGTTGCCACATTTGGTTTCTTCTAATTCAGCTGGTAACAGTCTGCAGACATTGACAGGC 180
d1     GAGTTGCCACATTTGGTTTCTTCTAATTCAGCTGGTAACAGTCTGCAGACATTGACAGGC 180
       ************************************************************

MSU    GAATTTTGCAAGAGACAAAAGCAGAGCAACACATCCACAAGCTCTTACTTCTTGGTATTG 240
d1     GAATTTTGCAAGAGACAAAAGCAGAGCAACACATCCACAAGCTCTTACTTCTTGGTATTG 240
       ************************************************************

MSU    CTAACTTTCCCAAATTTAAGTGGTCATTTTCCTTGTCACAATTATCTGTGCTACCTTTAG 300
d1     CTAACTTTCCCAAATTTAAGTGGTCATTTTCCTTGTCACAATTATCTGTGCTACCTTTAG 300
       ************************************************************

MSU    TATCTATTGGTTCAGAAAATTAATTGTTTATGTTGTTCCTATTTACCTCTATAAAAAAAC 360
d1     TATCTATTGGTTCAGAAAATTAATTGTTTATGTTGTTCCTATTTACCTCTATAAAAAAAC 360
       ************************************************************

MSU    CTTTCTCATGTTATTTCCAAAAAAAAAGAAGATAAATAAATGTATCCTAGAAATTTTTAG 420
d1     CTTTCTCATGTTATTTCCAAAAAAAAAGAAGATAAATAAATGTATCCTAGAAATTTTTAG 420
       ************************************************************

MSU    TTTGAACTTGTTCTCAATGTGGATCCATCCTTCTTTCTCTCTCTCAATTGCTTCTGTTTT 480
d1     TTTGAACTTGTTCTCAATGTGGATCCATCCTTCTTTCTCTCTCTCAATTGCTTCTGTTTT 480
       ************************************************************

MSU    AAGGTGCGGGAGAATCAGGGAAGTCTACGATATTTAAACAGGTGATGAATGTTATATTCC 540
d1     AAGGTGCGGGAGAATCAGGGAAGTCTACGATATTTAAACAGGTGATGAATGTTATATTCC 540
       ************************************************************

MSU    ATGGAGAATCATAATCCGTACGCCGCTAGTTAGTCTGATGTATTCTTACTGTTCACCTGC 600
d1     ATGGAGAATCATAATCCGTACGCCGCTAGTTAGTCTGATGTATTCTTACTGTTCACCTGC 600
       ************************************************************

MSU    AGATTAAGCTCCTTTTCCAAACTGGCTTTGATGAGGCAGAACTTAGGAGCTACACATCAG 660
d1     AGATTAAGCTCCTTTTCCAAACTGGCTTTGATGAGGCAGAACTTAGGAGCTACACATCAG 660
       ************************************************************

MSU    TTATCCATGCAAACGTCTATCAGACAATTAAAGTATGCAATACTGGAAAGGGTGTGTCTT 720
d1     TTATCCATGCAAACGTCTATCAGACAATTAAAGTATGCAATACTGGAAAGGGTGTGTCTT 720
       ************************************************************

MSU    TTTTTTCTTATTGCAAAGTGGGGATTATGTAGGAGATTCGACTAGGGATTTGTATTCTGT 780
d1     TTTTTTCTTATTGCAAAGTGGGGATTATGTAGGAGATTCGACTAGGGATTTGTATTCTGT 780
       ************************************************************

MSU    TCATAAGGAAATGCGTTCATACTTTTCCTTTTTGTCGAGTAATGTGTTAAATGTTAACAG 840
d1     TCATAAGGAAATGCGTTCATACTTTTCCTTTTTGTCGAGTAATGTGTTAAATGTTAACAG 840
       ************************************************************

MSU    ATACTATATGAAGGAGCAAAAGAACTCTCACAAGTGGAATCAGATTCCTCAAAGTATGTT 900
d1     ATACTATATGAAGGAGCAAAAGAACTCTCACAAGTGGAATCAGATTCCTCAAAGTATGTT 900
       ************************************************************
```

*FIG. 14A*

```
MSU  ATATCCCCAGATAACCAGGTTTGTGCTTACTCTTTACTCAACAGTTAAAGCTAAATCTGT  960
d1   ATATCCCCAGATAACCAGGTTTGTGCTTACTCTTTACTCAACAGTTAAAGCTAAATCTGT  960
     ************************************************************

MSU  GCATATGAACATGTCTTGTTAAATCTGGGAATACAAACATTTTGATTTGCAACATTTCTG  1020
d1   GCATATGAACATGTCTTGTTAAATCTGGGAATACAAACATTTTGATTTGCAACATTTCTG  1020
     ************************************************************

MSU  TTGTAGTCAAGCTGCTCGGCTCTATGTTTTAACCTGTTAAGACCTTGTAGACTGTGCTCG  1080
d1   TTGTAGTCAAGCTGCTCGGCTCTATGTTTTAACCTGTTAAGACCTTGTAGACTGTGCTCG  1080
     ************************************************************

MSU  GCTCTATTGTAGTCTTATATTTTACACGGTCATTCTATAATGAAAACTTGAAAAGATAT  1140
d1   GCTCTATTGTAGTCTTATGTTTTACACGGTCATTCTATAATGAAAACTTGAAAAGATAT  1140
     ****************** *****************************************

MSU  CTATTGAACCGTACAATGTACTGAACAAAGTAGAAAAGAACAATGAGATTTTGTAACATT  1200
d1   CTATTGAACCGTACAATGTACTGAACAAAGTAGAAAAGAACAATGAGATTTTGTAACATT  1200
     ************************************************************

MSU  TATTCTTCCTTGTTTATTTGATTGCTTCAGACAATTGTTGATATGCTAAAAATAACTTGG  1260
d1   TATTCTTCCTTGTTTATTTGATTGCTTCAGACAATTGTTGATATGCTAAAAATAACTTGG  1260
     ************************************************************

MSU  TATCAAATGTGGGTGTTATAAGATTCAATTTTTTTCTCAACCAGGTTAAAAAAAGTATAC  1320
d1   TATCAAATGTGGGTGTTATAAGATTCAATTTTTTTCTCAACCAGGTTAAAAAAAGTATAC  1320
     ************************************************************

MSU  CTTTGTGCATTTACCTTGTTCCGTTGCTTTGGAACTTTAAAGGAAAACTGACTTTTCTTA  1380
d1   CTTTGTGCATTTACCTTGTTCCGTTGCTTTGGAACTTTAAAGGAAAACTGACTTTTCTTA  1380
     ************************************************************

MSU  GGCATTGAAAGACAAATATCACCAGTTTCACACTGTACACCTTACCAACCAATTTTGTTT  1440
d1   GGCATTGAAAGACAAATATCACCAGTTTCACACTGTACACCTTACCAACCAATTTTGTTT  1440
     ************************************************************

MSU  CTTAGATGTCATTTACTTTGTCATATCATCAGGAAATTGGAGAAAAACTATCAGATATTG  1500
d1   CTTAGATGTCATTTACTTTGTCATATCATCAGGAAATTGGAGAAAAACTATCAGATATTG  1500
     ************************************************************

MSU  ATGGCAGGTTGGATTATCCACTGCTGAACAAAGAACTTGTACTCGATGTAAAAGGTTAT  1560
d1   ATGGCAGGTTGGATTATCCACTGCTGAACAAAGAACTTGTACTCGATGTAAAAGGTTAT  1560
     ************************************************************

MSU  GGCAAGACCCAGCCATTCAGGTGAAAACAAATAGCCATTCAAATCTTTTGAAGTTATATA  1620
d1   GGCAAGACCCAGCCATTCAGGTGAAAACAAATAGCCATTCAAATCTTTTGAAGTTATATA  1620
     ************************************************************

MSU  GTTTTCCTGGCCAGGTGTGCTGAAGCAATGCTCTATACTGTAGGAAACTTACTTACGTGG  1680
d1   GTTTTCCTGGCCAGGTGTGCTGAAGCAATGCTCTATACTGTAGGAAACTTACTTACGTGG  1680
     ************************************************************

MSU  AAGTATTCTGCAACTTCCTGATTGTGCACAATACTTCATGGAAAATTTGGATCGATTAGC  1740
d1   AAGTATTCTGCAACTTCCTGATTGTGCACAATACTTCATGGAAAATTTGGATCGATTAGC  1740
     ************************************************************

MSU  TGAAGCAGGTTATGTGCCAACAAAGGTGTGCTGTCCATGTTCATAGACAATTATTTACAT  1800
d1   TGAAGCAGGTTATGTGCCAACAAAGGTGTGCTGTCCATGTTCATAGACAATTATTTACAT  1800
     ************************************************************

MSU  ATTCTCAGATATTTGTGCTGACACCATTTCATGTTGATTTTTAGTCTACTTAGTCAGAGG  1860
d1   ATTCTCAGATATTTGTGCTGACACCATTTCATGTTGATTTTTAGTCTACTTAGTCAGAGG  1860
     ************************************************************
```

MSU       TTGTCAAATGGTTAACTATGTGTACTGAGTCAGAGGTTGCCAAATAGTTTTAAAAGATGG 1920
d1        TTGTCAAATGGTTAACTATGTGTACTGAGTCAGAGGTTGCCAAATAGTTTTAAAAGATGG 1920
              ************************************************************

MSU       GCATATGTTTATCCTTATCTTTTAAATAATATTGGAGGCTATCCTTTAAAATTCAATATT 1980
d1        GCATATGTTTATCCTTATCTTTTAAATAATATTGGAGGCTATCCTTTAAAATTCAATATT 1980
              ************************************************************

MSU       AGGGAGGAGAAACTATTATTCTACCGTTATTACGCAGTCTACATAACGAAGGTAAAAAAT 2040
d1        AGGGAGGAGAAACTATTATTCTACCGTTATTACGCAGTCTACATAACGAAGGTAAAAAAT 2040
              ************************************************************

MSU       GTCCCTGTGAAACATAGGGTGCAAAACTGCTGTGAATAAAACTCTACTTATCTAAGCACC 2100
d1        GTCCCTGTGAAACATAGGGTGCAAAACTGCTGTGAATAAAACTCTACTTATCTAAGCACC 2100
              ************************************************************

MSU       TTGAGCTTTTGAGTTCCCACATATTAATCTTATGACACTAGCATATATTTTTTTTGTTCA 2160
d1        TTGAGCTTTTGAGTTCCCACATATTAATCTTATGACACTAGCATATATTTTTTTTGTTCA 2160
              ************************************************************

MSU       GTTCCTTCAATAAGTTGCAAACCACAAATATGATCACTGTACCATCCACTTTTGCAACCA 2220
d1        GTTCCTTCAATAAGTTGCAAACCACAAATATGATCACTGTACCATCCACTTTTGCAACCA 2220
              ************************************************************

MSU       TTTCCCGTCATTTCTTAAGCATAGAAAATTGTTTGTCACTTGTTTAAGTCCACACTGCAT 2280
d1        TTTCCCGTCATTTCTTAAGCATAGAAAATTGTTTGTCACTTGTTTAAGTCCACACTGCAT 2280
              ************************************************************

MSU       CAAAATTCCAATTAACATTGTGTGTGCTAAGTGAAGATATGACTCCATATTTCTGCATTT 2340
d1        CAAAATTCCAATTAACATTGTGTGTGCTAAGTGAAGATATGACTCCATATTTCTGCATTT 2340
              ************************************************************

MSU       AGCAGTCTGATGGATAATTTGTGATTGTACCTTGTCTAATGGTTCGTTTGAAAGGCTGGT 2400
d1        AGCAGTCTGATGGATAATTTGTGATTGTACCTTGTCTAATGGTTCGTTTGAAAGGCTGGT 2400
              ************************************************************

MSU       AGTTGATCTTCCATACTTAAGAATGCTTGCAGTATTATAGTTGTCAATATTATGAGTCAT 2460
d1        AGTTGATCTTCCATACTTAAGAATGCTTGCAGTATTATAGTTGTCAATATTATGAGTCAT 2460
              ************************************************************

MSU       TTTGCAGGAGGATGTGCTTTATGCAAGAGTACGGACAAATGGTGTTGTACAAATACAATT 2520
d1        TTTGCAGGAGGATGTGCTTTATGCAAGAGTACGGACAAATGGTGTTGTACAAATACAATT 2520
              ************************************************************

MSU       TAGGTAATCTGCTGACACTATTTTTTGCACATTTTTTGCTGGTTGCTCTACTATGTACA 2580
d1        TAGGTAATCTGCTGACACTATTTTTTGCACATTTTTTGCTGGTTGCTCTACTATGTACA 2580
              ************************************************************

MSU       GAACGACAAGTTGAAGTCCTTTTTTTCTCCCCTTTCACTTCTAAGATATGACCTGAGAGG 2640
d1        GAACGACAAGTTGAAGTCCTTTTTTTCTCCCCTTTCACTTCTAAGATATGACCTGAGAGG 2640
              ************************************************************

MSU       TTCTGAATGTAGCTGTTTTAACATGACTTGAATCATCTAGTTAACTCGGTTTCTTTCTGC 2700
d1        TTCTGAATGTAGCTGTTTTAAGATGAGTTGAATCATCTAGTTAACTGGGTTTCTTTCTGC 2700
              ********************  ***** ****************** *************

MSU       AGTCCTGTTGGAGAAAACAAAAGAGGTGGAGAGGTATATAGGTTGTATGATGTAGGAGGC 2760
d1        AGTCCTGTTGGAGAAAACAAAAGAGGTGGAGAGGTATATAGGTTGTATGATGTAGGAGGC 2760
              ************************************************************

MSU       CAGAGGAATGAGAGGAGAAAGTGGATTCATCTTTTTGAAGGTGTTAATGCGGTAATCTTT 2820
```

*FIG. 14C*

| | | |
|---|---|---|
| d1 | CAGAGGAATGAGAGGAGAAAGTGGATTCATCTTTTTGAAGGTGTTAATGCGGTAATCTTT | 2820 |
| | ************************************************************ | |
| MSU | TGTGCTGCCATTAGCGAGTAAGTACAATTTTTTTGATTGTTGAACTTATCCTAATCTGCT | 2880 |
| d1 | TGTGCTGCCATTAGCGAGTAAGTACAATTTTTTTGATTGTTGAACTTATCCTAATCTGCT | 2880 |
| | ************************************************************ | |
| MSU | AAGTTCTTCTCATAGGCTTCTTGTTCATTTCAGATATGATCAGATGCTATTTGAAGATGA | 2940 |
| d1 | AAGTTCTTCTCATAGGCTTCTTGTTCATTTCAGATATGATCAGATGCTATTTGAAGATGA | 2940 |
| | ************************************************************ | |
| MSU | GACAAAAAACAGAATGATGGAGACCAAGGAACTCTTTGACTGGGTTTTAAAGCAAAGATG | 3000 |
| d1 | GACAAAAAACAGAATGATGGAGACCAAGGAACTCTTTGACTGGGTTTTAAAGCAAAGATG | 3000 |
| | ************************************************************ | |
| MSU | TTTTGAGGTCTGCATGCATCCATCTCTGCAACCTTTGTGCTCATGCTTTTTTTCTCATTT | 3060 |
| d1 | TTTTGAGGTCTGCATGCATCCATCTCTGCAACCTTTGTGCTCATGCTTTTTTTCTCATTT | 3060 |
| | ************************************************************ | |
| MSU | TGAAACTAATTACGGTGCTATATTGACCATCAGAAAACATCATTCATTCTGTTTCTCAAC | 3120 |
| d1 | TGAAACTAATTACGGTGCTATATTGACCATCAGAAAACATCATTCATTCTGTTTCTCAAC | 3120 |
| | ************************************************************ | |
| MSU | AAATTTGATATATTCGAGAAGAAAATACAAAAGGTAAGGCCTGCTCTTTGTACCAATGCA | 3180 |
| d1 | AAATTTGATATATTCGAGAAGAAAATACAAAAGGTAAGGCCTGCTCTTTGTACCAATGCA | 3180 |
| | ************************************************************ | |
| MSU | TAGTTTAGTACTAAATGTTACCAACATTTATGTTTACGCTGGTTACGTAGGTTCCTTTAA | 3240 |
| d1 | TAGTTTAGTACTAAATGTTACCAACATTTATGTTTACGCTGGTTACGTAGGTTCCTTTAA | 3240 |
| | ************************************************************ | |
| MSU | GTGT▓▓GCGAGTGGTTTAAAGACTACCAGCCTATTGCACCTGGGAAACAGGAGGTTGAAC | 3300 |
| d1 | GTGT▓GCGAGTGGTTTAAAGACTACCAGCCTATTGCACCTGGGAAACAGGAGGTTGAAC | 3298 |
| | ****  ****************************************************** | |
| MSU | ATGCATATGAGTGAGTGCACTACTCGCCCTCTCAGATGAACATGGGCATTTGGCCATTTG | 3360 |
| d1 | ATGCATATGAGTGAGTGCACTACTCGCCCTCTCAGATGAACATGGGCATTTGGCCATTTG | 3358 |
| | ************************************************************ | |
| MSU | TAATGTTGCTGCATGGTGCACTTATATGCCTTGATAAGTTTTTCCATTCTAATGTTATAT | 3420 |
| d1 | TAATGTTGCTGCATGGTGCACTTATATGCCTTGATAAGTTTTTCCATTCTAATGTTATAT | 3418 |
| | ************************************************************ | |
| MSU | AGTATCAAACGTTCATCATTACTGTGGCTTATGGTCTGGAGTGACGTTTTACAGGTTTGT | 3480 |
| d1 | AGTATCAAACGTTCATCATTACTGTGGCTTATGGTCTGGAGTGACGTTTTACAGGTTTGT | 3478 |
| | ************************************************************ | |
| MSU | CAAGAAGAAGTTTGAAGAGCTCTACTTCCAGAGCAGCAAGCCTGACCGTGTGGACCGCGT | 3540 |
| d1 | CAAGAAGAAGTTTGAAGAGCTCTACTTCCAGAGCAGCAAGCCTGACCGTGTGGACCGCGT | 3538 |
| | ************************************************************ | |
| MSU | CTTCAAAATCTACAGAACTACGGCCCTAGACCAGAAACTTGTAAAGAAGACATTCAAGTT | 3600 |
| d1 | CTTCAAAATCTACAGAACTACGGCCCTAGACCAGAAACTTGTAAAGAAGACATTCAAGTT | 3598 |
| | ************************************************************ | |
| MSU | GATTGATGAGAGCATGAGACGCTCCAGGGAAGGAACTTGA | 3640 |
| d1 | GATTGATGAGAGCATGAGACGCTCCAGGGAAGGAACTTGA | 3638 |
| | **************************************** | |

FIG. 14D

METHODS OF IMPROVING DROUGHT TOLERANCE AND SEED PRODUCTION IN RICE

CROSS-REFERENCE TO RELATED APPLICATIONS

This application claims priority under 35 U.S.C. §119 to provisional application Ser. No. 61/665,385 filed Jun. 28, 2012, herein incorporated by reference in its entirety.

BACKGROUND OF THE INVENTION

Rice is one of the three major cereal crops and is a staple food for more than a third of the world's population. Drought is one of the major abiotic stress factors limiting crop productivity worldwide. Global climate changes may further exacerbate the drought situation in major crop-producing countries. Although irrigation may in theory solve the drought problem, it is usually not a viable option because of the cost associated with building and maintaining an effective irrigation system, as well as other issues, such as the general availability of water. Thus, alternative means for alleviating plant water stress are needed.

Upon exposure of plants to drought conditions, many stress-related genes are induced and their products are thought to function as cellular protectants of stress-induced damage. The expression of stress-related genes is largely regulated by specific transcription factors. Members of the AP2, bZIP, zinc finger, and MYB families have been shown to have regulatory roles in stress responses. The rice and Arabidopsis genomes code for more than 1300 transcriptional regulators, accounting for about 6% of the estimated total number of genes in both cases. About 45% of these transcription factors were reported to be from plant-specific families (Riechmann et al., (2000) Science 290: 2105-2110).

Plant modification for enhanced drought tolerance is mostly based on the manipulation of either transcription and/or signaling factors or genes that directly protect plant cells against water deficit. Despite much progress in the field, understanding the basic biochemical and molecular mechanisms for drought stress perception, transduction, response and tolerance remains a major challenge. Utilization of the knowledge on drought tolerance to generate plants that can endure under extreme water deficit condition is even a bigger challenge.

Rice is a staple food for greater than one third of the world's population and worldwide total rice planting area is approximately 1.5 million square kilometers. In 2009 global rice production was over 670 million tons, second only to maize.

Approximately 20% of rice growing areas worldwide are prone to drought. Drought is a particularly important issue for rice production. About 5000 liters of water are needed to produce one kilogram of rice, approximately double the needs of other crops.

Despite efforts to develop drought-tolerant rice plants, very few attempts have been shown to improve grain yields. Examples of positive effects include transgenic rice plants expressing SNAC1 (Hu et al., (2006) Proc Natl Acad Sci USA 103: 12987-12992) and OsLEA3 (Xiao at al., (2007) Theor Appl Genet 115: 35-46), which was shown to improve grain yield under field drought conditions.

Heterotrimeric G-proteins are key signal transduction components that couple the perception of an external signal by a G-protein coupled receptor (GPCR) to downstream effectors. More than one third of mammalian signaling pathways depend on heterotrimeric G-proteins, including vision, taste, olfaction, hormones, and neurotransmitters. G-protein coupled signaling pathways are targets of approximately half of all pharmaceuticals.

The G-protein complex is comprised of Gα, Gβ and Gγ monomeric subunits that assemble as a heterotrimer that physically associates with a GPCR. Activation of the GPCR triggers the Gα subunit to exchange GDP for GTP, thus activating the G-protein. Once active the heterotrimeric complex dissociates from the GPCR and the Gα subunit separates from the Gβγ heterodimer. Both GTP-bound Gα and the Gβγ heterodimer transduce the signal to downstream effectors.

Heterotrimeric G-proteins have been studied extensively in animals. To date, 23 Gα, 6 Gβ and 11 Gγ genes have been reported in mammals (Vanderbeld and Kelly (2000) Biochem. Cell Biol. 78: 537-550). The alpha subunits are classified into four subfamilies: Gs, Gi, Gq, and $G_{12}$. In contrast, relatively little is known about the role G-proteins play in plants. Loss-of-function mutants in the Gα subunit of rice and Arabidopsis are completely viable, but show several characteristic developmental attributes. The rice mutant exhibits shortened internodes, rounded seeds, and partial insensitivity to gibberellin, whereas the Arabidopsis mutants have rounded leaves and altered sensitivity to a number of phytohormones (Ashikari et al. (1999) Proc. Natl. Acad. Sci. 96: 10284-10289; Fujisawa et al. (1999) Proc. Natl. Acad. Sci. 96:7575-7580; Ueguchi-Tanaka et al. (2000) Proc. Natl. Acad. Sci. 97: 11638-11643; Wang et al. (2001) Science 292: 2070-2072; (Ullah et al. (2001) Science 292: 2066-2069). A loss-of-function mutant in the Gβ subunit of Arabidopsis (AGB1) exhibits several defects including short, blunt fruits, rounded leaves, and shortened floral buds (Lease et al. (2001) Plant Cell 13: 2631-2641).

It can be seen that there is a continuing need to develop drought tolerance in plants, particularly rice.

It is an object of the present invention to modulate Gα proteins such as RGA1, in plants to engineer drought tolerance and increase seed yield under such conditions.

Other objects will become apparent from the description of the invention, which follows.

SUMMARY OF THE INVENTION

The rice dwarf mutant, d1, contains a non-functional RGA1 gene, encoding the GTP-binding α-subunit of the heterotrimeric G protein. Rice RGA1 encodes a 380 amino acid Gα protein. Applicants have identified a 2 bp deletion (allele d1), which results in a frameshift mutation resulting in a predicted protein truncation after amino acid 304. This mutant was originally isolated as a spontaneous mutant with reduced height and shorter, erect, thicker, broad, dark green leaves, compact panicles, and short, round grains. Applicants have identified that a non-functional RGA1 gene or other related G-proteins can be used to create higher seed production and yield under drought conditions. The d1 plants also perform better at higher planting density.

Thus the present invention provides for compositions and methods for producing plants that have higher yield in drought conditions by manipulating the G-proteins such as the RGA1 gene. In particular, the present invention provides for plants, varieties, lines, and hybrids, as well as plant tissues and plant seeds that contain modified G-protein activity, particularly RGA1 activity to engineer drought tolerance and improved seed production in plants.

In one embodiment, the present invention provides for one or more plants whose germplasm has been modified to render a G-protein, particularly the RGA1 gene or its gene product inactive. Moreover, in further embodiments the invention relates to the offspring (e.g., F1, F2, F3, etc.) of a cross of said plant wherein the germplasm of said offspring has the same mutation as the parent plant. Therefore, embodiments of the present invention provide for plant varieties/hybrids whose germplasm contains a mutation, such that the phenotype of the plants is non-functional RGA1 gene activity in drought conditions. In some embodiments, said offspring (e.g., F1, F2, F3, etc.) are the result of a cross between elite lines, at least one of which contains a germplasm comprising a mutation that renders the G-protein such as RGA1 protein or gene of said plant inactive, particularly during drought.

In another embodiment, the present invention provides a method of improving seed development in drought conditions comprising inhibiting the activity of a G-protein, such as an RGA1 protein during drought conditions.

In another embodiment, the present invention provides a hybrid plant, line or variety, wherein said plant hybrid, line or variety comprises germplasm comprising one or more mutations in a G-protein encoding gene, or the RGA1 gene such that the G-protein or RGA1 protein is inactive during drought conditions. This can be by use of a naturally occurring mutation such as the d1 mutant, or preferably by introduction an expression cassette to said plant designed to reduce activity of the RGA1 or other related G-protein gene either constitutively or under drought conditions.

In some embodiments, said plant hybrid, line or variety is created by introgression of a plant germplasm that comprises said one or more modifications for rendering a G-protein or RGA1 gene or its encoded protein product inactive. In some embodiments, said plant hybrid, line or variety is created by incorporation of a heterologous genetic construct comprising designed to inhibit or otherwise decrease G-protein activity, particularly during drought conditions.

In another embodiment, the present invention provides a method for producing a plant hybrid, line or variety resistant to drought conditions and with improved seed production compared to a wild type plant under the same conditions comprising identifying a germplasm with a null G-protein or RGA1 modification, and introducing said germplasm into an elite plant hybrid, line or variety. In some embodiments, said introducing of said germplasm into said elite hybrid, line or variety is by introgression. In some embodiments, said introducing of said germplasm into said elite plant hybrid, line or variety is by introduction of a heterologous genetic construct.

In yet another embodiment, the present invention provides a plant hybrid, line or variety wherein the germplasm of said hybrid, line or variety confers drought tolerance with improved seed production.

In yet another embodiment, the present invention provides a method for identifying plant lines resistant to drought comprising supplying a nucleic acid sample from a plant, providing amplification primers for amplifying a region of a plant corresponding to an G-protein or RGA1 nucleic acid sample, applying said amplification primers to said nucleic acid sample such that amplification of said region of said G-protein gene occurs, and identifying plants resistant to drought based on the presence of one or more null mutations in said amplified nucleic acid sample.

In still another embodiment, the present invention provides for seeds wherein said germplasm of said seeds comprises a modified G-protein or RGA1 gene such that said mutation confers improved seed production under drought conditions.

In some embodiments, the present invention provides for a plant that comprises a heterologous nucleotide sequence that is at least 70% homologous, at least 80% homologous, at least 85% homologous, at least 90% homologous, at least 95% homologous, at least 97% homologous, or at least 99% homologous to the RGA1 gene of SEQ ID NO: 1, 2, 5, or 6. The invention also includes RGA1 polypeptides including the amino acid sequences of SEQ ID NO:3 or 4, conservatively modified variants which retain activity or loss of activity thereof as applicable.

In one embodiment, the present invention provides a method of producing plant seed comprising crossing a plant comprising a genetically modified G-protein or a genetically modified RGA1 gene with itself or a second plant and collecting said seed from said cross. In some embodiments, the methods for producing said seed comprises planting a parent seed line wherein said parent seed line comprises a germplasm confers a decrease in activity or a G-protein or RGA1 mutation with a parent pollinator plant line wherein said pollinator and/or seed line germplasm comprises a germplasm that confers a modified G-protein or RGA1 protein, growing said parent seed and pollinator plants together, allowing for the said parent seed plants to be pollinated by said parent pollinator plants, and harvesting the seed that results from said pollination.

In yet another embodiment, the invention provides for genetically modified plants incorporating a heterologous nucleotide construct encoding a RGA1 gene such as SEQ ID NOS: 1, 2, 5, or 6 operably linked to regulatory sequences such as expression cassettes, inhibition constructs, plants, plant cells, and seeds. The genetically modified plants, plant cells, and seeds of the invention may exhibit phenotypic changes, such as modulated RGA1 activity, particularly during drought conditions.

Methods are provided for reducing or eliminating the activity of a G-protein or RGA1 polypeptide in a plant, comprising introducing into the plant a selected polynucleotide. In specific methods, providing the polynucleotide decreases the level of RGA1 or related G-protein in the plant.

Methods are also provided for increasing the level of a modified RGA1 or G-protein polypeptide in a plant either constitutively or at specifically regulated times and tissues comprising introducing into the plant a selected polynucleotide with appropriate regulatory elements. In specific methods, expression of the modified RGA1 or G-protein polynucleotide improves the plants' tolerance to drought.

DEFINITIONS

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ Edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-B eta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, "conservatively modified variants" refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid, which encodes a polypeptide of the present invention, is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477-498 (1989)).

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extensions, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN <u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells.

Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

By "nucleic acid library" is meant a collection of isolated DNA or cDNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2$^{nd}$ ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein, "operably linked" includes reference to a functional linkage between a promoter and a second sequence, wherein the promoter sequence initiates and mediates transcription of the DNA sequence corresponding to the second sequence. Generally, "operably linked" means that the nucleic acid sequences being linked are contiguous and, where necessary to join two protein coding regions, contiguous and in the same reading frame.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants include maize, soybean, sunflower, sorghum, canola, wheat, alfalfa, cotton, rice, barley, and millet.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, nucleic acids to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and can be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C. for 20 minutes.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, New York (1995). In general a high stringency wash is 2×15 min in 0.5×SSC containing 0.1% SDS at 65° C.

As used herein, "genetically modified plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" or "genetically modified" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted h the local homology Smith and Waterman, Adv. Appl. Math. 2:482 (1981); by the homology alignment algorithm of Needleman and Wunsch. J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, California; GAP, BESTFIT, BLAST®, FASTA, and TFASTA in the Wisconsin Genetics Software Package, Genetics Computer Group (GCG), 575 Science Dr., Madison, Wisconsin, USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST® family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BIAST® 2.0 suite of programs using default parameters. Altschul et al., Nucleic Acids Res. 25:3389-3402 (1997). Software for performing BLAST analyses is publicly available, e.g., through the National Center for Biotechnology-Information World Wide Web at ncbi.nih.gov. This algorithm involves first identifying high scoring sequence pairs (HSPs) by identifying short words of length W in the query sequence, which either match or satisfy some positive-valued threshold score T When aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative, scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached, The BLAST® algorithm parameters W. T, and X determine the sensitivity and speed of the alignment. The BLASTN program (for nucleotide sequences) uses as defaults a word length (W) of 11, an expectation (E) of 10, a cutoff of 100, M=5, N=-4, and a comparison of both strands. For amino acid sequences, the BLASTP program uses as defaults a wordlength (W) of 3, an expectation (E)

of 10, and the BLOSUM62 scoring matrix (see Henikoff & Henikoff (1989) Proc. Natl. Acad. Sci. USA 89:10915).

In addition to calculating percent sequence identity, the BLAST® algorithm also performs a statistical analysis of the similarity between two sequences (see, e.g., Karlin & Altschul, Proc. Natl. Acad. Sci. USA 90:5873-5787 (1993)). One measure of similarity provided by the BLAST® algorithm is the smallest sum probability (P(N)), which provides an indication of the probability by which a match between two nucleotide or amino acid sequences would occur by chance.

BLAST® searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid sequence encodes is immunologically cross reactive with the polypeptide encoded by the second nucleic acid sequence.

(e) The terms "substantial identity" in the context of a peptide indicates that a peptide comprises a sequence with at least 70% sequence identity to a reference sequence, preferably 80%, or preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 12A-B is a sequence alignment of the coding region of rga1 and the d1 allele. (SEQ ID NO: 1 and 2 respectively).

FIG. 13 is a sequence alignment of the encoded proteins of rga1 and the d1 allele. (SEQ ID NO: 3 and 4 respectively).

FIGS. 14A-D is a sequence alignment of the genomic region of rga1 and the d1 allele. (SEQ ID NO: 5 and 6 respectively).

DETAILED DESCRIPTION OF THE PREFERRED EMBODIMENTS

Figure 1:
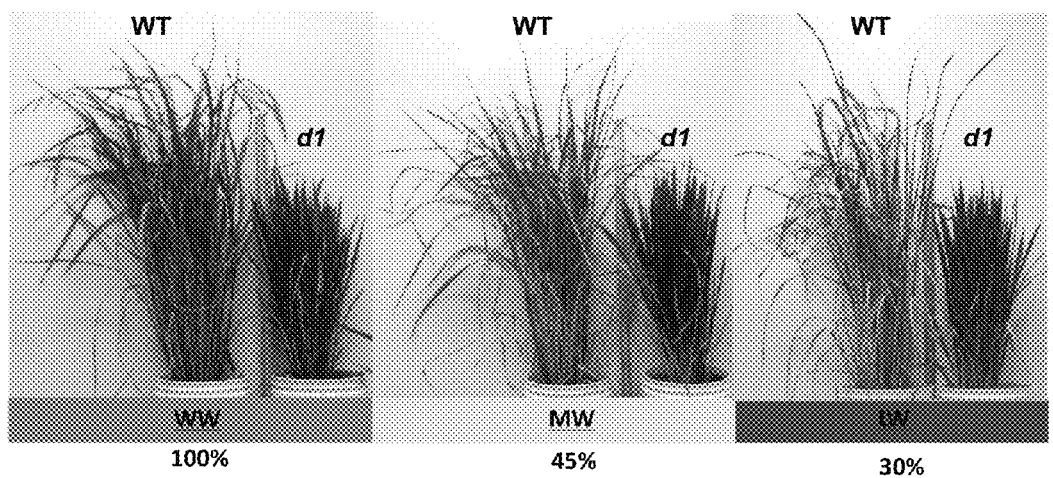
FIG. 1 shows the effects of water stress on wild-type and d1 plants during flowering and grain filling; mutant plants remain dark green and healthy while wild-type plants dry out and have a few living leaves under severe drought. The three watering conditions were: well-watered (100% soil relative water content), medium-water (45% soil relative water content), and low water (30% soil relative water content) conditions. Photographs were taken 140-160 days after emergence.

The rice dwarf mutant, d1, contains a non-functional RGA1 gene, encoding the GTP-binding α-subunit of the heterotrimeric G protein. This mutant was originally isolated as a spontaneous mutant with reduced height and shorter, erect, thicker, broad, dark green leaves, compact panicles, and short, round grains. Applicants have identified that a non-functional RGA1 gene or other related G-proteins can be used to create higher seed production and yield under drought conditions.

Thus the present invention provides for compositions and methods for producing plants that have higher yield in drought conditions by manipulating the G-proteins such as the RGA1 gene or protein. In particular, the present invention provides for plants, varieties, lines, and hybrids, as well as plant tissues and plant seeds that contain modified G-protein activity, particularly RGA1 activity to engineer drought tolerance and improved seed production in plants.

In one embodiment, the present invention provides for one or more plants whose germplasm has been modified to render a G-protein, particularly the RGA1 gene or its gene product inactive. Moreover, in further embodiments the invention relates to the offspring (e.g., F1, F2, F3, etc.) of a cross of said plant wherein the germplasm of said offspring has the same mutation as the parent plant. Therefore, embodiments of the present invention provide for plant varieties/hybrids whose germplasm contains a mutation, such that the phenotype of the plants is non-functional RGA1 gene activity in drought conditions. In some embodiments, said offspring (e.g., F1, F2, F3, etc.) are the result of a cross between elite lines, at least one of which contains a germplasm comprising a mutation that renders the G-protein such as RGA1 protein or gene of said plant inactive, particularly during drought.

In another embodiment, the present invention provides a method of improving seed development in drought conditions comprising inhibiting the activity of a G-protein, such as RGA1 protein during drought conditions.

In another embodiment, the present invention provides a hybrid plant, line or variety, wherein said plant hybrid, line or variety comprises germplasm comprising one or more mutations in a G-protein encoding gene, or the RGA1 gene such that the G-protein or RGA1 protein is inactive during drought conditions. This can be by use of a naturally occurring mutation such as the d1 mutant, or preferably by introduction an expression cassette to said plant designed to reduce activity of the RGA1 or other related G-protein gene either constitutively or under drought conditions.

In some embodiments, said plant hybrid, line or variety is created by introgression of a plant germplasm that comprises said one or more modifications for rendering a G-protein or RGA1 gene or its encoded protein product inactive. In some embodiments, said plant hybrid, line or variety is created by incorporation of a heterologous genetic construct comprising designed to inhibit or otherwise decrease G-protein activity, particularly during drought conditions.

In another embodiment, the present invention provides a method for producing a plant hybrid, line or variety resistant to drought conditions and with improved seed production compared to a wild type plant under the same conditions comprising identifying a germplasm with a null G-protein or RGA1 modification, and introducing said germplasm into an elite plant hybrid, line or variety. In some embodiments, said introducing of said germplasm into said elite hybrid, line or variety is by introgression. In some embodiments, said introducing of said germplasm into said elite plant hybrid, line or variety is by introduction of a heterologous genetic construct.

In yet another embodiment, the present invention provides a plant hybrid, line or variety wherein the germplasm of said hybrid, line or variety comprises drought tolerance with improved seed production.

In yet another embodiment, the present invention provides a method for identifying plant lines resistant to drought comprising supplying a nucleic acid sample from a plant, providing amplification primers for amplifying a region of a plant corresponding to a G-protein or RGA1 nucleic acid sample, applying said amplification primers to said nucleic acid sample such that amplification of said region of said G-protein gene occurs, and identifying plants resistant to drought based on the presence of one or more null mutations in said amplified nucleic acid sample.

In still another embodiment, the present invention provides for seeds wherein said germplasm of said seeds comprises a modified G-protein or RGA1 gene such that said mutation confers improved seed production under drought conditions.

In some embodiments, the present invention provides for a plant that comprises a heterologous nucleotide sequence that is at least 70% homologous, at least 80% homologous, at least 85% homologous, at least 90% homologous, at least 95% homologous, at least 97% homologous, or at least 99% homologous to the RGA1 gene of SEQ ID NO:1, 2, 5, or 6. The invention also includes RGA1 polypeptides including the amino acid sequences of SEQ ID NO: 3 or 4, conservatively modified variants which retain activity or loss of activity thereof as applicable.

In one embodiment, the present invention provides a method of producing plant seed comprising crossing a plant comprising a genetically modified G-protein or RGA1 gene with itself or a second plant and collecting said seed from said cross. In some embodiments, the methods for producing said seed comprises planting a parent seed line wherein said parent seed line comprises a germplasm confers a decrease in activity or a G-protein or RGA1 mutation with a parent pollinator plant line wherein said pollinator and/or seed line germplasm comprises a germplasm that confers a modified G-protein or RGA1 protein, growing said parent seed and pollinator plants together, allowing for the said parent seed plants to be pollinated by said parent pollinator plants, and harvesting the seed that results from said pollination.

In yet another embodiment, the invention provides for genetically modified plants incorporating a heterologous nucleotide construct encoding a RGA1 gene such as SEQ ID NOS: 1, 2, 5, or 6 operably linked to regulatory sequences such as expression cassettes, inhibition constructs, plants, plant cells, and seeds. The genetically modified plants, plant cells, and seeds of the invention may exhibit phenotypic changes, such as modulated RGA1 activity, particularly during drought conditions.

Methods are provided for reducing or eliminating the activity of a G-protein or RGA1 polypeptide in a plant, comprising introducing into the plant a selected polynucleotide. In specific methods, providing the polynucleotide decreases the level of RGA1 or related G-protein in the plant.

Methods are also provided for increasing the level of a modified RGA1 or G-protein polypeptide in a plant either constitutively or at specifically regulated times and tissues comprising introducing into the plant a selected polynucleotide with appropriate regulatory elements. In specific methods, expression of the modified RGA1 or G-protein polynucleotide improves the plant's tolerance to drought.

Molecular Biology Techniques

The following is a non-limiting general overview of molecular biology techniques which may be used in performing the methods of the invention.

Promoters

The constructs, promoters or control systems used in the methods of the invention may include a tissue specific promoter, an inducible promoter or a constitutive promoter.

A large number of suitable promoter systems are available. For example one constitutive promoter useful for the invention is the cauliflower mosaic virus (CaMV) 35S. It has been shown to be highly active in many plant organs and during many stages of development when integrated into the genome of transgenic plants and has been shown to confer expression in protoplasts of both dicots and monocots.

Organ-specific promoters are also well known. For example, the E8 promoter is only transcriptionally activated during tomato fruit ripening, and can be used to target gene expression in ripening tomato fruit (Deikman and Fischer, *EMBO J.* (1988) 7:3315; Giovannoni et al., *The Plant Cell* (1989) 1:53). The activity of the E8 promoter is not limited to tomato fruit, but is thought to be compatible with any system wherein ethylene activates biological processes. Similarly the Lipoxegenase ("the LOX gene") is a fruit specific promoter.

Other fruit specific promoters are the 1.45 promoter fragment disclosed in Bird, et al., *Plant Mol. Bio.*, pp 651-663 (1988) and the polygalacturonase promoter from tomato disclosed in U.S. Pat. No. 5,413,937 to Bridges et al.

Leaf specific promoters include as the AS-1 promoter disclosed in U.S. Pat. No. 5,256,558 to Coruzzi and the RBCS-3A promoter isolated from pea the RBCS-3A gene disclosed in U.S. Pat. No. 5,023,179 to Lam et al.

And finally root specific promoters include the CamV 35S promoter disclosed in U.S. Pat. No. 391,725 to Coruzzi et al; the RB7 promoter disclosed in U.S. Pat. No. 5,459,252 to Conking et al. and the promoter isolated from *Brassica napus* disclosed in U.S. Pat. No. 5,401,836 to Bazczynski et al. which give root specific expression.

Other examples of promoters include maternal tissue promoters such as seed coat, pericarp and ovule. Promoters highly expressed early in endosperm development are most effective in this application. Of particular interest is the promoter from the a' subunit of the soybean β-conglycinin gene [Walling et al., *Proc. Natl. Acad. Sci. USA* 83:2123-2127 (1986)] which is expressed early in seed development in the endosperm and the embryo.

Further seed specific promoters include the Napin promoter described in U.S. Pat. No. 5,110,728 to Calgene, which describes and discloses the use of the napin promoter in directing the expression to seed tissue of an acyl carrier protein to enhance seed oil production; the DC3 promoter from carrots which is early to mid embryo specific and is disclosed at *Plant Physiology*, October 1992 100(2) p. 576-581, "Hormonal and Environmental Regulation of the Carrot Lea-class Gene Dc 3, and *Plant Mol. Biol.*, April 1992, 18(6) p. 1049-1063, "Transcriptional Regulation of a Seed Specific Carrot Gene, DC 8": the phaseolin promoter described in U.S. Pat. No. 5,504,200 to Mycogen which discloses the gene sequence and regulatory regions for phaseolin, a protein isolated from *P. vulgaris* which is expressed only while the seed is developing within the pod, and only in tissues involved in seed generation.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans. R. Soc. London* (1986) B314-343. mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

Another very important method that can be used to identify cell type specific promoters that allow identification of genes expressed even in a single cell is enhancer detection (O'Kane, C., and Gehring, W. J. (1987), "Detection in situ of genomic regulatory elements in *Drosophila*", *Proc. Natl. Acad. Sci. USA*, 84, 9123-9127). This method was first developed in *Drosophila* and rapidly adapted to mice and plants (Wilson, C., Pearson, R. K., Bellen, H. J., O'Kane, C. J., Grossniklaus, U., and Gehring, W. J. (1989)), "P-element-mediated enhancer detection: an efficient method for isolating and characterizing developmentally regulated genes in *Drosophila*", *Genes & Dev.*, 3, 1301-1313; Skarnes, W. C. (1990), "Entrapment vectors: a new tool for mammalian genetics", *Biotechnology*, 8, 827-831; Topping, J. F., Wei, W., and Lindsey, K. (1991), "Functional tagging of regulatory elements in the plant genome", *Development*, 112, 1009-1019; Sundaresan, V., Springer, P. S., Volpe, T., Haward, S., Jones, J. D. G., Dean, C., Ma, H., and Martienssen, R. A., (1995), "Patterns of gene action in plant development revealed by enhancer trap and gene trap transposable elements", *Genes & Dev.*, 9, 1797-1810).

The promoter used in the method of the invention may be an inducible promoter. An inducible promoter is a promoter that is capable of directly or indirectly activating transcription of a DNA sequence in response to an inducer. In the absence of an inducer, the DNA sequence will not be transcribed. Typically, the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 kD heat shock promoter of (Freeling, M., Bennet, D. C., Maize ADN 1, *Ann. Rev. of Genetics*, 19:297-323) and the alcohol dehydrogenase promoter which is induced by ethanol (Nagao, R. T., et al., Miflin, B. J., Ed. Oxford Surveys of Plant Molecular and Cell Biology, Vol. 3, p. 384-438, Oxford University Press, Oxford 1986) or the Lex A promoter which is triggered with chemical treatment and is available through Ligand Pharmaceuticals. The inducible promoter may be in an induced state throughout seed formation or at least for a period which corresponds to the transcription of the DNA sequence of the recombinant DNA molecule(s).

Another example of an inducible promoter is the chemically inducible gene promoter sequence isolated from a 27 kD subunit of the maize glutathione-S-transferase (GST II) gene. Two of the inducers for this promoter are N,N-diallyl-2,2-dichloroacetamide (common name: dichloramid) or benzyl-=2-chloro-4-(trifluoromethyl)-5-thiazolecarboxylate (common name: flurazole). In addition, a number of other potential inducers may be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI.

Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, PR-1, PR-A, PR-S, the cucumber chitinase gene, and the acidic and basic tobacco beta-1,3-glucanase genes. There are numerous potential inducers for these promoters, as described in Application No. EP89/103888.7.

The preferred promoters may be used in conjunction with naturally occurring flanking coding or transcribed sequences of the feronia regulatory genes or with any other coding or transcribed sequence that is critical to pollen tube formation and/or fertilization.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to female gametophyte development and/or function.

Additionally, regions of one promoter may be joined to regions from a different promoter in order to obtain the desired promoter activity resulting in a chimeric promoter. Synthetic promoters which regulate gene expression may also be used.

The expression system may be further optimized by employing supplemental elements such as transcription terminators and/or enhancer elements.

Other Regulatory Elements

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the *Agrobacterium* octopine synthase signal (Gielen et al., *EMBO J.* (1984) 3:835-846) or the nopaline synthase signal (Depicker et al., *Mol. and Appl. Genet.* (1982) 1:561-573).

Marker Genes

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance and the hygromycin resistance gene. Transformed plant cells thus selected can be induced to differentiate into plant structures which will eventually yield whole plants. It is to be understood that a selection marker gene may also be native to a plant.

Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10: 1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8: 238 (1989). See also, U.S. Pat. No. 5,563,055, (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559-563 (1988), Sanford, J. C., *Physiol Plant* 79: 206 (1990), Klein et al., *Biotechnology* 10: 268 (1992). See also U.S. Pat. No. 5,015,580 (Christou, et al), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.*, 4: 2731 (1985), Christou et al., *Proc Natl. Acad. Sci. U.S.A.* 84: 3962 (1987). Direct uptake of DNA into protoplasts using $CaCl_2$ precipitation, polyvinyl alcohol or poly-L-ornithine have also been reported. Hain et al., *Mol. Gen. Genet.* 199: 161 (1985) and Draper et al., *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495-1505 (1992) and Spencer et al., *Plant Mol. Biol.* 24: 51-61 (1994).

Following transformation of target tissues, expression of the above-described selectable marker genes allows for preferential selection of transformed cells, tissues and/or plants, using regeneration and selection methods now well known in the art.

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art.

The transformed cells may then be regenerated into a transgenic plant. The regenerated plants are transferred to standard soil conditions and cultivated in a conventional manner.

After the expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

As indicated above, it may be desirable to produce plant lines which are homozygous for a particular gene. In some species this is accomplished rather easily by the use of another culture or isolated microspore culture. This is especially true for the oil seed crop *Brassica napus* (Keller and Armstrong, Z. Pflanzenzucht 80:100-108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by Southern blot analysis in which careful attention is paid to the loading of exactly equivalent amounts of DNA from the mixed population, and scoring heterozygotes by the intensity of the signal from a probe specific for the inserted gene. It is advisable to verify the results of the Southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

Molecular Markers

The present invention provides a method of genotyping a plant comprising a heterologous polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., Clark, Ed., Plant Molecular Biology: A Laboratory Manual. Berlin, Springer Verlag, 1997. Chapter 7. For molecular marker methods, see generally, "The DNA Revolution" in: Paterson, A. H., Genome Mapping in Plants (Austin, Tex., Academic Press/R. G. Landis Company, 1996) pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed.

Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5,3,2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention.

Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5'UTR) of the RNA. Positive sequence motifs include translational initiation consensus sequences (Kozak, Nucleic Acids Res. 15: 8125 (1987)) and the 7-methylguanosine cap structure (Drummond et al., Nucleic Acids Res. 13: 7375 (1985)). Negative elements include stable intramolecular 5' UTR stem-loop structures (Muesing et al., Cell 48: 691 (1987)) and AUG sequences or short open reading frames preceded by an appropriate AUG in the 5'UTR (Kozak, supra, Rao et al., Mol. and Cell. Biol. 8: 284 (1988)). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., Nucleic Acids Res. 12: 387-395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.-H., et al. Proc. Natl. Acad. Sci. USA 94: 4504-4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased Km and/or increased KCat over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms.

Alternatively, a polynucleotide having a consensus sequence generated from orthologous genes can be used to identify or isolate orthologs of other taxa. Typically, a polynucleotide having a consensus sequence will be at least 25, 30, or 40 in nucleotides in length. As those of skill in the art are aware, a conservative amino acid substitution can be used for amino acids which differ amongst aligned sequences but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST® algorithm's smallest sum probability (P (N)) Various suppliers of sequence-analysis software are listed in chapter 7 of Current Protocols in Molecular Biology, F.M. Ausubel et al., Eds., Current Protocols, a joint venture between Greene Publishing Associates, Inc. and John Wiley & Sons, Inc. (Supplement 30).

A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Reducing the Activity and/or Level of an RGA1 Polypeptide

Methods are also provided to reduce or eliminate the activity of an RGA1 polypeptide by transforming a plant cell with an expression cassette that expresses a polynucleotide that inhibits the expression of the RGA1. The polynucleotide may inhibit the expression of the RGA1 directly, by preventing transcription or translation of the RGA1 messenger RNA, or indirectly, by encoding a polypeptide that inhibits the transcription or translation of an RGA1 gene encoding an RGA1 polypeptide. Methods for inhibiting or eliminating the expression of a gene in a plant are well known in the art, and any such method may be used in the present invention to inhibit the expression of the RGA1 polypeptide. Many methods may be used to reduce or eliminate the activity of an RGA1 polypeptide. In addition, more than one method may be used to reduce the activity of a single RGA1 polypeptide.

1. Polynucleotide-Based Methods:

In some embodiments of the present invention, a plant is transformed with an expression cassette that is capable of expressing a polynucleotide that inhibits the expression of an RGA1 polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one RGA1 polypeptide is an expression cassette capable of producing an RNA molecule that inhibits the transcription and/or translation of at least one RGA1 polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an RGA1 polypeptide include sense Suppression/Cosuppression, where an expression cassette is designed to express an RNA molecule corresponding to all or part of a messenger RNA encoding an RGA1 polypeptide in the "sense" orientation and over expression of the RNA molecule can result in reduced expression of the native gene; Antisense Suppression where the expression cassette is designed to express an RNA molecule complementary to all or part of a messenger RNA encoding the RGA1 polypeptide and over expression of the antisense RNA molecule can result in reduced expression of the native gene; Double-Stranded RNA Interference, where a sense RNA molecule like that described above for cosuppression and an antisense RNA molecule that is fully or partially complementary to the sense RNA molecule are expressed in the same cell, resulting in inhibition of the expression of the corresponding endogenous messenger RNA, Hairpin RNA Interference and Intron-Containing Hairpin RNA Interference.

Where the expression cassette is designed to express an RNA molecule that hybridizes with itself to form a hairpin structure that comprises a single-stranded loop region and a base-paired stem, Small Interfering RNA or Micro RNA, where the expression cassette is designed to express an RNA molecule that is modeled on an endogenous miRNA such as small interfering RNA or artificial micro RNAs.

2. Polypeptide-Based Inhibition of Gene Expression

In one embodiment, the polynucleotide encodes a zinc finger protein that binds to a gene encoding an RGA1 polypeptide, resulting in reduced expression of the gene methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 2003/0037355; each of which is herein incorporated by reference.

3. Polypeptide-Based Inhibition of Protein Activity

In some embodiments of the invention, the polynucleotide encodes an antibody that binds to at least one RGA1 polypeptide and reduces the activity of the RGA1 polypeptide. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an RGA1 polypeptide is reduced or eliminated by disrupting the gene encoding the RGA1 polypeptide. The gene encoding the RGA1 polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have a desired trait or phenotype.

In certain embodiments the nucleic acid sequences of the present invention can be stacked with any combination of polynucleotide sequences of interest in order to create plants with a desired phenotype. For example, the polynucleotides of the present invention may be stacked with any other polynucleotides of the present invention, (SEQ ID NO: 1), or with other genes implicated in herbicide resistance. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409)); barley high lysine (Williamson et al. (1987) Eur. J. Biochem. 165:99-106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12: 123)); increased digestibility (e.g., modified storage proteins (U.S. application Ser. No. 10/053,410, filed Nov. 7, 2001)); and thioredoxins (U.S. application Ser. No. 10/005,429, filed Dec. 3, 2001), the disclosures of which are herein incorporated by reference.

The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) Gene 48:109); lectins (Van Damme et al. (1994) Plant Mol. Biol. 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene and GAT gene)); and traits desirable for processing or process products such as high oil (U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (U.S. Pat. No. 5,602,321); beta-ketothiolase, polyhydroxybutyrate synthase, and acetoacetyl-CoA reductase (Schubert et al. (1988) J. Bacteriol. 170:5837-5847), which facilitate expression of polyhydroxyalkanoates (PHAs)), the disclosures of which are herein incorporated by reference. One could also combine the polynucleotides of the present invention with polynucleotides providing agronomic traits such as male sterility (see U.S. Pat. No. 5,583,210), stalk strength, flowering time, or transformation technology traits such as cell cycle regulation or gene targeting (see, WO 99/61619; WO 00/17364; WO 99/25821), the disclosures of which are herein incorporated by reference.

These stacked combinations can be created by any method including, but not limited to, polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

Use in Breeding Methods

The transformed plants of the invention may be used in a plant breeding program. The goal of plant breeding is to combine, in a single variety or hybrid, various desirable traits. For field crops, these traits may include, for example, resistance to diseases and insects, tolerance to heat and drought, tolerance to high planting density, reduced time to crop maturity, greater yield, and better agronomic quality. With mechanical harvesting of many crops, uniformity of plant characteristics such as germination and stand establishment, growth rate, maturity, and plant height is desirable. Traditional plant breeding is an important tool in developing new and improved commercial crops. This invention encompasses methods for producing a plant by crossing a first parent plant with a second parent plant wherein one or both of the parent plants is a transformed plant according to the invention displaying drought tolerance as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids, and transformation. Often combinations of these techniques are used.

The development of hybrids in a plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using transformation techniques can be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation, then the transgenic plants could be crossed to a different inbred in order to produce a transgenic hybrid plant. As used herein, "crossing" can refer to a simple X by Y cross, or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly uniform; and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present invention may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

The following examples are offered by way of illustration and not by way of limitation.

EXAMPLE 1

P14 Characterization of Drought Tolerance in the Rice G-Protein α Subunit Mutant, d1

The rice dwarf mutant, d1, contains a non-functional RGA1 gene, encoding the GTP-binding α-subunit of the heterotrimeric G protein. This mutant was originally isolated as a spontaneous mutant with reduced height and shorter, erect, thicker, broad, dark green leaves, compact panicles, and short, round grains. We have examined the physiological responses of the d1 mutant to mild and severe water limitation during both vegetative and reproductive development in comparison with its background line. The d1 plants present higher photosynthetic rates, stomatal conductance, and $\psi_{leaf}$ than wild type during both mild and severe water limitation, and have a greater number and percentage of tillers producing panicles, with resulting higher reproductive yield. The d1 plants also perform better than wild-type plants under high planting densities.

FIG. 1 shows water stress during flowering and grain filling; mutant plants remain dark green and healthy while wild-type plants dry out and have a few living leaves under severe drought. The three watering conditions were: well-watered (100% soil relative water content), medium-water (45% soil relative water content), and low water (30% soil relative water content) conditions. Photographs were taken 140-160 days after emergence.

Figure 2:
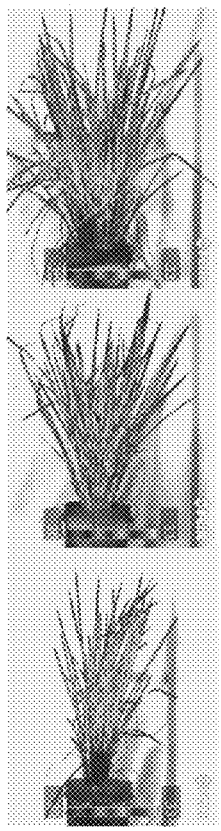
FIG. 2 shows leaf temperatures on plants 165 days after emergence were measured by infrared thermography using a FLIR T620 Thermal Imaging Camera (FLIR Systems, USA). In order to obtain reliable comparisons, images were obtained over the shortest time interval possible; approximately 15 minutes total. Pseudo-colored temperature scales are indicated directly on the photographs.
Figure 2:
Figure 2:
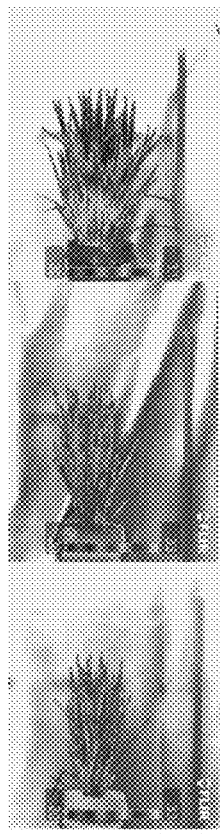
Figure 2:

FIG. 2 shows that d1 plants exhibit lower leaf temperatures than wild-type plants under all 3 watering conditions. Leaf temperatures on plants 165 days after emergence were measured by infrared thermography using a FLIR T620 Thermal Imaging Camera (FLIR Systems, USA). In order to obtain reliable comparisons, images were obtained over the shortest time interval possible; approximately 15 minutes total. Pseudo-colored temperature scales are indicated directly on the photographs.

Figure 3:
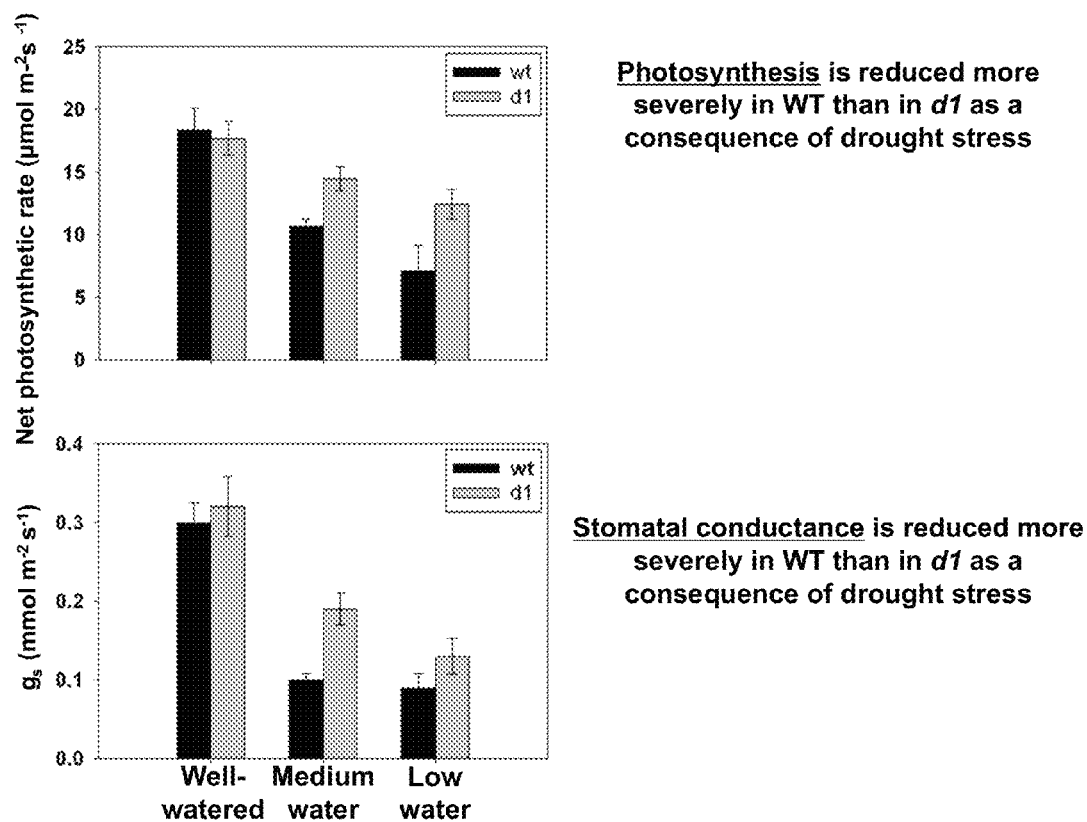
FIG. 3 shows that net photosynthesis and stomatal conductance measured on leaves between 120 and 130 days after emergence, using a Li-Cor 6400 Portable Photosynthesis System. Light intensity was 500 µmol m$^{-2}$s$^{-1}$.

FIG. 3 shows that net photosynthesis and stomatal conductance are reduced more severely in wild-type plants than in d1 mutants under medium-water (45% soil relative water content) and low-water (30% soil relative water content) conditions, while these parameters are statistically identical under well-watered (100% soil relative water content) conditions. Parameters were measured on leaves between 120 and 130 days after emergence, using a Li-Cor 6400 Portable Photosynthesis System. Light intensity was 500 mmol m$^{-2}$s$^{-1}$.

Figure 4:
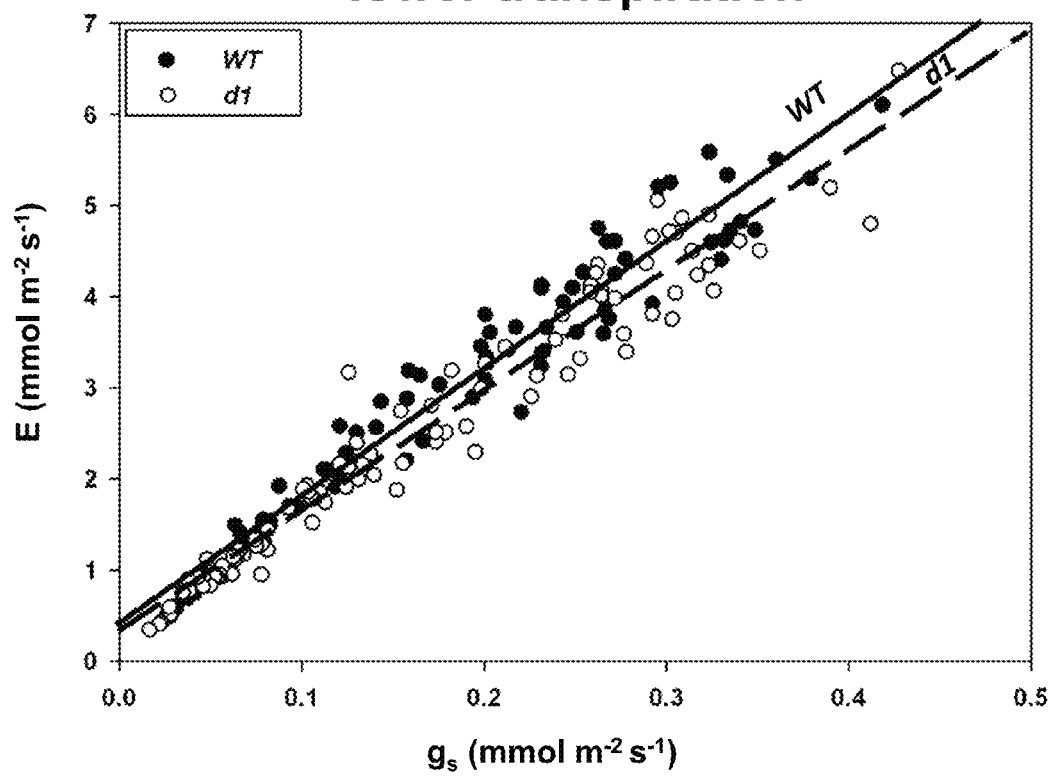
FIG. 4 shows the relationship between stomatal conductance and transpiration, measured under ambient conditions of 500 µmol m$^{-2}$s$^{-1}$ light intensity and 30° C. temperature using a Li-Cor 6400 Portable Photosynthesis System. Measurements were taken on seedlings at 40 days after emergence. Each data point represents an individual plant. Lines depicted are regression lines for each genotype; ANCOVA analysis demonstrated significant differences (P<0.05) in the slopes.

FIG. 4 shows that d1 mutants have higher stomatal conductance but nevertheless lose less water (have lower transpiration rates) than wild-type plants. This is presumably due to the lower leaf temperatures of d1 plants as compared to wild-type (as shown in FIG. 3); lower leaf temperatures result in a reduced vapor pressure deficit, i.e. a reduced physical driving force for evaporative water loss. Measurements were made under ambient conditions of 500 μmol m$^{-2}$s$^{-1}$ light and 30° C. temperature using a Li-Cor 6400 Portable Photosynthesis System. Measurements were taken on seedlings at 40 days after emergence. Each data point represents an individual plant. Lines depicted are regression lines for each genotype; ANCOVA analysis demonstrated significant differences (P<0.05) in the slopes.

Figure 5:
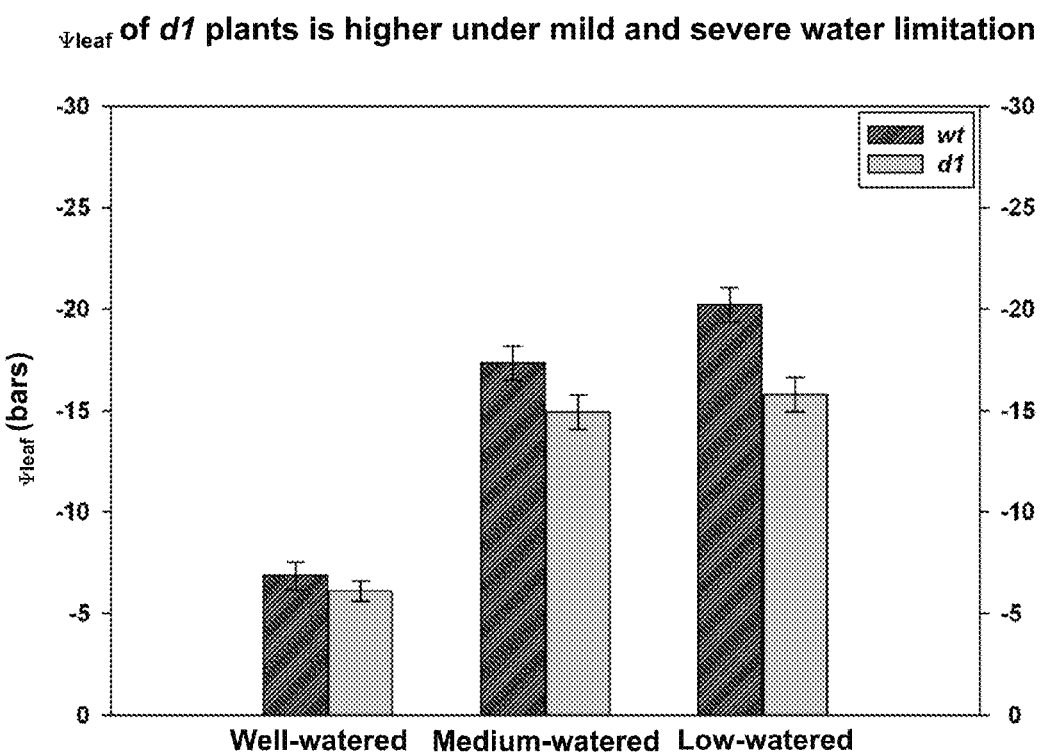
FIG. 5 shows $\psi_{leaf}$ measurements, which were made using a Scholander pressure chamber. Measurements were taken on the flag leaf of the primary tiller of plants 120-130 days after emergence.

FIG. 5 shows that the water potential ($\psi_{leaf}$) of d1 plants is higher than that of wild-type plants under medium-water and low-water conditions, and equal to that of wild-type plants under well-watered conditions (the three watering regimes were specified above). $\psi_{leaf}$ measurements, made using a Scholander pressure chamber, were taken from the flag leaf of the primary tiller of plants 120-130 days after emergence.

Taken together, FIGS. 3-5 show that d1 plants have improved water status and higher photosynthetic rates than wild-type plants under drought conditions.

Figure 6:
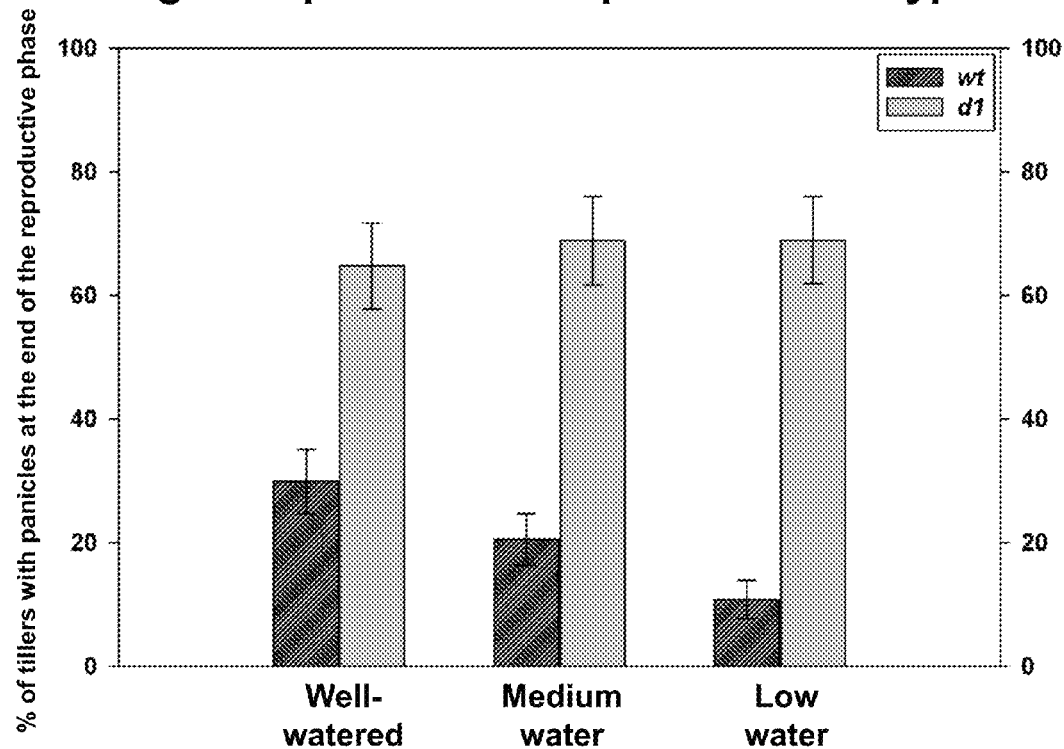
FIG. 6 is a graph showing the percentage of stalks flowering at the end of the reproductive phase in high water, medium water, and low water conditions.

FIG. 6 is a graph showing the percentage of stalks flowering at the end of the reproductive phase in high water, low water and medium water conditions. One can see that water limitation decreases the number of stalks developing a flower head in wild-type plants but not in d1 mutants.

Figure 7:
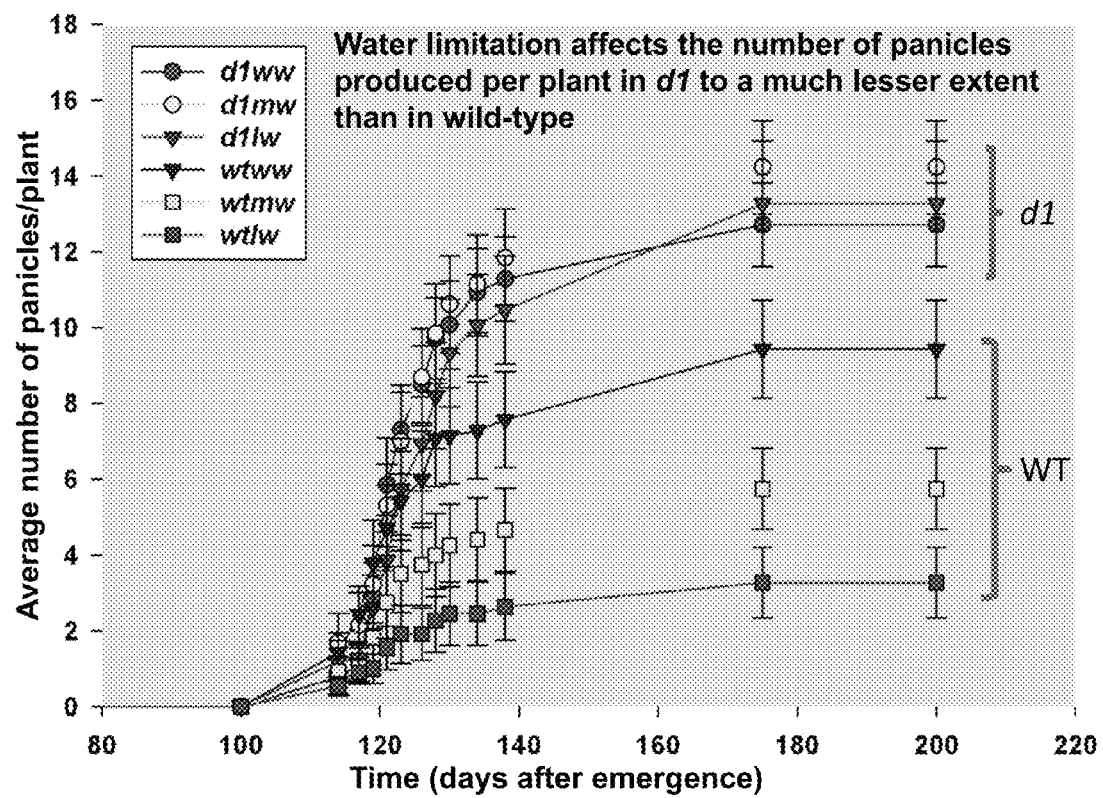
FIG. 7 shows the average number of panicles produced through time in d1 and wild-type plants.

FIG. 7 shows the average number of panicles produced through time in d1 and wild-type plants. Panicle production is greater in the d1 mutant than in wild-type plants. Water-limited conditions result in a pronounced reduction in the average number of panicles produced by wild-type plants but do not affect average panicle production in d1 plants.

Figure 8:
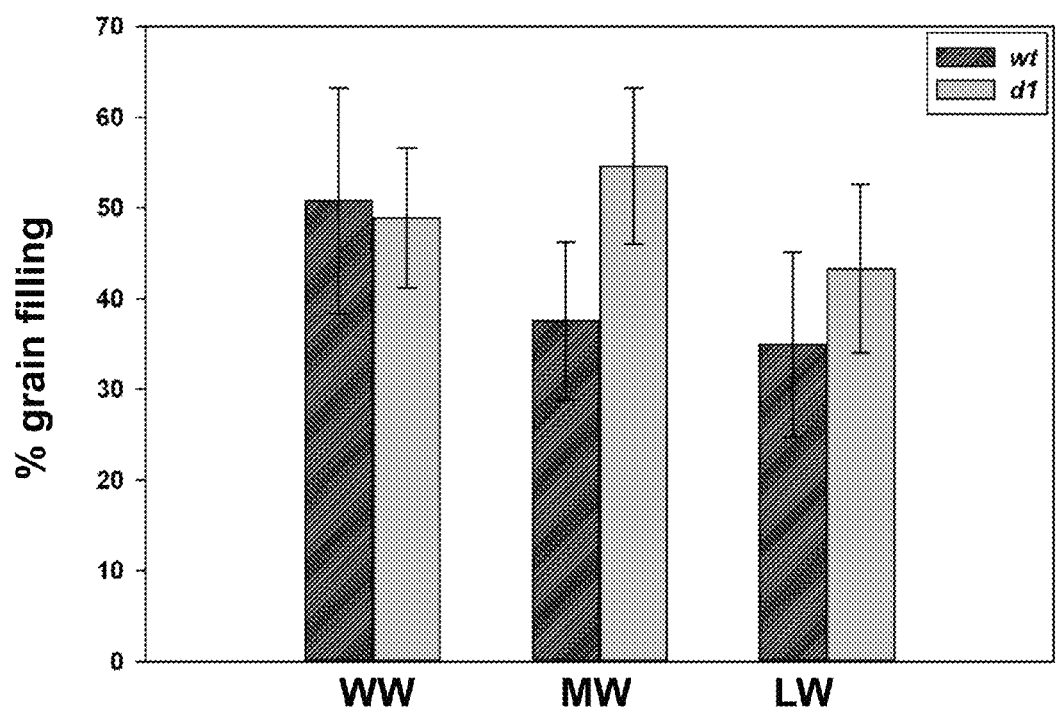
FIG. 8 shows the percentage of grain viability at the end of the reproductive cycle under high water, medium water and low water conditions. Data were obtained from 6 panicles randomly selected for analysis from 6 different plants of each genotype and water treatment combination, measured at the end of the life cycle.

FIG. 8 shows drought-induced grain abortion per panicle in wild-type and d1 plants under the three watering regimes. The data are from 6 panicles randomly selected for analysis from 6 different plants of each genotype and water treatment combination, measured at the end of the life cycle.

Figure 9:
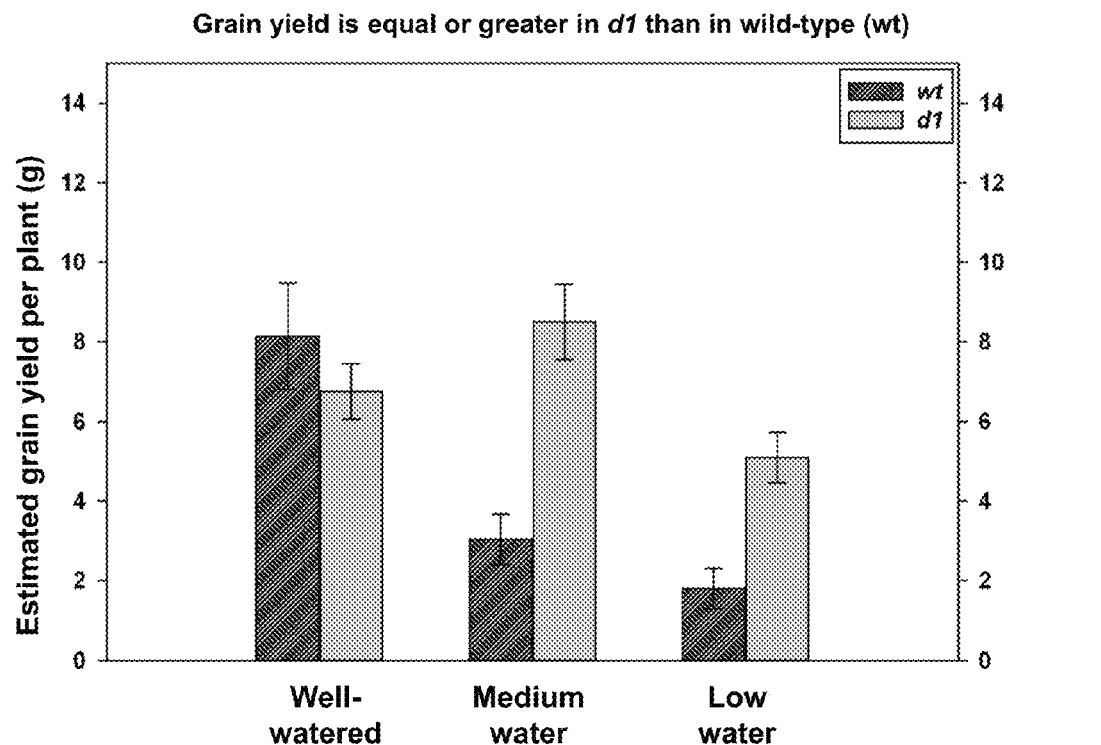
FIG. 9 is graph of yield of d1 and WT in well watered, medium water and low water conditions.

Taken together, the above 8 figures show the basis for the increased grain yield by d1 plants as compared to wild-type plants under drought conditions: FIG. 9 shows that estimated grain yield per plant is statistically equal in wild-type and mutant d1 plants under well-watered conditions and is much higher in d1 mutants than in wild-type plants under drought conditions.

Figure 10:
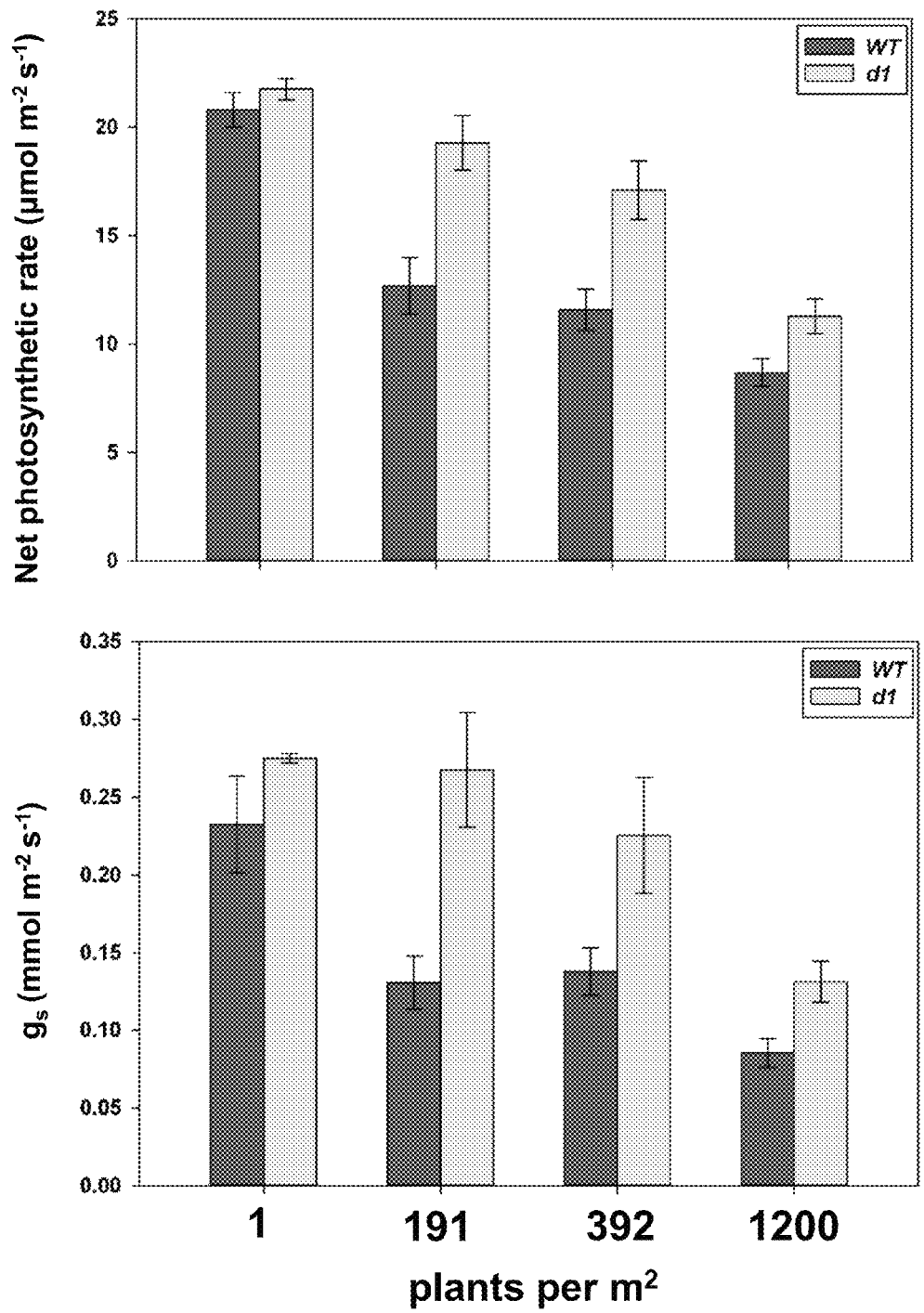
FIG. 10 shows net photosynthesis and stomatal conductance at 1500 µmol m$^{-2}$s$^{-1}$ light measured on the flag leaf of the primary tiller at 60 days after emergence using a Li-Cor 6400 Portable Photosynthesis System.

FIG. 10 shows that in the absence of drought stress, increased planting density reduces photosynthesis at light saturation to a greater extent in wild-type than in the d1 mutant. Plants were grown in monospecific stands at the indicated planting densities. Net photosynthesis at 1500 μmol m$^{-2}$s$^{-1}$ light was measured on the flag leaf of the primary tiller at 60 days after emergence using a Li-Cor 6400 Portable Photosynthesis System.

Figure 11:
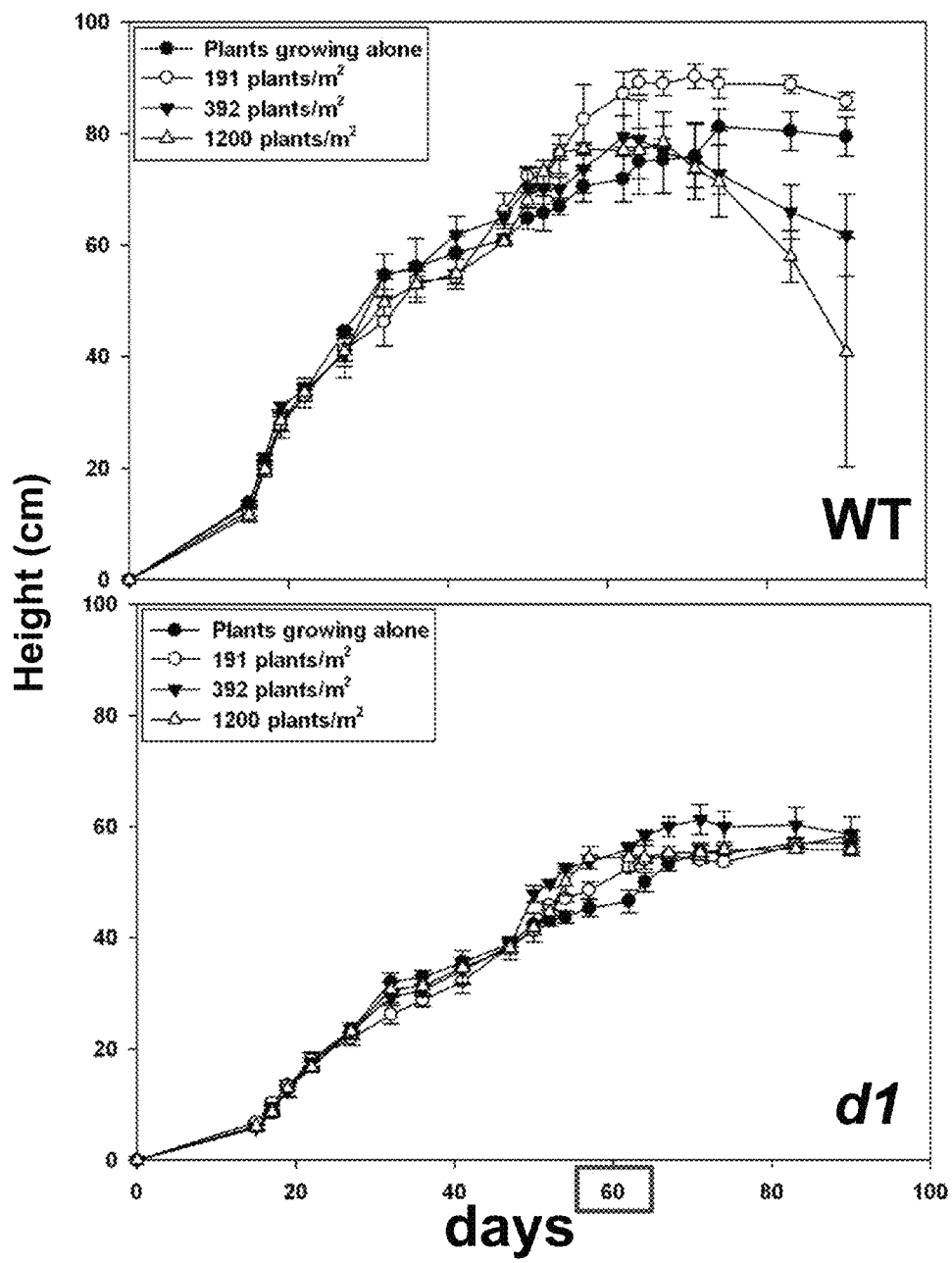
FIG. 11 shows that high planting density compromises plant growth and survival (as indicated by plant height) earlier in wild-type than in d1 plants.

FIG. 11, from the same experiment as FIG. 10, shows that high planting density compromises plant growth and survival (as indicated by plant height) earlier in wild-type than in d1 plants.

Higher photosynthetic rates and improved survival at increased planting density are favorable agronomic traits. FIGS. 10 and 11 show that these traits are exhibited to a greater extent by the d1 mutant than by wild-type plants.

EXAMPLE 2

Plant Heterotrimeric G Protein Function: Insights from *Arabidopsis* and Rice Mutants Laetitia Perfus-Barbeoch, Alan M. Jones and Sarah M. Assmann Heterotrimeric G proteins have been implicated in a wide range of plant processes. These include responses to hormones, drought, and pathogens, and developmental events such as lateral root formation, hypocotyl elongation, hook opening, leaf expansion, and silique development. Results and concepts emerging from recent phenotypic analyses of G-protein component mutants in *Arabidopsis* and rice are adding to our understanding of G-protein mechanisms and functions in higher plants.

Introduction

Heterotrimeric GTP-binding proteins (G proteins) provide a key mechanism by which a specific signaling cascade is switched on or off to translate an incoming signal into a specific cellular response. In recent years, much has been learned about the diversity of signal transduction through plant G proteins thanks to the identification and mutation of genes in *Arabidopsis* and rice (*Oryza sativa*) that encode specific G-protein components. These components include the α, β, and γ subunits of the G protein heterotrimer, possible heptahelical G-protein-coupled receptors (GPCRs), and regulator of G-protein signaling proteins (RGS). Such studies are revealing two crucial concepts. First, some physiological responses are predominantly mediated by Gα, whereas others are predominantly mediated by Gβγ. Second, the particular role of any given G-protein component in plant developmental processes [1,2,3] and responses to biotic and abiotic stresses [4-7,8] can differ in a cell-type- or developmental-stage-specific manner. Thus, one mutant can even show opposite phenotypic responses to the same stimulus, depending on the particular cell or tissue under study. To highlight these concepts, in this review, we discuss the latest genetic studies on plant G-protein signaling from an 'organ' point-of-view (FIG. 1). The reader may also be interested in reviews on plant heterotrimeric G proteins that have emphasized comparisons with mammalian systems [9-13].

The Heterotrimeric G-Protein Paradigm

The G protein itself consists of three different subunits, α, β, and γ (respectively named Gα, Gβ, and Gγ), which form a heterotrimeric complex in the inactive state. Binding of an agonist (i.e. an activating ligand) to its specific GPCR leads to the conversion of an inactive G protein to its active conformation. The GPCR acts as a guanine nucleotide exchange factor, causing Gα to exchange GDP for GTP. As a result, Gα-GTP separates from the Gβγ dimer and both Gα-GTP and the Gβγ dimer separate from the receptor and can activate downstream effectors. Subsequent to signal propagation, the GTP that is bound to Gα is hydrolyzed to GDP, thereby inactivating Gα and allowing its re-association with the Gβγ dimer to reform the inactive heterotrimeric complex. RGS proteins act as GTPase-activating proteins (GAPs) for Gα, typically attenuating signaling by hastening the return of the G protein to the resting state.

G-Protein Components in *Arabidopsis* and Rice

Candidate genes that encode polypeptides that are similar to mammalian G-protein components have been isolated from several higher plant species (summarized in [11]). In *Arabidopsis* and rice, Gα is encoded by a single copy gene, designated GPA1 or RGA1, respectively [14,15]. Gβ is likewise encoded by a single-copy gene, designated AGB1 or RGB1, respectively [16,17]. Two Gγ genes were recently isolated from *Arabidopsis* and rice: AGG1 or RGG1 [18,19] and AGG2 or RGG2 [19,20]. No plant gene has been found that is highly homologous to metazoan GPCRs. However, in *Arabidopsis*, GCR1 is a likely candidate as a GPCR-encoding gene because it encodes a protein that has some GPCR sequence similarity and a predicted heptahelical structure that is the hallmark of bona fide GPCRs [8,21,22]. Finally, it appears that the *Arabidopsis* genome contains only one member of the RGS family, RGS1 [23]. Transgenic plants that ectopically and/or conditionally express each of the above-described components, except the Gγ subunit genes, have been described recently (Table 1), and various single, double, and triple mutants have been generated (Table 1).

On the basis of both modeling [3**] and experimentation, the basic paradigm of mammalian G-protein signaling described above also appears to operate in plants [13]. Gα, Gβ, Gγ, GCR1 and RGS1 can all be found at the plasma membrane of plant cells[1,8,19,22,23,24,25]. In yeast two-hybrid assays and co-immunoprecipitation experiments, Gβ interacts tightly with both Gγ subunits in both *Arabidopsis* and rice [18,19,20]. In rice, gel-filtration experiments have confirmed that Gβγ dimers associate with Gα. This association is disrupted by a non-hydrolysable form of GTP, GTPγS, which is expected to maintain the activated conformation of Gα [19]. Pandey and Assmann [8] used in planta and in vitro co-immunoprecipitation as well as split-ubiquitin yeast two-hybrid assays to provide the first conclusive evidence that the putative GPCR, GCR1, physically interacts with Gα. RGS1 interacts with both a constitutively active GPA1 (GPA1$^{QL}$, the GTPase-deficient version of GPA1) and wild-type GPA1, and the carboxy-terminal domain of AtRGS1 has been shown to exert GAP activity on a yeast Gα [23].

Striking differences also exist, however, between the G-protein components of plants and those of other eukaryotic organisms: the sequence similarity of the relevant genes and proteins is limited, and a much smaller number of genes encode each of the different components in plants than in other eukaryotes [13].

G-Protein Signaling in Seeds

Seed germination is a complex phenomenon that is modulated by numerous signals, including gibberellins (GA), abscisic acid (ABA), brassinosteroids (BR), ethylene, light, and sugars, some acting in concert and others in opposition [26]. Current models of seed germination in non-graminaceous species suggest that BR act downstream of GA to promote germination. Both ABA and sugars inhibit germination, and ethylene negatively regulates ABA's effects.

In the absence of stratification, gpa1-1 and gpa1-2 mutant seeds exhibit delayed germination [27], suggesting that they are more dormant than wild-type seeds. Consistent with this phenomenon, gpa1 mutants exhibit moderately increased sensitivity to the inhibition of germination by ABA and sugars [2,27]. Many of these phenotypes are also observed in *Arabidopsis* T-DNA insertional mutants of Pirin1, a cupin-domain protein that has been identified as a GPA1 interactor in yeast two-hybrid assays [27].

Because gpa1 seeds have wild-type ABA concentrations [2], the results described above presumably reflect either an increased sensitivity to ABA or a decreased sensitivity to stimulatory signals such as GA. In support of the latter hypothesis, the germination of gpa1 and agb1 seeds is significantly less sensitive to exogenous GA and significantly more sensitive to the GA-synthesis inhibitor paclobutrazol than the germination of wild-type seeds [2,22]. Ullah et al. [2] speculate that GPA1 controls the sensitivity of the GA pathway because although the overexpression of GPA1 in *Arabidopsis* confers a millionfold increase in the GA sensitivity of seed germination, the requirement for GA is not abolished. If GPA1 directly coupled the GA response, then the ectopic expression of GPA1 would be expected to confer GA independence, which is not the case. Ullah et al. [2] further suggest that BR controls GA sensitivity in a GPA1-dependent manner, because brassinolide (BL) rescue of germination in seeds treated with paclobutrazol is complete for wild-type seeds but only partial for gpa1 and agb1 seeds [2,22,28].

Like gpa1 mutants, gcr1 mutants exhibit reduced sensitivity toward GA and BR in seed germination, whereas GCR1 overexpression reduces seed dormancy [22,29]. Under some but not all conditions, seeds of gcr1 gpa1 and gcr1 agb1 double mutants have additive or synergistic germination responses to GA and BR, which is unexpected if GCR1 were to function upstream of the G protein. Thus, under some conditions, GCR1 appears able to act independently of the heterotrimer in regulating seed germination [22].

Seeds of the rice dwarf1 (d1) mutant, a null mutant [19*] of the rice Gα subunit, RGA1, exhibit a morphological phenotype consisting of short, round grains [30,31]. Observations in rice are also consistent with a role for G proteins in GA-based signaling pathways and the control of transcription in the seed. d1 mutants exhibit reduced GA induction of a-amylase gene expression and enzyme activity in their aleurone cells and reduced expression of the GA-induced genes OsGAMYB and GACa$^{2+}$ ATPase [32]. Gα may also be a component of BR signaling in rice because BL-stimulated expression of a novel BL-enhanced gene is weaker in d1 mutants than in wild-type seedlings [33]. Ueguchi-Tanaka et al. [32] suggest that there may be two separate GA-signaling pathways in rice, with either high or low sensitivity to GA, and that RGA1 may mediate the former pathway. Both this model and the 'GPA1 modulation' model described above [2,32] are consistent with the current data from both *Arabidopsis* and rice. Hence, additional experimentation, including determination of the ABA sensitivity of d1 seeds, will be required to distinguish between these two possibilities.

G-Protein Signaling in Roots

Root growth and architecture involves a balance between cell production in the apical and lateral root meristems and the subsequent elongation of those cells. One advantage of the root as a model system for development is that it is possible to measure rates of cell production and elongation as well as the number of lateral root primordial quite precisely, thereby making it possible to quantify exactly what has changed in the roots of loss- and gain-of function G-protein mutants. The formation of lateral root meristems originates from a set of founder cells that differs from that used to form the primary meristem [34,35]. Therefore, it would not be surprising if the molecular mechanisms that underlie the initiation of lateral and primary root meristems were different. Studies on root meristem formation and maintenance using G-protein mutants are beginning to reveal these mechanistic differences.

Primary Root

The primary root growth of wild-type plants and that of gpa1 and gcr1 single mutant seedlings appears to be identical in the absence of exogenous hormone treatment [3, 8]. By contrast, rgs1 mutants have longer primary roots because of their increased cell production rate in the primary root meristem [23]. rgs1 cells, which lack GAP activity, are predicted to have a greater steady-state pool of activated Gα. This prediction is consistent with the observation that the expression of a transgene that encodes GPA1$^{QL}$ also causes accelerated cell production by the primary root meristem [23]. This suggests that Gα plays a role in modulating cell division in the primary root meristem. The lack of a large effect of the gpa1 null mutation on primary root growth suggests that the type of modulation that GPA1 exerts may be an increase over a basal state, a state that does not require Gα.

In response to exogenous treatment with plant growth regulators such as ABA and auxin, primary root elongation is retarded and/or the direction of primary root growth changes. The primary root elongation of gpa1, agb1, or gcr1 single mutants, as well as of double and triple combinations of these mutants, is more sensitive to inhibition by ABA than that of wild-type plants ([8]; S Pandey, S M Assmann, unpublished). However, the auxin inhibition of primary root length in gpa1 and agb1 mutants is the same as that in wild-type plants [3], indicating that the dependency of growth inhibition on G proteins differs depending on the hormonal stimulus.

Lateral and Adventitious Roots

While the growth of the primary root of gpa1 mutants is like that of wild-type plants under many conditions, the number of lateral roots is greatly increased in agb1 mutants and is decreased in gpa1 mutants [3**]. Opposite to its inhibitory effect on the primary root, auxin is a key activator of lateral root initiation [36]. In the presence of auxin, agb1 plants form more lateral roots, whereas gpa1 plants form fewer lateral roots, compared to wild-type plants [3*]. As is expected if the auxin-induced phenotype for the proliferation of lateral roots is AGB1-dependent, ectopic expression of GPA1 (which is expected to sequester AGB1 into the heterotrimeric complex) also yields an agb1-like phenotype. The expression of GPA1$^{QL}$ has no effect on this phenotype, a finding that is inconsistent with GPA1 acting as a positive modulator of cell division in the lateral root meristem. Thus, Ullah et al. [3**] propose that free Gβγ directly attenuates auxin-induced cell division in lateral roots, as opposed to Gα acting to stimulate this process.

G-Protein Signaling in Shoots

As for seed germination and root development, several differences have been observed between G-protein-component mutants and wild-type plants during the development of above-ground organs in seedlings and mature plants [10-12].

When grown in darkness, gpa1 and agb1 seedlings have shorter hypocotyls than wild-type plants because of a reduction in cell number, and these seedlings exhibit partially opened hooks [1,3**,37]. These phenotypes were also observed in gcr1 gpa1 double, agb1 gcr1 double, and agb1 gpa1 gcr1 triple mutants [22]. By contrast, rgs1 mutant seedlings have a longer etiolated hypocotyl as a result of increased cell elongation. This mutant phenotype is similar to that observed in plants that express GPA1$^{QL}$, consistent with the premise that, in plants as in animals, RGS proteins oppose Gα activation [22].

When grown in light, gpa1 and agb1 mutants have rounded rosette leaves [1]. The round-leaf phenotype is also found in *Arabidopsis* gcr1 gpa1 and agb1 gcr1 double mutants and agb1 gcr1 gpa1 triple mutants [22]. Because gcr1 single mutants have wild-type phenotypes for both hypocotyl and rosette-leaf development, GCR1 may not act as the GPCR that is responsible for control of these developmental pathways [22].

The rice Gα (d1) mutants also exhibit an altered shoot morphology, consisting of broad, dark green leaves and compact panicles [5,30,31,32,38]. One notable contrast between *Arabidopsis* and rice Gα mutants, however, is that the rice mutants are dwarf but the *Arabidopsis* mutants are not. Dwarf phenotypes are often associated with GA insensitivity, and GA induction of internode elongation is significantly reduced in the d1 mutants [31]. However, the GA responsiveness of the elongation of the second leaf sheath is similar in d1 mutants and wild-type plants [32]. This selective impairment of GA signaling in d1 mutants suggests cell specificity in GA response, with some pathways being only marginally dependent on Gα.

During the reproductive phase of plant development, agb1-1 mutants have a floral phenotype consisting of shorter flowers and thicker siliques, but this phenotype is not shared by gpa1 mutants [1,3,39]. Constitutive overexpression of GPA1 reduces silique length, producing a phenotype that is similar to that of agb1. This evidence is consistent with the idea that silique length is controlled by released Gbg [3]. gpa1 sepals and pedicels are longer, whereas agb1 sepals are shorter, than those of wild-type plants [3**], findings that are again consistent with a Gβγ-dependent pathway. Transformants that overexpress GCR1 flower earlier [29], but gcr1 null mutants typically do not flower later, than wild-type plants [22].

Stress Responses

G proteins are implicated in several stress-signaling pathways in plants. In mature leaves, G proteins transmit signals to molecules, including small GTPases, ion channels, and phospholipases, that are effectors in the responses to various biotic and abiotic stress conditions, including pathogen elicitation, ozone treatment and water deficit.

There are no reports as yet on pathogen signaling in *Arabidopsis* G-protein mutants, but some defense signaling pathways in rice appear to rely on RGA1. Upon infection with a virulent strain of bacterial blight (*Xanthomonas oryzae* pv. *Oryzae* [Xoo]), symptom development in d1 mutants is more severe than that in wild-type plants [7]. By contrast, infection with virulent strains of rice blast fungus (*Magnaporthe grisea*) produces identical lesions in d1 mutants and wild-type plants. d1 mutants exhibit a highly reduced response, however, upon inoculation with avirulent rice blast [5,7]. Expression of a constitutively active OsRac1 in d1 mutants restores defense signaling and resistance, suggesting that RGA1 functions upstream of this small GTPase [5]. Yet, in a d1 mutant cell line treated with the oligosaccharide elicitor chitin, the elicitation of defense responses such as extracellular alkalinization, generation of reactive oxygen species, phytoalexin accumulation and the induction of specific genes does not differ from that of wild-type cells [40,41]. Taken together, these studies indicate that the extent of G-protein coupling of responses to both avirulent and virulent pathogens is pathogen- and elicitor-specific.

Like pathogen infection, exposure to high ozone ($O_3$) levels results in foliar lesions, and $O_3$ responses share signaling pathways and gene expression patterns with the hypersensitive response [42]. gpa1 null mutants and the double mutant gpa1-4 agb1-2 respond differently to $O_3$ compared to wild-type plants, and to gcr1 and rgs1 single mutants. The major difference observed among these mutant genotypes is an $O_3$-resistant phenotype of the gpa1 lines, indicated by lack of leaf curling in response to $O_3$ [6].

One of the phenomena commonly observed following $O_3$ exposure is a reduction in stomatal apertures [43], a response that is also evoked by ABA. gpa1 mutants exhibit reduced $O_3$ sensitivity at the whole-leaf level. At the single (guard)-cell level, gpa1 mutants also exhibit aspects of ABA insensitivity, including reduced ABA inhibition of guard cell inward $K^+$ channels and altered ABA-promotion of slow anion currents [4]. Recently, the lipid metabolite, sphingosine-1-phosphate (S1P), has been described as a secondary messenger for ABA responses [44,45]. The guard cells of gpa1 mutants show insensitivity to inhibition of stomatal opening by either ABA or S1P. However, ABA still induces wild-type levels of stomatal closure in gpa1 [4], whereas stomatal closure in this genotype is insensitive to S1P. This difference implies that the S1P response is obligatorily mediated by GPA1, whereas there is a parallel or backup pathway for ABA induction of stomatal closure that is independent of GPA1 [45].

gcr1 mutant guard cells exhibit hypersensitivity to ABA and S1P in both inhibition of stomatal opening and promotion of stomatal closure [8], which would be unexpected if GCR1 were to transmit the ABA signal to GPA1. Pandey and Assmann [8] therefore proposed that GCR1 acts as a negative regulator of GPA1-mediated ABA responses in guard cells. Consistent with this phenomenon, gcr1 mutant plants have higher expression levels of some known drought- and ABA-regulated genes after exogenous ABA treatment and exhibit improved recovery following drought stress [8**].

Many enzymes, including phosphatidylinositol-phospholipase Cs (PLCs; reviewed in [46]) and phospholipase Ds (PLDs; [47,48]), act as effectors of the ABA response during the regulation of stomatal aperture. These phospholipases also have been identified recently, albeit not yet in guard cells, as intracellular effectors of G protein signaling. For instance, using tobacco BY2 cells that overexpressed GCR1, Apone et al. [49] concluded that GCR1 regulates DNA synthesis through activation of PLC. In *Arabidopsis*, PLDα1 directly binds GPA1 via a motif similar to the DRY motif that is present in many mammalian GPCRs [50]. Binding inhibits PLDα1 activity and is relieved upon GTP addition, suggesting that, in vivo, G protein activation leads to the activation of PLDα1 [50]. Thus, it will be of interest to assess PLC and PLD activity in guard cells in which the levels of G-protein components are altered.

Conclusions: with Few G-Protein Complexes in Plants, GPCRs and Effectors Must Specify Signal Transduction As is evident from the phenotypes described in this review, numerous processes at all stages of plant development are modulated by heterotrimeric G proteins. Many of these phenotypes appear upon null mutation of the Gα subunit genes GPA1 or RGA1, implying dependency upon Gα coupling to downstream effectors. However, some phenotypes, notably lateral root proliferation and altered silique morphology, are present in agb1 mutants but are either absent or opposite in gpa1 mutants, implying a dependency on Gβγ-coupled signaling. But is that the whole story? Plausibly, the different phenotypes of gpa1 and agb1 mutants could reflect differences in the relative levels of the released subunits from the heterotrimeric complex, different fluxes of signaling through Gα (as opposed to Gβγ) in the different cell types or organs, and/or a different relative balance in positive or negative feedback. To sort out these issues, it will be necessary to determine the effect on a given trait of quantitatively altered ratios of Gα to Gβγ, rather than of the two extremes of ratios of 0 or ∞ that are created by single null mutations. Given the plethora of G-protein-related phenotypes in combination with the dearth of heterotrimeric G-protein subunits in plant genomes, one might well predict that plants will be found to have evolved novel and abundant mechanisms for coupling G protein components with downstream effector molecules.

In *Arabidopsis*, seeds and light-grown gpa1 seedlings show increased sensitivities to ABA and sucrose together with decreased sensitivities to BL [2,27*] suggesting that identical G-protein-based signaling pathways may operate in seed germination and early seedling development. In mature rosette leaves, however, gpa1 guard cells exhibit reduced rather than enhanced sensitivity to ABA. In rice, internode sensitivity to GA is strongly reduced in d1 mutants, yet GA-regulation of leaf-sheath elongation is scarcely affected. These differential sensitivities indicate that the roles of GPA1 must be cell- and tissue-specific, presumably reflecting cell- and tissue-specific effectors and/or GPCRs. Cell-specific mechanisms for G-protein-coupled signaling have precedent in animal systems (e.g. [51]).

By parallel reasoning, one might expect a proliferation of cell-specific GPCRs in plants. However, if this is true, the plant GPCRs must be defined by functionality rather than by sequence similarity; GCR1 is the sole candidate GPCR to be identified in *Arabidopsis* on the basis of homology criteria and its sequence similarity to known GPCRs is limited. The observations that GCR1 is not implicated in many of the pathways that are affected by mutation of GPA1 and/or AGB1, and that the ABA-related phenotypes of gcr1 mutants are opposite to those of gpa1 mutants, further highlight our lack of knowledge about components that function upstream of plant G-protein heterotrimers. Signals may be transduced either via novel GPCRs or through proteins that transmit signals to G proteins independently of GPCRs [51,52]. Furthermore, plant-specific 'unconventional' G proteins, such as *A. thaliana* Extra Large G Protein1 (XLG1), a protein that has significant similarity to Gα subunits and exhibits GTP-binding capability [11,53], could potentially partner with components of G-protein pathways. Thus, the future is bright for model plant systems such as *Arabidopsis* and rice to contribute new insights regarding this ubiquitous eukaryotic signaling paradigm.

In *Arabidopsis*, GCR1 may positively regulate seed germination by coupling BR promotion of GA-stimulated germination. GCR1 also can act independently of GPA1 and AGB1 in a pathway to regulate GA-stimulated germination [23]. RGS1 antagonizes the activation of GPA1 [23]. Pirin1 may positively regulate seed germination by overcoming the negative effect of ABA or by activating germination-promoting pathways [27*]. In rice, RGA1 may work in a high-sensitivity GA pathway that regulates the induction of $Ca^{2+}$-ATPase and α-amylase, leading to seed germination [32]. RGA1 may also be a component of BR signaling [33]. In addition, there may be an alternative GA pathway that also induces a-amylase but does not involve RGA1 [32]. (b) Cell division/elongation. During seedling growth, GPA1, AGB1 and GCR1 may act in the inhibition of primary root development by ABA art S Pandey, S M Assmann, unpublished). Furthermore, GCR1 negatively regulates ABA-induced gene expression [8]. AGB1 and GPA1 activate cell division in both hypocotyls and leaves [1,2,3,37] whereas RGS1 antagonizes the activation of GPA1 in apical root meristems [23]. Auxin treatment also increases GPA1 transcript levels and decreases AGB1 transcript levels (not shown in figure, [3]). During lateral root formation, AGB1 functions downstream of GPA1 and inhibits auxin-induced cell division, and GPA1 inhibits AGB1 function [3**]. (c) Stress responses. According to the leaf curling phenotype, GPA1 promotes the $O_3$ sensitivity of *Arabidopsis* plants [6]. Drought stress and ABA treatment inhibit stomatal opening and promote stomatal closure. ABA triggers S1P formation, which is coupled by GPA1 to inhibit plasma membrane inwardly rectifying $K^+$ channels and to activate slow anion channels, resulting in the inhibition of stomatal opening and the promotion of stomatal closure [4,45**]. The GPCR-like protein GCR1 directly binds to GPA1 and negatively controls ABA- and S1P-regulation of stomatal apertures [8]. In rice, responses to avirulent rice blast fungus, including the accumulation of transcripts for the small GTPase, OsRac1, are attenuated in the RGA1 mutant d1. OsRac1 acts as a key molecular switch for multiple signaling pathways, such as the production of reactive oxygen species that lead to disease resistance. Expression of constitutively active OsRac1 in the d1 mutant restores defense signaling [5]. In response to virulent strains of bacterial blight, lesions are more severe in the d1 mutant than in wildtype plants [7]. (d) Morphology. In *Arabidopsis*, both GPA1 and AGB1 modulate leaf development and shape [1,39]. gpa1 and agb1 mutants exhibit rounded lamina. AGB1 is also involved in flower and fruit development [1,3**,39]. In agb1, the floral buds at the inflorescence apex are more tightly clustered, the siliques are shorter, and the silique tips are more blunt than those of wildtype plants. In rice, RGA1 modulates plant stature by regulating internode and panicle elongation, and also influences the color of leaf blades and sheaths and grain shape [32].

TABLE 1

Mutant and transgenic lines for Gα, Gβ, GCR1 and RGS 1

| Name/Allele | Ecotype/cultivar | cDNA | Status of transcript/translation product | Phenotype comparison with wild-type ecotypes |
|---|---|---|---|---|
| *Mutant loss of function for Gα subunit in Arabidopsis (A. thaliana)* | | | | Phenotypes of gpa1 mutants |
| gpa1-1 | Ws | T-DNA insertion in 7$^{th}$ intron. Wisconsin KO *Arabidopsis* facility α population | Lacks full-length transcript [1]. | Less sensitive to GA and BL stimulation of germination [1, 2]. More sensitive to the GA biosynthesis inhibitor paclobutrazol [2, 22]. Hypersensitive to ABA and sugar inhibition of germination [2, 27*]. In darkness, partial deetiolation: open hook; shorter hypocotyls caused by reduced cell division [1]. |
| gpa1-2 | Ws | T-DNA insertion in 8$^{th}$ exon. Wisconsin KO *Arabidopsis* facility α population. | Lacks full-length transcript [1]. | Primary root forms fewer lateral root primordia [1]. Less sensitive to auxin promotion of lateral root formation [3**]. Rounded lamina shape [1, 37]. Leaf cells are fewer and larger [1]. Longer sepals and pedicels [1]. Less sensitive to O3 [6]. |
| gpa1-3 | Col-0 | T-DNA insertion in 9$^{th}$ exon. Salk collection. | Lacks full-length transcript [37]. | More water loss [4]. Insensitive to ABA inhibition of stomatal opening [4]. Insensitive to ABA inhibition of inward K$^+$ channels [4]. Insensitive to S1P promotion of stomatal closure [45**]. |
| gpa1-4 | Col-0 | T-DNA insertion in 12$^{th}$ intron. Salk collection | Lacks full-length transcript [37]. | Altered sensitivity to ABA activation of slow anion channels [4]. Insensitive to S1P activation of slow anion channels [45**]. |
| *Mutant loss of function for Gα subunit in rice (Oryza sativa)* | | | | Phenotypes of Daiokoku dwarf1 (d1) mutants (DK22, HO541, CM 1361-1, T65d1, rga1) |
| DK 22 | Nipponbare | Point mutation of G598 to T in 8$^{th}$ exon. | Stop codon generated [31, 40]. Protein null [19*]. | Shorter and rounded grains [30, 31]. Reduced GA and BL stiumlation of gene expression [32, 33]. |
| Ho 541 | Nipponbare | Spontaneous mutant: Deletion of 833 basepairs between 1$^{st}$ exon and intron. | RGA1 transcript null [3-] | Shorter and darker green leaves, more compact particle [5, 30-32, 38]. |
| CM 1361-1 | Kinmaze | Insertion between nucleotides 354-355 | Predicted protein lacks GTP-, effector- and receptor-binding regions [31]. | Shorter internodes - may be due to a decrease in the number of cells per internode [31]. Reduced GA stimulation of internode growth [32]. Normal GA stimulation of second leaf sheath elongation [32]. |
| T65d1 | Taichung 65 | Deletion of nucleotides 1003-1004. | Stop condon generated before third effector-binding region [32]. | Reduced hypersensitive response to infection by rice blast fungus [5]. |
| rga1 | Nipponbare | Antisense suppression. | RGA1 transcript null line [31] | Increased sensitivity to infection by virulent strain of bacterial blight [7]. |
| HO 532 HO 533 HO 537 HO 538 HO 552 | Nipponbare | Spontaneous mutants. | [30] | Not used for phenotypic analysis. |

TABLE 1-continued

Mutant and transgenic lines for Gα, Gβ, GCR1 and RGS 1

| Name/Allele | Ecotype/cultivar | cDNA | Status of transcript/translation product | Phenotype comparison with wild-type ecotypes |
|---|---|---|---|---|
| FL2 | Nipponbare | Marker line derived from HO 538. | [30] | Not used for phenotypic analysis. |
| ID 1 | Shiokari | Deletion of nucleotides 1003-1004. | [31] | Not used for phenotypic analysis. |
| CM392; 1729; 248; 723; 1232 | Kinmaze | Induced by N-methyl-N-nitrosourea. | [5, 30] | Not used for phenotypic analysis. |
| DKT 1 | Taichung 65 | Point mutation of A1075 to T. | [31] | Not used for phenotypic analysis. |
| DK 2 | Taichung 65 | Deletion betwween nucleotides 932-979 | Predicted to lack GTP-binding region [31]. | Not used for phenotypic analysis. |

Mutant gain of function for Gα subunit in *Arabidopsis*

| Name/Allele | Ecotype/cultivar | cDNA | Status of transcript/translation product | Phenotypes of GPA1 overexpressors |
|---|---|---|---|---|
| Q222L or GPA1* | Col | 35S promoter::point mutation A1264 to T derived from GPA1 cDNA. | Mutation disables GTPase activity, leading to constitutively active Gα [1, 3**, 37]. | No effect on auxin-induced cell divison in lateral roots [3**]. No auxin effect on hypocotyl length [3**]. |
| GPA1<sup>a</sup> | Ws | 35S promoter::constitutive form of GPA1 cDNA | Overexpression of constitutively active Gα (GPA1<sup>QL</sup>) [23**]. | Increased hypocotyl length caused by increased cell elongation [23**]. Longer primary roots caused by increased cell production [23**]. |
| cGα | Ws | DEX inducible promoter::constitutive form of GPA1 cDNA. | Overexpression of constitutively active Gα (GPA1<sup>QL</sup>) [54]. | Under low light condition, shorter hypocotyls are caused by a reduction of cell elongation, also smaller cotyledons and increased stomatal density in hypocotyl [54]. |
| wGα | Ws | DEX inducible promoter:: GPA1 cDNA. | Overexpression of full-length GPA1 protein [54]. | Under low light condition, shorter hypocotyls are caused by a reduction of cell elongation, also smaller cotyledons and increased stomatal density in hypocotyl [54]. |
| gpa1 (GPA1) | Col-0 | DEX inducible promoter:: GPA1 cDNA. | Complementation in gpa1 background [3**, 37]. | Hypersensitive to GA stimulation of germination [2]. In darkness, shorter hypocotyls [37]. Hypocotyl hypersensitive to auxin-induced adventitious root formation [3**]. |
| 35S::GPA1-GFP | Col | 35S promoter::GPA1 cDNA fused with GFP. | Overexpression of fluorescent GPA1 [23**]. | Mimics agb1-2 lateral root phenotype: more lateral roots [3**]. |
| GOX | Col | DEX inducible promoter:: GPA1 cDNA: | Overexpression of GPA1 [2, 37]. | Shorter cell cycle [1]. |
| GOX1 | Tobacco cells *Nicotiana tabaccum* cv. BY2 | DEX inducible promoter:: GPA1 cDNA. | Transformed BY2 cells overexpressing GPA1 [1, 49]. | Higher PtdIns-PLC activity [49]. Higher Ins(1, 4, 5)P$_3$ content [49]. |

Mutant gain of function for Gα subunit in rice

| Name/Allele | Ecotype/cultivar | cDNA | Status of transcript/translation product | Phenotypes of RGA1 overexpressors |
|---|---|---|---|---|
| QL/d1 or Q223L | Nipponbare | 35S promoter:: point mutation Q223 to L derived from RGA 1 cDNA. | Expression of constitutively active Gα in d1 background [19*]. | Active form GTP-Gα presents fee from Gβ or Gγ subunits [9*]. |

TABLE 1-continued

Mutant and transgenic lines for Gα, Gβ, GCR1 and RGS 1

| Name/Allele | Ecotype/cultivar | cDNA | Status of transcript/translation product | Phenotype comparison with wild-type ecotypes |
|---|---|---|---|---|
| | | Mutant loss of function for Gβ subunit in *Arabidopsis* | | Phenotypes of agb1 mutants |
| agb1-1 or elk4 | Col | Ethyl methanesulfonic acid mutagerized. Missense mutation: failure to splice out the 1st intron. | Mutant transcript slightly larger because of splicing failure. Stop condon generated [39]. | Less sensitive to GA and BR stimulation of germination [22]. More sensitive to the GA biosynthesis inhibitor paclobutrazol [2, 22]. Hypersensitive to sugar inhibition of germination [2]. In darkness, partial de-etiolation: open hook; shorter hypocotyls caused by reduced cell division [1]. Hypocotyl hypersensitive to auxin-induced adventitious root formation [3**]. Primary root forms more lateral root primordia [3**]. |
| agb1-2 | Col-0 | T-DNA insertion in 4th exon. Salk collection. | Lacks full-length transcript [3**]. | More sensitive to auxin promotoino of lateral root formation [3**]. Rounded lamina shape and presence of islands of small cells that create a crinkly surface [3**, 39]. Shorter flowers and sepals [39]. Shorter and thicker siliques [39]. |
| | | Mutant gain of function for Gβ subunit in *Arabidopsis* | | Phenotypes of AGB1 |
| agb1-1 (AGB1) | Col | Transformation with genomic fragment containing AGB1 gene and promoter. | Complementation in agb1-1 background [39]. | |
| agb1-1 (AGB1) BOX | Col-0 | DEX inducible promoter::AGB1 cDNA. | Complementation in agb1-2 background [3**]. Overexpression of AGB1 [3**, 37]. | Decreased auxin-induced lateral root formation relative to agb1 [3**]. |
| | Col-0 | DEX inducible promoter::AGB1 cDNA. | | |
| | | Mutant loss of function for GCR 1 in *Arabidopsis* | | Phenotypes of gcr1 mutants |
| gcr1-1 | Col-0 | T-DNA insertion in 8th intron. Salk collection. | Lacks full-length transcript [22]. | Less sensitive to GA and BR stimulation of germination [22]. Hypersensitive to ABA inhibition of germination [8**]. Hypersensitive to the GA inhibitor paclobutrazol [22]. Increased ABA promotion of ABA-regulated gene expression [8**]. Increased resistance to drought stress [8**]. Hypersensitive to ABA and S1P inhibition of stomatal opening [8**]. Hypersensitive to ABA and S1P promotion of stomatal closure [8**]. Flowers slightly earlier [22]. |
| gcr1-2 | Col-0 | T-DNA insertion in 6th exon. Salk collection. | Lacks full-length transcript [22]. | |
| gcr1-3 | Ws | T-DNA insertion in 2nd intron. Wisconsin *Arabidopsis* KO facility BASTA population. | Lacks full-length transcript[8**]. | |
| gcr1-4 | Col | T-DNA insertion in 3rd intron. SAIL collection of TMRI. | Lacks full-length transcript [8**]. | |
| | | Mutant gain of function for GCR1 in *Arabidopsis* | | Phenotypes of GCR1 overexpressors |
| gcr1-3 (GCR1) | Ws | DEX inducible promoter::GCR1 cDNA fused with FLAG tag. | Expression in gcr1-3 background [8**]. | GCR1-FLAG immunoprecipitates with GPA1 [8**]. |
| 35S::GCR1-GFP | Col | 35S promoter::GCR1 cDNA fused with GFP. | Overexpression of fluorescent GCR1 [22] | |

TABLE 1-continued

Mutant and transgenic lines for Gα, Gβ, GCR1 and RGS 1

| Name/Allele | Ecotype/cultivar | cDNA | Status of transcript/translation product | Phenotype comparison with wild-type ecotypes |
|---|---|---|---|---|
| GCR1-overexpressing lines | Col | 35S promoter::GCR1 cDNA | Overexpression of GCR1 [29]. | Lacks seed dormancy [29]. Increawsed expression of germination associated genes [29]. Early flowering [29] |
| GCR1-overexpressing BY2 cells | Tobacco cells Nicotiana tabaccum cv. BY2. | 5S promoter::GCR1 cDNA | Transformed BY2 cells overexpressing GCR1 [29, 49]. | Increased DNA synthesis [29]. Higher PtdIns-PLC activity [49]. Higher Ins(1, 3, 5)$P_3$ content [49]. |
| Mutant loss of function for RGS1 in *Arabidopsis* | | | | Phenotypes of rgs1 mutants |
| rgs1-1 | Col-0 | T-DNA insertion in 6$^{th}$ intron. Salk collection. | Lacks full-length transcript [23**]. | Mimics GPA1$^{QL}$ phenotype under darkness: longer hypocotyls caused by increased cell elongation [23**]. Longer primary roots caused by increased cell production in light [23**]. |
| rgs1-2 | Col-0 | T-DNA insertion in 9$^{th}$ intron. Salk collection. | Lacks full-length transcript [23**]. | Insensitive to 6% D-glucose inhibition of seedling growth [23**]. |
| Mutant gain of function for RGS1 in *Arabidopsis* | | | | Phenotypes of RGS1 overexpressors |
| 35S::RGS1-GFP | Col | 5S promoter::RGS1 cDNA fused with GFP | Overexpression of fluorescent RGS1 [23**]. | Mimics gpa1 mutant hypocotyl phenotype under darkness: shorter hypocotyl [23**]. |
| ROX | Col-0 | DEX inducible promoter::RGS1 open reading frame | Overexpression of full length RGS1 protein [23**]. | Hypersensitive to 6% D-glucose inhibition of seedling growth [23**]. |
| Loss of function double/triple mutants in *Arabidopsis* | | | | Phenotypes double/triple mutants |
| gpa1-4 agb1-2 | Col-0 | Cross between gpa1-4 and agb1-2. | [37] | Less sensitive to GA and BR stimulation of germination (same sensitivity as agb1 mutant [22]). Shorter hypocotyls and partially opened hooks [37]. Rounded lamina shape [22]. Less sensitive to $O_3$ [6]. |
| gcr1-2 gpa1-4 | Col-0 | Cross between gcr1-2 and gpa1-4 | [22, 37] | Less sensitive to GA and BR stimulation of germination (additive or synergistic effect of mutations [22]). gpa1 phenotype under darkness: shorter hypocotyl and partially opened hook [22]. gpa1 leaf morphology: rounded lamina shape [22]. Less sensitive to GA and BR stimulation of germination (additive or synergistic effect of mutations [22]). |
| agb1-2 gcr1-2 | Col-0 | Cross between gpa1-4 agb1-2 and gcr1-2. | [22] | agb1 phenotype under darkness: shorter hypocotyl and partially opened hooks [22]. agb1 leaf morphology: rounded lamina shape [22]. |
| agb1-2 gcr1-2 gpa1-4 | Col-0 | Cross between gpa1-4 agb1-2 and gcr1-2. | [22] | Less sensitive to GA and BR stimulation of germination (additive or synergistic effect of mutations [22]). gpa1 and agb1 phenotype under darkness: shorter hypocotyl and partially opened hooks [22]. |

TABLE 1-continued

Mutant and transgenic lines for Gα, Gβ, GCR1 and RGS 1

| Name/Allele | Ecotype/cultivar | cDNA | Status of transcript/translation product | Phenotype comparison with wild-type ecotypes |
|---|---|---|---|---|
| | | | | gpa1 and agb1 phenotype under darkness: shorter hypocotyl and partially opened hooks [22]. |
| agb1-1 er-105 | Col | Cross between agb1-1 and receptor-like kinase erecta mutant, er-105 | [39] | gpa1 and agb1 leaf morphology: rounded lamina shape [22]. Shorter petiole, shorter lamina than either agb1 or er105 single mutant, suggesting that ER and AGB1 function in parallel pathways controlling these characteristics [39]. |
| D1 slr | Nipponbare | Cross between d1 and GA insensitive mutant slr. | [32] | SLR is epistatic to D1 supporting RGA1 involvement in GA signaling [32]. |

35S, cauliflower mosaic virus 35S promoter;
BOX, AGB1 overexpressing lines;
Col, Columbia;
DEX, dexamethansone;
elk4, erecta like 4 mutant;
er-105, receptor-like kinase erecta mutant;
GFP, green fluorescent protein;
GOX, GPA1 overexpressing lines;
Ins(1,4,5)P$_3$, inositol-1,4,5-trisphosphate;
PtdIns-PLC, phosphatidylinositol-phospholipase C;
ROX, RGS1 overexpressing lines;
SAIL, Syngenta *Arabidopsis* Insertion Library;
slr, slender rice mutant;
TMRI, Torrey Mesa Research Institute;
Ws, Wassilewskija.

REFERENCES

1. Ullah H, Chen J G, Young J C, Im K H, Sussman M R, Jones A M: Modulation of cell proliferation by heterotrimeric G protein in *Arabidopsis*. Science 2001, 292:2066-2069.
2. Ullah H, Chen J G, Wang S, Jones A M: Role of a heterotrimeric G protein in regulation of *Arabidopsis* seed germination. *Plant Physiol* 2002, 129:897-907.
3. Ullah H, Chen J G, Temple B, Boyes D C, Alonso J M, Davis K R, Ecker J R, Jones A M: The β-subunit of the *Arabidopsis* G protein negatively regulates auxin-induced cell division and affects multiple developmental processes. *Plant Cell* 2003, 15:393-409.
4. Wang X Q, Ullah H, Jones A M, Assmann S M: G protein regulation of ion channels and abscisic acid signaling in *Arabidopsis* guard cells. *Science* 2001, 292:2070-2072.
5. Suharsono U, Fujisawa Y, Kawasaki T, Iwasaki Y, Satoh H, Shimamoto K: The heterotrimeric G protein α subunit acts upstream of the small GTPase Rac in disease resistance of rice. *Proc Natl Acad Sci USA* 2002, 99:13307-13312.
6. Booker F L, Burkey K O, Overmyer K, Jones A M: Differential response of G-protein *Arabidopsis thaliana* mutants to ozone. *New Phytol* 2004, 162:633-641.
7. Komatsu S, Yang G, Hayashi N, Kaku H, Umemura K, Iwasaki Y: Alterations by a defect in a rice G protein α subunit in probenazole and pathogen-induced responses. *Plant Cell Environ* 2004, 27:947-957.
8. Pandey S, Assmann S M: The *Arabidopsis* putative G protein coupled receptor GCR1 interacts with the G protein α subunit GPA1 and regulates abscisic acid signaling. *Plant Cell* 2004, 16:1616-1632.
9. Ma H: GTP-binding proteins in plants: new members of an old family. *Plant Mol Biol* 1994, 26:1611-1636.
10. Fujisawa Y, Kato H, Iwasaki Y: Structure and function of heterotrimeric G proteins in plants. *Plant Cell Physiol* 2001, 42:789-794.
11. Assmann S M: Heterotrimeric and unconventional GTP binding proteins in plant cell signaling. *Plant Cell* 2002, 14:S355-S373.
12. Jones A M: G-protein-coupled signaling in *Arabidopsis*. *Curr Opin Plant Biol* 2002, 5:402-407.
13. Jones A M, Assmann S M: Plants: the latest model system for G-protein research. *EMBO Rep* 2004, 5:572-578.
14. Ma H, Yanofsky M F, Meyerowitz E M: Molecular cloning and characterization of GPA1, a G protein α subunit gene from *Arabidopsis thaliana*. *Proc Natl Acad Sci USA* 1990, 87:3821-3825.
15. Ishikawa A, Tsubouchi H, Iwasaki Y, Asahi T: Molecular cloning and characterization of a cDNA for the α subunit of a G protein from rice. *Plant Cell Physiol* 1995, 36:353-359.
16. Weiss C A, Garnaat C W, Mukai K, Hu Y, Ma H: Isolation of cDNAs encoding guanine nucleotide-binding protein β-subunit homologues from maize (ZGB1) and *Arabidopsis* (AGB1). *Proc Natl Acad Sci USA* 1994, 91:9554-9558.
17. Ishikawa A, Iwasaki Y, Asahi T: Molecular cloning and characterization of a cDNA for the β subunit of a G protein from rice. *Plant Cell Physiol* 1996, 27:223-228.
18. Mason M G, Botella J R: Completing the heterotrimer: isolation and characterization of an *Arabidopsis thaliana* G protein γ-subunit cDNA. *Proc Natl Acad Sci USA* 2000, 97:14784-14788.
19*. Kato C, Mizutani T, Tamaki H, Kumagai H, Kamiya T, Hirobe A, Fujisawa Y, Kato H, Iwasaki Y: Characterization of heterotrimeric G protein complexes in rice plasma membrane. *Plant J* 2004, 38:320-331.
20. Mason M G, Botella J R: Isolation of a novel G-protein γ-subunit from *Arabidopsis thaliana* and its interaction with Gβ. *Biochim Biophys Acta* 2001, 1520:147-153.
21. Josefsson L G, Rask L: Cloning of a putative G-protein-coupled receptor from *Arabidopsis thaliana*. *Eur J Biochem* 1997, 249:415-420.
22. Chen J G, Pandey S, Huang J, Alonso J M, Ecker J R, Assmann S M, Jones A M: GCR1 can act independently of heterotrimeric G-protein in response to brassinosteroids and gibberellins in *Arabidopsis* seed germination. *Plant Physiol* 2004, 135:907-915.
23. Chen J G, Willard F S, Huang J, Liang J, Chasse S A, Jones A M, Siderovski D P: A seven-transmembrane RGS protein that modulates plant cell proliferation. *Science* 2003, 301:1728-1731.
24. Iwasaki Y, Kato T, Kaidoh T, Ishikawa A, Asahi T: Characterization of the putative a subunit of a heterotrimeric G protein in rice. *Plant Mol Biol* 1997, 34:563-572.
25. Weiss C A, White E, Huang H, Ma H: The G protein alpha subunit (GPα1) is associated with the ER and the plasma membrane in meristematic cells of *Arabidopsis* and cauliflower. *FEBS Lett* 1997, 407:361-367.
26. Gazzarrini S, McCourt P: Cross-talk in plant hormone signaling: what *Arabidopsis* mutants are telling us. *Ann Bot* 2003, 91:605-612.
27*. Lapik Y R, Kaufman L S: The *Arabidopsis* cupin domain protein AtPirin1 interacts with the G protein α subunit GPA1 and regulates seed germination and early seedling development. *Plant Cell* 2003, 15:1578-1590.
28. Ma H: Plant G proteins: the different faces of GPA1. *Curr Biol* 2001, 21:R869-R871.
29. Colucci G, Apone F, Alyeshmerni N, Chalmers D, Chrispeels M J: GCR1, the putative *Arabidopsis* G protein-coupled receptor gene is cell cycle-regulated, and its overexpression abolishes seed dormancy and shortens time to flowering. *Proc Natl Acad Sci USA* 2002, 99:4736-4741.
30. Ashikari M, Wu J, Yano M, Sasaki T, Yoshimura A: Rice gibberellin-insensitive dwarf mutant gene Dwarf 1 encodes the α-subunit of GTP-binding protein. *Proc Natl Acad Sci USA* 1999, 96:10284-10289.
31. Fujisawa Y, Kato T, Ohki S, Ishikawa A, Kitano H, Sasaki T, Asahi T, Iwasaki Y: Suppression of the heterotrimeric G protein causes abnormal morphology, including dwarfism, in rice. *Proc Natl Acad Sci USA* 1999, 96:7575-7580.
32. Ueguchi-Tanaka M, Fujisawa Y, Kobayashi M, Ashikari M, Iwasaki Y, Kitano H, Matsuoka M: Rice dwarf mutant d1, which is defective in the α subunit of the heterotrimeric G protein, affects gibberellin signal transduction. *Proc Natl Acad Sci USA* 2000, 97:11638-11643.
33. Yang G, Matsuoka M, Iwasaki Y, Komatsu S: A novel brassinolide-enhanced gene identified by cDNA microarray is involved in the growth of rice. *Plant Mol Biol* 2003, 52:843-854.
34. Malamy J E, Benfey P N: Organization and cell differentiation in lateral roots of *Arabidopsis thaliana*. *Development* 1997, 124:33-44.
35. Mayer U, Buttner G, Jürgens G: Apical-basal pattern formation in the *Arabidopsis* embryo: studies on the role of the gnom gene. Development 1993, 117:149-162.

36. Casimiro I, Beeckman T, Graham N, Bhalerao R, Zhang H, Casero P, Sandberg G, Bennett M J: Dissecting *Arabidopsis* lateral root development. *Trends Plant Sci* 2003, 8:165-171.

37. Jones A M, Ecker J R, Chen J G: A reevaluation of the role of the heterotrimeric G protein in coupling light responses in *Arabidopsis*. *Plant Physiol* 2003, 131:1623-1627.

38. Iwasaki Y, Fujisawa Y, Kato H: Function of heterotrimeric G protein in gibberellin signaling. *J Plant Growth Regul* 2002, 22:126-133.

39. Lease K A, Wen J, Li J, Doke J T, Liscum E, Walker J C: A mutant *Arabidopsis* heterotrimeric G-protein β subunit affects leaf, flower, and fruit development. *Plant Cell* 2001, 13:2631-2641.

40. Tsukada K, Ishizaka M, Fujisawa Y, Iwasaki Y, Yamaguchi T, Minami E, Shibuya N: Rice receptor for chitin oligosaccharide elicitor does not couple to heterotrimeric G-protein: elicitor responses of suspension cultured rice cells from Daikoku dwarf (d1) mutants lacking a functional G-protein α subunit. *Physiol Plant* 2002, 116:373-382.

41. Day R B, Tanabe S, Koshioka M, Mitsui T, Itoh H, Ueguchi-Tanaka M, Matsuoka M, Kaku H, Shibuya N, Minami E: Two rice GRAS family genes responsive to N-acetylchitooligosaccharide elicitor are induced by phytoactive gibberellins: evidence for cross-talk between elicitor and gibberellin signaling in rice cells. *Plant Mol Biol* 2004, 54:261-272.

42. Tamaoki M, Nakajima N, Kubo A, Aono M, Matsuyama T, Saji H: Transcriptome analysis of $O_3$-exposed *Arabidopsis* reveals that multiple signal pathways act mutually antagonistically to induce gene expression. *Plant Mol Biol* 2003, 53:443-456.

43. Mansfield T A: Stomata and plant water relations: does air pollution create problems? *Environ Pollut* 1998, 101:1-11.

44. Ng C K, Carr K, McAinsh M R, Powell B, Hetherington A M: Drought-induced guard cell signal transduction involves sphingosine-1-phosphate. *Nature* 2001, 410:596-599.

45. Coursol S, Fan L M, Le Stunff H, Spiegel S, Gilroy S, Assmann S M: Sphingolipid signalling in *Arabidopsis* guard cells involves heterotrimeric G proteins. *Nature* 2003, 423: 651-654.

46. Fan L M, Zhao Z, Assmann S M: Guard cells: a dynamic signaling model. *Curr Opin Plant Biol* 2004, 7:537-546.

47. Jacob T, Ritchie S, Assmann S M, Gilroy S: Abscisic acid signal transduction in guard cells is mediated by phospholipase D activity. *Proc Natl Acad Sci USA* 1999, 96:12192-12197.

48. Zhang W, Qin C, Zhao J, Wang X: Phospholipase Da1-derived phosphatidic acid interacts with ABI1 phosphatase 2C and regulates abscisic acid signaling. *Proc Natl Acad Sci USA* 2004, 101:9508-9513.

49. Apone F, Alyeshmerni N, Wiens K, Chalmers D, Chrispeels M J, Colucci G: The G-protein-coupled receptor GCR1 regulates DNA synthesis through activation of phosphatidylinositol specific phospholipase C. *Plant Physiol* 2003, 133:571-579.

50. Zhao J, Wang X: *Arabidopsis* phospholipase Da1 interacts with the heterotrimeric G-protein α-subunit through a motif analogous to the DRY motif in G-protein-coupled receptors. *J Biol Chem* 2004, 279:1794-1800.

51. Schaefer M, Petronczki M, Dorner D, Forte M, Knoblich J A: Heterotrimeric G proteins direct two modes of asymmetric cell division in the *Drosophila* nervous system. *Cell* 2001, 107:183-194.

52. Manning D R: Evidence mounts for receptor-independent activation of heterotrimeric G proteins normally in vivo: positioning of the mitotic spindle in *C. elegans*. *Sci STKE* 2003, 2003:pe35.

53. Lee Y R, Assmann S M: *Arabidopsis thaliana* 'extra-large GTP-binding protein' (AtXLG1): a new class of G-protein. *Plant Mol Biol* 1999, 40:55-64.

54. Okamoto H, Matsui M, Deng X W: Overexpression of the heterotrimeric G-protein α-subunit enhances phytochromemediated inhibition of hypocotyl elongation in *Arabidopsis*. *Plant Cell* 2001, 13:1639-1652.

EXAMPLE 3

Heterotrimeric G Proteins Regulate Reproductive Trait Plasticity in Response to Water Availability Summary Phenotypic plasticity is the ability of one genotype to display different phenotypes under different environmental conditions. Although variation for phenotypic plasticity has been document in numerous species, little is known about the genetic mechanisms underlying phenotypic plasticity. Given their widespread roles in hormonal and environmental signaling, we examined whether genes which encode heterotrimeric G proteins are plasticity genes.

We grew multiple alleles of heterotrimeric G-protein mutants, together with wild-type *Arabidopsis thaliana*, under different watering regimes to determine the contributions of G-protein genes to phenotypic plasticity for a number of developmental and reproduction-related traits.

G-protein mutations did not affect significantly the amount of phenotypic variation within an environment for any trait, but did affect significantly the amount of phenotypic plasticity for certain traits.

AGB1, which encodes the β subunit of the heterotrimeric G protein in *Arabidopsis*, is a plasticity gene and regulates reproductive trait plasticity in response to water availability, resulting in increased fitness (defined as seed production) under drought stress.

Introduction

Heterotrimeric G proteins are multisubunit guanosine triphosphate (GTP)-binding proteins that function in the transduction of external signals into cellular responses. Because G proteins regulate a large array of cellular and developmental processes in both plants and animals, it is of interest to evaluate their potential impact on developmental plasticity and fitness. According to the paradigm of G-protein signaling, the G protein is activated following the binding of a ligand to an associated membrane-bound G-protein-coupled receptor (GPCR). This binding results in a conformational change in the alpha subunit (Gα) and the subsequent exchange of GTP for guanosine diphosphate by Gα, resulting in the dissociation of Gα from the beta gamma dimer (Gβγ). Gα and/or Gβγ are then free to interact with downstream signal effectors until the intrinsic GTPase activity of Gα results in the reassembly of the inactive trimer (Assmann, 2002).

In mammals, there are a number of genes which encode heterotrimeric G-protein subunits and hundreds of GPCRs have been predicted, resulting in a large, diverse assortment of potential G-protein signaling pathways (Fredriksson & Schioth, 2005; McCudden et al., 2005). Numerous ligands have also been identified for mammalian GPCRs, including light, sensory molecules including odors and tastes, hormones, neurotransmitters and bacterial toxins (Civelli, 2005), and mutations in mammalian G-protein subunits often result in genetic disorders (Spiegel & Weinstein, 2004; Weinstein et al., 2006).

Plants possess few genes which encode G-protein subunits, and mutations in these genes, despite their broad expression throughout the plant body, do not result in lethality or in extreme phenotypes under 'ideal' laboratory growth conditions (Perfus-Barbeoch et al., 2004). The *Arabidopsis thaliana* genome contains single genes encoding Gα (GPA1) (Ma et al., 1990) and Gb (AGB1) (Weiss et al., 1994) subunits, and two known Gγ (AGG1 and AGG2) (Mason & Botella, 2000, 2001) genes. GPCR diversity is also reduced in *Arabidopsis*; only one putative GPCR, GCR1, has been functionally characterized (Pandey & Assmann, 2004), although several dozen additional genes have been predicted to function as GPCRs based on topology prediction (Moriyama et al., 2006; Gookin et al., 2008) and coupling to GPA1 in yeast (Gookin et al., 2008). To date, some phenotypes of *Arabidopsis* G-protein mutants, such as leaf morphology and lateral root production (Ullah et al., 2001, 2003), have been shown to be regulated by G-protein subunits in congruence with classical mammalian paradigms, whereas other phenotypes, such as root waving and control of floral and fruit morphology (Pandey et al., 2008; Trusov et al., 2008), suggest unique variants of plant G-protein regulatory modes (Assmann, 2005; Temple & Jones, 2007). Such variants may be mechanistically related to plant-specific aspects of the G-protein complement, including the slow GTPase activity of the plant Gα subunit (Johnston et al., 2007; Pandey et al., 2009), the existence of an unusual class of plant-specific Gα-like proteins, the extra-large G proteins (Lee & Assmann, 1999; Pandey et al., 2008) and the presence in *Arabidopsis* of novel GPCR-like regulatory proteins, the GTG and RGS proteins (Chen et al., 2003; Pandey et al., 2009).

Despite the paucity of heterotrimeric G-protein subunits in the *Arabidopsis* genome, functional studies of G-protein mutants have shown diverse roles for heterotrimeric G proteins in germination, development, phytohormone responses [abscisic acid (ABA), auxin, brassinosteroids, gibberellins], stress responses (ozone, reactive oxygen species, pathogens) and stomatal aperture regulation (Ullah et al., 2001, 2002, 2003; Wang et al., 2001, 2007; Pandey & Assmann, 2004; Joo et al., 2005; Llorente et al., 2005; Pandey et al., 2006; Fan et al., 2008; Zhang et al., 2008a; Zhang et al., 2008b). How a limited number of heterotrimeric G-protein subunits can transduce such a large number of hormonal and environmental signals is a fundamental question in plant G-protein signaling (Assmann, 2004). Further characterization of GTGs and other unconventional G proteins, such as the XLGs (Lee & Assmann, 1999; Ding et al., 2008), and the identification of GPCR ligands, potential tissue-specific GPCRs, and G-protein signaling effectors in plants may help to elucidate this question. An additional model which has been proposed is that G proteins may serve as signal modulators instead of direct transducers of signals (FIG. 1). By functioning as 'cross-talk hubs', G proteins could fine tune a phenotype or physiological response based on multiple signals/environmental inputs (Assmann, 2004). This model also addresses another paradox in plant G-protein signaling: why, if G proteins are important to plant physiology, are G-protein mutations not lethal in plants? A mutation may not be lethal if additional copies or similar versions of the gene exist in the genome or if the expression of the gene is specific to a certain stress (e.g. cold shock) or to a less vital plant tissue or cell type (e.g. trichomes). However, none of these situations applies to *Arabidopsis* as Gα and Gβ are both encoded by single, canonical genes which are widely expressed throughout the plant (Ma et al., 1990; Huang et al., 1994; Lease et al., 2001; Anderson & Botella, 2007). Alternatively, if G proteins function in directing hormonal and environmental cross-talk, they may be required only in the production of the 'optimal' phenotype, and the direct transducers of the signal would still function in the absence of functional G-protein subunits.

Plants, being sessile organisms, are hypothesized to have evolved increased phenotypic plasticity, the ability of one genotype to display different phenotypes under different environmental conditions, compared with their mobile animal counterparts (Bradshaw, 1972; Schlichting, 1986; Sultan, 1987; Huey et al., 2002). Heightened plasticity in plants would allow plants to compensate for inescapable and inhospitable environments. Although variation for plasticity has been documented in numerous plant and animal species, and many theories have been proposed concerning the ecological and evolutionary significance of this variation, very little is known about the explicit genetic machinery which underlies phenotypic plasticity.

The phenotypic plasticity (or lack thereof) of a trait can be graphically represented by a reaction norm, which is a plot of the mean phenotypic value of the trait in different environmental conditions (FIG. 2). A horizontal reaction norm indicates that the trait lacks plasticity, whereas a line with a nonzero slope or a curved line is indicative of phenotypic plasticity. As plasticity genes control the shape or slope of the reaction norm of a trait, when these genes are mutated, it is expected that the shape/slope of the reaction norm will diverge from that of the wild-type. Mutations may alter the height of the reaction norm without affecting the overall plasticity for a trait (line C), affect the amount of plasticity for a trait (line B) or may change the direction of plasticity for a trait (line D). Differences in reaction norm shapes (plasticities) among genotypes can be detected and tested using analysis of variance (ANOVA)-based statistical methods. Specifically, a significant genotype×environment/treatment interaction term for a trait indicates that there is variation for plasticity among the genotypes, that is, the response curves have different shapes/slopes.

Although functional analysis of specific genic mutants is a widespread method to determine gene function, this technique has been applied to phenotypic plasticity studies only in a few instances, which have focused mainly on photoreceptor genes. For example, in *Arabidopsis*, this approach has been employed to study the genetic basis of phenotypic plasticity in photomorphogenetic responses (Pigliucci & Schmitt, 1999, 2004). *Arabidopsis* hy1 and hy2 photoreception mutants, which display constitutively active shade avoidance responses, showed reduced fitness under some environmental conditions relative to the more plastic wild-type (Pigliucci & Schmitt, 1999). This result suggests that HY1 and HY2 (which encode a plastid heme oxygenase and a phytochromobolin synthase, respectively) (Muramoto et al., 1999; Kohchi et al., 2001) are plasticity genes. In addition, naturally occurring polymorphism of the photochrome PHYB locus has been associated with altered light responses in *Arabidopsis*; however, phenotypic plasticity was not measured explicitly (Filiault et al., 2008). In field experiments, plants harboring mutations in phototropin blue light photoreceptors showed reduced fitness relative to the wild-type under a range of light conditions; however, significant genetic variation for phenotypic plasticity was observed only for the seedling emergence rate (Galen et al., 2004).

Genetic variation for plasticity has also been documented among wild-type accessions of *Arabidopsis* (Pigliucci & Kolodynska, 2002; Schmuths et al., 2006; Brock & Weinig, 2007), and naturally occurring variation for plasticity within plant species has been assessed in quantitative trait locus (QTL)-based phenotypic plasticity studies. Using recombinant inbred lines in lieu of genetic mutants, these studies have lent additional support for the existence of plasticity genes. Studies on recombinant inbred lines of *Arabidopsis* (Kliebenstein et al., 2002; Ungerer et al., 2003; Juenger et al., 2005), barley (Lacaze et al., 2009) and poplar (Wu, 1998) found significant QTL×environment interaction for a number of traits. Specifically with regard to drought stress in *Arabidopsis*, Hausmann et al. (2005) found significant recombinant inbred line×environment interactions for a number of water use traits, further supporting the existence of genes which regulate phenotypic plasticity to drought stress in *Arabidopsis*.

The signaling cross-talk mechanism discussed above may be an important component of phenotypic plasticity, as phenotypes could be tweaked on the basis of multiple environmental inputs. A mutation in a G-protein subunit might decrease cross-talk and therefore reduce the plant's ability to adjust a phenotype or response to changing environments based on multiple signals. Specifically, a G-protein mutation might affect the degree of plasticity of a trait (FIG. 2, line B), the amount of variation within an environment for a trait (that is the 'noisiness' of the trait) or might simply shift the mean value of the trait away from the wild-type value (FIG. 2, line C) (Assmann, 2004). Therefore, by studying populations of G-protein mutants under multiple environments, we might reveal whether G-protein genes are plasticity genes, as well as evaluate the importance of G proteins to plant fitness. In addition, previous studies of heterotrimeric G proteins have, to a large extent, focused on guard cell physiology (Wang et al., 2001; Pandey & Assmann, 2004; Fan et al., 2008) and cell division (Ullah et al., 2001, 2003; Chen et al., 2006). By studying whole-plant phenotypic plasticity responses of G-protein mutants, we might reveal novel functions of G proteins that could not be identified by previous cell-centered approaches.

As G-protein signaling has been implicated in stomatal aperture regulation (Wang et al., 2001; Pandey & Assmann, 2004; Fan et al., 2008), stomatal density (Zhang et al., 2008a) and seed and seedling ABA responses (Pandey et al., 2006), we chose G-protein regulation of phenotypic plasticity and plant fitness under drought as the focus of the present study. The following questions were asked:

1. Do G-protein mutations alter the shape/slope of reaction norms in response to water availability, that is are G-protein genes 'plasticity genes'?
2. Does a G-protein mutation affect the level of phenotypic variation within an environment?
3. What are the fitness consequences of G-protein mutations in different environments?

Using multiple alleles of gpa1, agb1 and gcr1 mutants, we found significant variation for plasticity for a number of reproduction-related traits in response to water availability. agb1 mutants showed significantly reduced plasticity for inflorescence height, number of fruits and seed number per fruit. Interestingly, agb1 mutants showed enhanced fitness under drought compared with the wild-type, but all G-protein mutants showed reduced fitness under ample water conditions. These data support the hypothesis that heterotrimeric G-protein genes are indeed plasticity genes in plants.

Materials and Methods

Plant Growth Conditions and Water Treatments

All *Arabidopsis thaliana* (L.) Heynh seeds used in this experiment were collected from parent plants that were grown together under uniform conditions. gpa1-3, gpa1-4, agb1-1, agb1-2, gcr1-1, gcr1-2 and gpa1-4agb1-2 mutants have all been described previously and were generated using the ecotype Col (Lease et al., 2001; Jones et al., 2003; Ullah et al., 2003; Chen et al., 2004). All mutants are TDNA insertional mutants, with the exception of agb1-1, which is an ethylmethanesulfonate-generated point mutation (Lease et al., 2001). It has been determined that gpa1-3 and gpa1-4 are null mutants at both the transcript and protein levels (Jones et al., 2003). agb1-2, gcr1-1 and gcr1-2 are all transcript null alleles (Ullah et al., 2003; Chen et al., 2004). agb1-1 produces a larger and less abundant AGB1 transcript compared with the wild-type as a result of a destabilizing point mutation, which results in a failure to splice out the first intron and the introduction of a premature stop codon (Lease et al., 2001). All alleles were backcrossed once in our laboratory and the genotypes of parent plants were confirmed via PCR of genomic DNA. Seed storage was identical for all seed lots. Cold stratified seeds (stratified at 4° C. for 48 h in darkness on wet filter paper) were sown directly on the surface of a soil mix composed of Miracle-Gro potting mix (The Scotts Co, Marysville, Ohio, USA), Turface Greens Grade fritted clay (Profile Products LLC, Buffalo Grove, Ill., USA) and perlite in a 16:8:1 volume ratio. The plants were grown in Kord 90 mm press-fit pots (Kord Products Inc. Brampton, Ontario, Canada) in a walk-in Conviron growth chamber (Conviron Inc. Winnipeg, Manitoba, Canada). The photoperiod was 12 h light (140 µmol $m^{-2}$ $s^{-1}$, 21° C.) and 12 h dark (19° C.) and the relative humidity was 60%.

Three weeks after sowing, the plants were treated with one of three watering regimes: ample water, moderate drought or severe drought. The moderate and severe drought designations are relative to the ample water treatment for our experiment. Plants were individually watered using a bottle-top volumetric dispenser. Plants subjected to ample watering had continually moist soil (c. 95% of the soil water-carrying capacity) and weekly water applications ranging from 55 to 170 ml depending on the plant age. Ample water-treated plants never wilted between waterings, showed no signs of waterlogging and were healthy in appearance. Severe drought-treated plants had soil which dried out completely between watering (c. 20% of the soil water-carrying capacity) and had weekly water applications ranging from 10 to 50 ml. Severe drought-treated plants displayed considerable wilting between waterings. Plants receiving the moderate drought treatment received approximately twice the volume of water applied to the severe drought-treated plants (c. 40% of the soil water-carrying capacity). Moderate drought-treated plants showed some turgor loss between watering, but to a lesser extent compared with the severe drought-treated plants. Water application was adjusted for treatment and plant age, and all plants within a treatment received the same amount of water. Relative water content measurements of 5-wk-old fully expanded leaves from three blocks showed no significant differences between the genotypes for any watering regime, indicating that the levels of drought stress were consistent across genotypes (data not shown). The average leaf relative water contents for each treatment were 76% for ample water, 65% for moderate drought and 61% for severe drought. These values are within the wide range of leaf relative water content values utilized for *Arabidopsis* drought stress in other published reports (Gigon et al., 2004; Rizhsky et al., 2004).

Experimental Design and Response Variables

Plants were arranged in a split-plot design. Three trays, each representing one water level, were clustered in a block, and 12 blocks were placed on separate shelves in the growth chamber. Genotypes were randomly assigned a position within a tray with two genotype replicates per tray. There were two replicate plants×8 genotypes×3 treatments×12 blocks for a total population of 576 plants. The transition from vegetative to reproductive growth was assessed by recording the flowering time (days from sowing), when the first open flower was visible, for each plant. Because of the large population size and the fact that flowering times were affected by treatment and genotype, each plant was individually harvested 4 wks. after the plant began to flower and the following variables were recorded: inflorescence height (cm), number of primary lateral branches and number of fruits plus any pistil which showed elongation or swelling. Excised rosettes were dried at 70° C. until a constant mass was achieved, and the dry mass was determined. For three blocks of plants, five fruits were harvested (two from the main inflorescence and three from the lateral branches), and the seed number per fruit was determined using a dissecting scope. Aborted or shriveled seeds were excluded from the seeds per fruit measurements. Seed production was estimated for each plant in the three blocks which had seeds per fruit measurements as (total fruit number×seeds per fruit). Relative fitness (total seed number×mean total seed number for water level) was calculated post hoc for the three blocks for which total seed production was determined.

Statistical Analysis

Experiment-wide variances for genotype means under ample water and drought stress were calculated using Minitab 15 (Minitab Inc. State College, Pa., USA). F test equal variance tests were performed in Minitab between mutant and wild-type trait variances from ample water and severe drought stress treatments. Eighty-four F tests were performed and the sequential Bonferroni correction was applied to keep a table-wide α of 0.05 (Rice, 1989).

Multivariate and univariate analyses were performed using Proc GLM in SAS 9.1 (SAS Inc. Cary, N.C., USA). As plant mortality resulted in an unbalanced design, the two genotype×treatment replicates within a block were averaged to enable analysis by Proc GLM. Multivariate analysis of variance (MANOVA) was first performed to identify whether there were significant effects of genotype, treatment, and genotype×treatment interaction for a suite of reproduction-related traits, including rosette mass, inflorescence height, lateral branch number and fruit number. A second MANOVA was performed using data only from the three blocks for which the seed number per fruit and total seed production were calculated. The second MANOVA included the following response variables: rosette mass, inflorescence height, lateral branch number, fruit number, seed number per fruit and total seed production. Univariate ANOVAs were performed following the MANOVAs in order to determine which traits showed significant variation for phenotypic plasticity (genotype×treatment interaction). Flowering time was analyzed using ANOVA only. For both the multivariate and univariate analyses, the split-plot experimental design required that the whole-plot factor, treatment, be tested over the whole-plot random error term, treatment×block. Genotype and genotype×treatment interaction were tested over the residual error. Data and residuals were examined to ensure that all ANOVA assumptions were satisfied. Fruit number and total seed production required transformation (square root) in order to satisfy ANOVA assumptions of normality and stable variance. Square root transformation was used, because it is the recommended method for normalizing counted data (Kuehl, 2000) and was the most effective transformation for meeting the ANOVA assumptions. The sequential Bonferroni correction was applied to the univariate P values to minimize inflation of table-wide error from multiple tests (Rice, 1989).

To determine whether G-protein mutants showed significantly different plasticities relative to Col, contrasts were performed using SAS 9.1 to test a priori-selected comparisons on all traits which had a significant genotype×water level interaction. Because two alleles of each mutant were studied, the contrasts were designed to simultaneously test the plasticity of Col against the plasticities of both mutant alleles of each gene. Combining alleles limited the inflation of α and, at the same time, increased the biological validity of the experiment: if the two mutant alleles of the same gene showed divergent responses, statistically significant differences with Col would probably not be detected. However, reaction norms were also examined individually to ensure that alleles of the same gene had similar plasticity responses.

The following contrasts were performed for the univariate analyses: Col against both alleles combined for gpa1, agb1 and gcr1 mutants for ample water vs moderate drought and ample water vs severe drought. The double mutant gpa1-4agb1-2 was tested against Col, and against both alleles combined of gpa1 or agb1 for ample water vs moderate drought and ample water vs severe drought. The sequential Bonferroni correction was applied to adjust for the inflation of type 1 error and to maintain a table-wide α of 0.05 (Rice, 1989). It has been suggested that the sequential Bonferroni correction can be overly stringent when applied to ecological experiments; therefore, we also applied biological reasoning when interpreting each contrast (Moran, 2003). Because relative fitness (Stanton & Thiede, 2005) was a post hoc addition to our analysis, relative fitness was analyzed independently from the other response variables. ANOVA was performed to test whether genotype, treatment and genotype by treatment interaction were significant.

Results

Variation for Plasticity Among Genotypes (Genotype×Environment Interactions)

Both MANOVAs showed that there is significant genotype×treatment interaction (Tables 1 and 2) for the reproduction-related traits (both P values were <0.0001). Significant genotype and treatment effects were also observed; however, the treatment effect for the seven variable MANOVA performed on only three blocks (Table 2) could not be estimated as a result of insufficient error degrees of freedom. The MANOVAs indicated that significant genetic variation exists for reproductive trait plasticity. Univariate ANOVAs were then performed in order to determine which specific traits showed significant genotype×treatment interaction. The results from the univariate ANOVAs are shown in Table 3. We found significant genotype×environment interactions for all traits, even after the sequential Bonferroni correction was applied to the P values. Least-squares means and standard errors are listed for all alleles and water levels in Table S1 (see Supporting Information). F tests of specific contrasts between any of the G-protein mutants and Col for ample water vs moderate drought and ample water vs severe drought revealed that, for rosette mass, number of lateral branches, total seed production and flowering time, there were no significant differences in genotype×water level interactions (plasticities) after the application of the sequential Bonferroni correction (Table 4). However, significant differences in plasticities were observed between Col and the G-protein mutants for a number of reproduction-related traits (Table 4). Although the contrasts were performed on pooled alleles, reaction norms for mutant alleles of the same gene were examined in cases in which the contrasts were significant; such examination confirmed that both alleles of each gene did indeed show similar responses for all plasticity traits discussed here (see, for example, Figs S4-S7; Supporting Information). Interestingly, agb1 mutants showed significantly reduced plasticities relative to Col for inflorescence height (FIG. 3), fruit number (FIG. 4) and seeds per fruit (FIG. 5), suggesting that AGB1 functions as a plasticity gene, mediating phenotypic plasticity in the reproductive phase of plant growth in response to water availability. The plasticities of the gpa1-4 agb1-2 double mutant for the most part resembled those of the single agb1 mutants. The exception was the inflorescence height, for which agb1 mutants showed significantly reduced plasticity relative to the double mutant (FIG. 3, Table 4). gpa1 mutants showed increased plasticity for inflorescence height relative to Col (FIG. 3). The double mutant showed reduced plasticity relative to gpa1 for inflorescence height (FIG. 3), indicating that the double mutant shows an intermediate phenotype. gcr1 mutants showed increased plasticity for square root fruit number relative to the wild-type (FIG. 4).

For total seed production, no significant differences were found in the plasticities of Col and any of the G-protein mutants following the sequential Bonferroni correction (Table 2). However, it should be noted that, before statistical correction, contrasts between Col and agb1 in ample water vs moderate drought (P=0.0027) and ample water vs severe drought (P=0.003) were significant. Given that two independent alleles of agb1 were used in the experiment and their reaction norms showed reduced plasticity for total seed production (FIG. 6; see also FIG. S7, Supporting Information) relative to Col, and also that the sequential Bonferroni correction can be overly conservative (Moran, 2003), we feel confident that AGB1 also mediates plasticity for total seed production. All G-protein mutants showed reduced fitness, defined here as total seed production, under ample water conditions, but the agb1 mutants and the double mutant gpa1agb1 showed increased fitness under both moderate and severe drought stress relative to Col (FIG. 6). The relative fitness data also corroborate rank changing among the genotypes in different environments (FIG. 7). A significant genotype effect (P<0.0001) and significant genotype× treatment interaction (P=0.0009) were observed for relative fitness. Although all mutant genotypes showed reduced relative fitness relative to Col under ample water growth conditions, agb1 mutants and the double mutant gpa1-4agb1-2 showed increased relative fitness relative to Col under drought stress.

Phenotypic Variance of within×Treatment Trait Means

The within-treatment, experiment-wide variances of the trait means for the mutants and wild-type for ample water and severe drought treatments are shown in Table S2 (see Supporting Information). Equal variance tests were performed to determine whether the mutants showed increased or decreased phenotypic variation relative to the wild-type within a particular environment (Table S3). After correcting for multiple F tests using the sequential Bonferroni correction, only one null hypothesis was rejected. agb1-2 mutants showed significantly reduced variance (P<0.0005) for seed number per fruit under ample water relative to the wild-type. However, this reduction in variance was not observed in the second agb1 allele, agb1-1 (P=0.168), which brings into question the biological relevance of this statistically significant observation. Overall, phenotypic variance for traits within a given environment was not impacted significantly by G-protein mutations.

Discussion

AGB1 Functions as a Plasticity Gene for a Number of Reproduction-Related Traits

Our data show that mutation of the sole Gβ subunit of *Arabidopsis*, AGB1, results in pleiotropic effects on the extent of plasticity in response to water availability. agb1 mutants showed reduced plasticity for the number of fruits, inflorescence height, seed number per fruit and total seed production relative to Col. Interestingly, agb1 mutants showed increased seed production per fruit under drought stress relative to the wild-type, and reduced seed production per fruit relative to the wild-type under well-watered conditions. The reduced plasticity of agb1 mutants resulted in enhanced fitness under drought stress, but was maladaptive under well-watered conditions. This conclusion was also supported when relative fitness was assessed. All G-protein mutants, that showed reduced plasticity for reproductive traits, including agb1, showed lower relative fitness relative to Col under ample water conditions. Under drought stress, agb1 mutants and the double mutant showed increased relative fitness relative to Col. The relative fitness data support the conclusion that the significant genotype×treatment interaction observed for total seed production can be attributed to rank changing among the genotypes, and is not a consequence of changes in variance or the square root transformation. It has also been noted that differences in phenotypic variation can be a consequence of age- or size-dependent ontogenetic drift (McConnaughay & Coleman, 1999). It should be noted that we observed no significant differences in rosette growth rate (as determined by projected leaf area calculations) among the genotypes within a given water treatment (Figs S1-S3, see Supporting Information), suggesting that the significant variation for plasticity observed cannot be attributed to ontogenetic drift. These results suggest that AGB1 is a plasticity gene, as it contributes to the shape of the phenotypic response under the environments tested in our experiment.

Multiple alleles have not been used frequently in mutant studies of phenotypic plasticity; one exception is the study by Galen et al. (2004). The use of two independent mutant alleles of agb1 in this study strengthens our conclusion that AGB1 functions as a plasticity gene, at least in the environments tested. These results suggest that it would be worthwhile to pursue additional experiments to determine the extent to which G proteins function in regulating phenotypic plasticity under different stresses and in natural environments, where other resource limitations might influence the extent of plasticity observed. It has been recognized that there may also be costs associated with plasticity under some circumstances (Callahan et al., 2005; Ghalambor et al., 2007; Van Buskirk & Steiner, 2009). Although additional research under different environments is required, plasticity costs may be illustrated under our conditions by the fact that, under water limitation, the least plastic genotype, agb1, showed greater fitness (by both absolute and relative measures) than the more plastic genotypes.

AGB1 has been shown previously to function in inflorescence and fruit development. agb1-1 was originally isolated in a screen for erecta-like mutations, where it showed a slightly reduced inflorescence height and significantly shortened, blunt-tipped fruits relative to the wild-type, phenotypes which were later also observed in agb1-2 (Lease et al., 2001; Ullah et al., 2003). In addition, it was shown that AGB1 was expressed ubiquitously throughout the plant, but its expression was elevated in flowers and highest in fruits (Lease et al., 2001). The shortened fruit phenotype corresponds to our findings that agb1 shows reduced seeds per fruit. This short phenotype is specific to agb1 mutants and is not observed in gpa1, agg1 and agg2 mutants (Ullah et al., 2003; Trusov et al., 2008). Functional selectivity of the Gβ subunit has been reported for other G-protein-mediated responses, including necrotrophic pathogen resistance (Llorente et al., 2005; Trusov et al., 2006), sugar inhibition of seed germination and lateral root formation (Chen et al., 2006).

According to the paradigm of G-protein signaling, activation of GPA1 results in a conformational change in Gα and the release of the Gβγ dimer, and signal propagation. As the reduced plasticity phenotype is present in agb1 mutants and in gpa1agb1 double mutants, but not in gpa1 mutants, we can conclude that Gβ is responsible for signal integration or transduction, resulting in wild-type plasticity for the number of fruits, seed number per fruit and total seed production. In classical G-protein signaling, the a subunit typically requires the β subunit, not only for trimer reassembly, but also for GPCR association. Therefore, GPA1 activation is eliminated by both gpa1 and agb1 mutations, but AGB1 activation is abolished only by the agb1 mutation. For inflorescence height, gpa1 and agb1 display opposite phenotypes (enhanced and reduced plasticity, respectively), which also suggests that AGB1 is responsible for mediating wild-type plasticity, as free AGB1 is active in gpa1 mutants (potentially more so than in the wild-type), but is absent from agb1 mutants. gcr1 mutants showed increased plasticity relative to the wild-type for fruit number and, although GCR1 might function in the mediation of plasticity for fruit number, there are probably additional unknown GPCRs that contribute to the perception and/or integration of environmental input signals with regard to the regulation of phenotypic plasticity.

G-Protein Mutations do not Affect Significantly the Level of Phenotypic Variation within an Environment Within a given environment, genetically identical organisms can show divergent phenotypes as a result of stochasticity in gene expression. These random events among cellular molecules can modify cell status and consequently result in phenotypic changes at the organismal level (often thought of as experimental 'noise'). Stochasticity is generally thought to be detrimental to fitness; however, it can also be a source of heterogeneity, which can provide a fitness benefit in fluctuating environments (Kaern et al., 2005; Raser & O'Shea, 2005). A G-protein mutation might increase or decrease the ability of a cell to buffer itself against stochasticity, and therefore it has been hypothesized that G-protein mutations might affect the amount of phenotypic variation within an environment (Assmann, 2004). To test this hypothesis, we compared the phenotypic variances (Table S2) of the G-protein mutants within an environment with the phenotypic variance of the wild-type within the same environment. We found that the within-environment phenotypic variation was not altered significantly by mutations in G-protein subunit genes (Table S3, Supporting Information), suggesting that this hypothesis is not supported: G-protein mutations do not affect the range of possible phenotypes within our environments.

agb1 Mutants Show Enhanced Fitness Under Drought Stress

Based on their previously reported altered stomatal sensitivities to ABA (Wang et al., 2001; Pandey & Assmann, 2004; Fan et al., 2008), it is possible to make predictions concerning the fitness benefits or costs that G-protein mutants may incur when grown under drought stress conditions. However, although gpa1 and agb1 are hyposensitive with regard to the ABA inhibition of stomatal opening, but show wild-type ABA promotion of stomatal closure (Wang et al., 2001; Fan et al., 2008), and gcr1 mutants are hypersensitive towards both ABA inhibition of stomatal opening and promotion of closure (Pandey & Assmann, 2004), our detailed phenotypic analysis of whole-plant traits under controlled water stress conditions did not support the predictions that would be made based on these stomatal response phenotypes. gcr1 mutants, despite their stomatal hypersensitivity to ABA and their reported improved recovery following drought stress (Pandey & Assmann, 2004), showed no fitness advantage relative to the wild-type under drought stress or well-watered conditions. Although we predicted that gpa1 and agb1 mutants would show reduced fitness under drought stress based on the partial ABA insensitivity of their stomatal phenotypes, agb1 mutants (but not gpa1 mutants) exhibited increased fitness under drought stress and reduced fitness under well-watered conditions. The pleiotropic nature of G-protein mutations may, in part, explain why the stomatal response phenotypes were not predictive of plant fitness under drought stress. Recently, it has been shown that G proteins regulate stomatal density, GPA1 as a positive modulator and AGB1 as a negative regulator (Zhang et al., 2008a), which may have implications for water loss and carbon assimilation under different environmental conditions. In addition, agb1 mutants and, to a lesser degree, gpa1 mutants are hypersensitive to ABA inhibition of germination and root growth (Pandey et al., 2006), which may contribute to survival under drought stress. Nevertheless, although the lack of plasticity of agb1 in reproductive-related traits resulted in a fitness advantage under drought stress, lack of plasticity was maladaptive for agb1 under well-watered conditions. Therefore, G proteins do contribute to plant fitness, in part via the regulation of phenotypic plasticity. Given that climate change can lead to increased variability in environments and resources, this finding could have important agronomical implications, as agb1 mutants show reduced plasticity and therefore more stable yields across environments.

CONCLUSION

Phenotypic analysis of G-protein mutants under multiple environmental conditions has identified novel functions of plant heterotrimeric G proteins in the regulation of the phenotypic plasticity of inflorescence height, seed number per fruit, fruit number and total seed production. We also found that the known altered guard cell sensitivities towards ABA did not predict the fitness outcomes of the mutants under drought stress. All G-protein mutants studied showed reduced fitness under well-watered as well as drought environments, with the exception of agb1-containing mutants which showed improved fitness under drought stress conditions. These results thus attest to one of the apparent paradoxes of plant G-protein signaling: although G-protein mutation is not lethal, it does, in fact, result in nonoptimal phenotypes under some environmental conditions.

G proteins mediate responses to ABA, auxin, brassinosteroids, gibberellins and sugars, environmental signals, including ozone and pathogens, and intrinsic, unknown developmental cues mediating leaf shape, stomatal density and fruit shape. A fundamental question in G-protein signaling is how only two heterotrimeric G-protein combinations (GPA1/AGB1/AGG1 and GPA1/AGB1/AGG2) can transduce such a diversity of signals. Our results, implicating heterotrimeric G proteins in the mediation of phenotypic plasticity responses, support the model that G proteins function, at least in part, as cross-talk hubs, integrating signals, rather than directly transducing them (Assmann, 2004), thereby tweaking a phenotype relative to the environment at hand. More studies are warranted in which G-protein regulation of plasticity is examined across additional environmental gradients, as well as across generations, in order to further elucidate this novel contribution of heterotrimeric G proteins to plant development and fitness. It will be interesting to assess the extent to which the results presented here would extrapolate to field studies: studies in highly controlled environments are important steps towards the design of such experiments. Although QTL-based studies have supported the existence of plasticity genes, the present study is one of a few that has directly tested the regulation of phenotypic plasticity by specific genes. Additional plasticity studies with other environmental signaling mutants will be integral to our understanding of whether plasticity genes are rare or common in plant and other genomes, and to gaining an insight into the genetic basis of phenotypic plasticity.

TABLE 1

Wilks' lambda, F and P values from multivariate analysis of variance (MANOVA) including the following response variables: rosette mass, inflorescence height, number of lateral branches and square root number of fruits; data from all 12 experimental blocks

| Effect | Wilks' lambda | F value | Numerator d.f. | Denominator d.f. | P value |
|---|---|---|---|---|---|
| Genotype | 0.0419 | 41.48 | 28 | 823.49 | <0.0001 |
| Treatment | 0.0056 | 58.65 | 8 | 38 | <0.0001 |

TABLE 1-continued

Wilks' lambda, F and P values from multivariate analysis of variance (MANOVA) including the following response variables: rosette mass, inflorescence height, number of lateral branches and square root number of fruits; data from all 12 experimental blocks

| Effect | Wilks' lambda | F value | Numerator d.f. | Denominator d.f. | P value |
|---|---|---|---|---|---|
| Genotype x treatment | 0.2046 | 8 | 56 | 889.04 | <0.0001 |

TABLE 2

Wilks' lambda, F and P values from multivariate analysis of variance (MANOVA) including the following response variables: rosette mass, inflorescence height, number of lateral branches and square root number of fruits; seed number per fruit and square root total seed production; data from the three experimental blocks for which seed number per fruit was obtained

| Effect | Wilks' lambda | F value | Numerator d.f. | Denominator d.f. | P value |
|---|---|---|---|---|---|
| Genotype | 0.0053[1] | 8.65[1] | 42[1] | 177[1] | <0.0001[1] |
| Treatment | | | | | |
| Genotype x treatment | 0.0208 | 2.54 | 84 | 212.6 | <0.0001 |

[1]Multivariate analysis of the significance of the treatment effect could not be performed because of insufficient error d.f. (treatment x block is the appropriate error term given the split-plot experimental design).

TABLE 3

F and (P values) for all fixed effects for univariate analyses of variance (ANOVAs); treatment was tested over the treatment x block error term, and genotype and genotype x treatment were tested over the residual error; all P values were significant before and after sequential Bonferroni correction

| | Effect | | |
|---|---|---|---|
| Response Variable | Genotype | Treatment | Genotype x treatment |
| Rosette mass | 28.08 (≤0.0001) | 744.91 (≤0.0001) | 8.43 (≤0.0001) |
| Inflorescence height | 40.89 (≤0.0001) | 541.7 (≤0.0001) | 12.79 (≤0.0001) |
| Number of lateral branches | 108.9 (≤0.0001) | 272.7 (≤0.0001) | 12.79 (≤0.0001) |
| Square root number of fruits | 9.35 (≤0.0001) | 320.91 (≤0.0001) | 13 (≤0.0001) |
| Seeds per fruit[1] | 10.47 (≤0.0001) | 256.7 (≤0.0001) | 4.23 (≤0.0001) |
| Seed production[1] | 7.79 (≤0.0001) | 220.07 (≤0.0001) | 2.88 (≤0.0041) |
| Flowering time | 50.37 (≤0.0001) | 12.7117323 (0.0002) | 3.23 (0.0001) |

[1]Only three blocks were used to assess seeds per fruit and seed production.

TABLE 4

P values of univariate contrasts on genotype x treatment (ample, ample water, moderate, moderate drought severe, severe drought)

| Response variable Contrast | Rosette mass | Inflorescence height | No. lateral branches | Sq. rt. no. fruit | Seeds per fruit[1] | Total seed production[1] | Flowering Time |
|---|---|---|---|---|---|---|---|
| Col vs both agb1 ample vs moderate | 0.0137 | 0.0001 | 0.104 | ≤0.0001 | 0.0003 | 0.0027 | 0.9828 |
| Col vs both agb1 ample vs severe | 0.002 | 0.0022 | 0.0183 | 0.0091 | ≤0.0001 | 0.003 | 0.645 |
| Col vs double ample vs moderate | 0.0017 | 0.472 | 0.0876 | ≤0.0001 | 0.0052 | 0.0323 | 0.8351 |

TABLE 4-continued

P values of univariate contrasts on genotype x treatment (ample,
ample water, moderate, moderate drought severe, severe drought)

| Response variable Contrast | Rosette mass | Inflorescence height | No. lateral branches | Sq. rt. no. fruit | Seeds per fruit[1] | Total seed production[1] | Flowering Time |
|---|---|---|---|---|---|---|---|
| Col vs double ample vs severe | 0.002 | 0.2793 | 0.1045 | 0.1331 | 0.0049 | 0.0715 | 0.3148 |
| Col vs both gcr1 ample vs moderate | 0.9661 | 0.8617 | 0.882 | 0.0024 | 0.7164 | 0.7598 | 0.5887 |
| Col vs both gcr1 ample vs severe | 0.2308 | 0.1975 | 0.4888 | _≤0.0001_ | 0.1723 | 0.8404 | 0.0859 |
| Col vs both gpa1 ample vs moderate | 0.3071 | 0.0007 | 0.1035 | 0.7262 | 0.5187 | 0.8318 | 0.496 |
| Col vs both gpa1 ample vs severe | 0.0301 | _≤0.0001_ | 0.0844 | 0.2792 | 0.1083 | 0.2709 | 0.0019 |
| Double vs both agb1 ample vs moderate | 0.2399 | 0.0024 | 0.7284 | 0.5487 | 0.5548 | 0.5354 | 0.8268 |
| Double vs both agb1 ample vs severe | 0.6283 | _≤0.0001_ | 0.6209 | 0.3752 | 0.3024 | 0.3139 | 0.1056 |
| Double vs both gpa1 ample vs moderate | _≤0.0001_ | _≤0.0001_ | 0.7291 | _≤0.0001_ | _≤0.0002_ | 0.0083 | 0.6594 |
| Double vs both gpa1 ample vs severe | _≤0.0001_ | _≤0.0001_ | 0.882 | 0.0051 | 0.0812 | 0.3138 | 0.0483 |

[1]Data from three blocks only.
Values in bold were significant before application of the sequential Bonferroni correction; values in italic and with underlines were significant after application of the Bonferroni correction.

REFERENCES

1. Anderson D J, Botella J R. 2007. Expression analysis and subcellular localization of the *Arabidopsis thaliana* G-protein b-subunit AGB1. *Plant Cell Reports* 26: 1469-1480.
2. Assmann S M. 2002. Heterotrimeric and unconventional GTP binding proteins in plant cell signaling. *Plant Cell* 14: S355-S373.
3. Assmann S M. 2004. Plant G proteins, phytohormones, and plasticity: three questions and a speculation. *Science's STKE* 2004: re20.
4. Assmann S M. 2005. G proteins Go green: a plant G protein signaling FAQ sheet. *Science* 310: 71-73.
5. Bradshaw A D. 1972. Some of the evolutionary consequences of being a plant. *Evolutionary Biology* 5: 25-47.
6. Brock M T, Weinig C. 2007. Plasticity and environment-specific covariances: an investigation of floral-vegetative and within flower correlations. *Evolution* 61: 2913-2924.
7. Callahan H S, Dhanoolal N, Ungerer M C. 2005. Plasticity genes and plasticity costs: a new approach using an *Arabidopsis* recombinant inbred population. *New Phytologist* 166: 129-140.
8. Chen J G, Willard F S, Huang J, Liang J, Chasse S A, Jones A M, Siderovski D P. 2003. A seven-transmembrane RGS protein that modulates plant cell proliferation. *Science* 301: 1728-1731.
9. Chen J G, Pandey S, Huang J, Alonso J M, Ecker J R, Assmann S M, Jones A M. 2004. GCR1 can act independently of heterotrimeric G-protein in response to brassinosteroids and gibberellins in *Arabidopsis* seed germination. *Plant Physiology* 135: 907-915.
10. Chen J G, Gao Y, Jones A M. 2006. Differential roles of *Arabidopsis* heterotrimeric G-protein subunits in modulating cell division in roots. *Plant Physiology* 141: 887-897.
11. Civelli O. 2005. GPCR deorphanizations: the novel, the known and the unexpected transmitters. *Trends in Pharmacological Sciences* 26: 15-19.
12. Ding L, Pandey S, Assmann S M. 2008. *Arabidopsis* extra-large G proteins (XLGS) regulate root morphogenesis. *Plant Journal* 53: 248-263.
13. Fan L M, Zhang W, Chen J G, Taylor J P, Jones A M, Assmann S M. 2008. Abscisic acid regulation of guard-cell K+ and anion channels in Gβ- and RGS-deficient *Arabidopsis* lines. *Proceedings of the National Academy of Sciences, USA* 105: 8476-8481.
14. Filiault D L, Wessinger C A, Dinneny J R, Lutes J, Borevitz J O, Weigel D, Chory J, Maloof J N. 2008. Amino acid polymorphism in *Arabidopsis* phytochrome β cause differential responses to light. *Proceedings of the National Academy of Sciences, USA* 105: 3157-3162.
15. Fredriksson R, Schioth H B. 2005. The repertoire of G-protein-coupled receptors in fully sequenced genomes. *Molecular Pharmacology* 67: 1414-1425.
16. Galen C, Huddle J, Liscum E. 2004. An experimental test of the adaptive evolution of phototropins: blue-light photoreceptors controlling phototropism in *Arabidopsis thaliana*. *Evolution* 58: 515-523.
17. Ghalambor C K, McKay J K, Carroll S, Reznick D N. 2007. Adaptive versus non-adaptive phenotypic plasticity and the potential for contemporary adaptation to new environments. *Functional Ecology* 21: 394-407.
18. Gigon A, Matos A R, Laffray D, Zuily-Fodil Y, Pham-Thi A T. 2004. Effect of drought stress on lipid metabolism in the leaves of *Arabidopsis thaliana* (Ecotype Columbia). *Annals of Botany* 94: 345-351.
19. Gookin T E, Kim J, Assmann S M. 2008. Whole proteome identification of plant candidate G-protein coupled receptors in *Arabidopsis*, rice, and poplar: computational prediction and in-vivo protein coupling. *Genome Biology* 9: R120.
20. Hausmann N, Juenger T, Sen S, Stowe K A, Dawson T E, Simms E L. 2005. Quantitative trait loci affecting $\delta^{13}$C and response to differential water availability in *Arabidopsis thaliana*. *Evolution* 59: 81-96.
21. Huang H, Weiss C A, Ma H. 1994. Regulated expression of the *Arabidopsis* G protein a subunit gene GPA1. *International Journal of Plant Sciences* 155: 3.
22. Huey R B, Carlson M, Crozier L, Frazier M, Hamilton H, Harley C, Hoang A, Kingsolver J G. 2002. Plants versus animals: do they deal with stress in different ways? *Integrative and Comparative Biology* 42: 415-423.

23. Johnston C A, Taylor J P, Gao Y, Kimple A J, Grigston J C, Chen J G, Siderovski D P, Jones A M, Willard F S. 2007. GTPase acceleration as the rate-limiting step in *Arabidopsis* G protein-coupled sugar signaling. *Proceedings of the National Academy of Sciences, USA* 104: 17317-17322.

24. Jones A M, Ecker J R, Chen J G. 2003. A reevaluation of the role of the heterotrimeric G protein in coupling light responses in *Arabidopsis. Plant Physiology* 131: 1623-1627.

25. Joo J H, Wang S Y, Chen J G, Jones A M, Fedoroff N V. 2005. Different signaling and cell death roles of heterotrimeric G protein α and β subunits in the *Arabidopsis* oxidative stress response to ozone. *Plant Cell* 17: 957-970.

26. Juenger T, Sen S, Stowe K, Simms E. 2005. Epistasis and gene-environment interaction for quantitative trait loci affecting flowering time in *Arabidopsis thaliana. Genetica* 123: 83-101.

27. Kaern M, Elston T C, Blake W J, Collins J J. 2005. Stochasticity in gene expression: from theories to phenotypes. *Nature Reviews. Genetics* 6: 451-464.

28. Kliebenstein D J, Figuth A, Mitchell-Olds T. 2002. Genetic architecture of plastic methyl jasmonate responses in *Arabidopsis thaliana. Genetics* 161: 1685-1696.

29. Kohchi T, Mukougawa K, Frankenberg N, Masuda M, Yokota A, Lagarias J C. 2001. The *Arabidopsis* HY2 gene encodes phytochromobilin synthase, a ferredoxin-dependent biliverdin reductase. *Plant Cell* 13: 425-436.

30. Kuehl R O. 2000. *Design of experiments: statistical principles of research design and analysis*, 2nd edn. Pacific Grove, Calif., USA: Duxbury Press.

31. Lacaze X, Hayes P M, Korol A. 2009. Genetics of phenotypic plasticity: QTL analysis in barley, *Hordeum vulgare. Heredity* 102: 163-173.

32. Lease K A, Wen J, Li J, Doke J T, Liscum E, Walker J C. 2001. A mutant *Arabidopsis* heterotrimeric G-protein β subunit affects leaf, flower, and fruit development. *Plant Cell* 13: 2631-2641.

33. Lee Y R, Assmann S M. 1999. *Arabidopsis thaliana* 'extra-large GTP-binding protein' (AtXLG1): a new class of G-protein. *Plant Molecular Biology* 40: 55-64.

34. Llorente F, Alonso-Blanco C, Sanchez-Rodriguez C, Jorda L, Molina A. 2005. ERECTA receptor-like kinase and heterotrimeric G protein from *Arabidopsis* are required for resistance to the necrotrophic fungus *Plectosphaerella cucumerina. Plant Journal* 43: 165-180.

35. Ma H, Yanofsky M F, Meyerowitz E M. 1990. Molecular cloning and characterization of GPA1, a G protein α subunit gene from *Arabidopsis thaliana. Proceedings of the National Academy of Sciences, USA* 87: 3821-3825.

36. Mason M G, Botella J R. 2000. Completing the heterotrimer: isolation and characterization of an *Arabidopsis thaliana* G protein γ-subunit cDNA. *Proceedings of the National Academy of Sciences, USA* 97: 14784-14788.

37. Mason M G, Botella J R. 2001. Isolation of a novel G-protein γ-subunit from *Arabidopsis thaliana* and its interaction with Gβ. *Biochimica et Biophysica Acta* 1520: 147-153.

38. McConnaughay K D M, Coleman J S. 1999. Biomass allocation in plants: ontogeny or optimality? A test along three resource gradients. *Ecology* 80: 2581-2593.

39. McCudden C R, Hains M D, Kimple R J, Siderovski D P, Willard F S. 2005. G-protein signaling: back to the future. *Cellular and Molecular Life Sciences* 62: 551-577.

40. Moran M D. 2003. Arguments for rejecting the sequential Bonferroni in ecological studies. *Oikos* 100: 403-405.

41. Moriyama E, Strope P, Opiyo S, Chen Z, Jones A. 2006. Mining the *Arabidopsis thaliana* genome for highly-divergent seven transmembrane receptors. *Genome Biology* 7: R96.

42. Muramoto T, Kohchi T, Yokota A, Hwang I, Goodman H M. 1999. The *Arabidopsis* photomorphogenic mutant hy1 is deficient in phytochrome chromophore biosynthesis as a result of a mutation in a plastid heme oxygenase. *Plant Cell* 11: 335-348.

43. Pandey S, Assmann S M. 2004. The *Arabidopsis* putative G protein-coupled receptor GCR1 interacts with the G protein α subunit GPA1 and regulates abscisic acid signaling. *Plant Cell* 16: 1616-1632.

44. Pandey S, Chen J G, Jones A M, Assmann S M. 2006. G-protein complex mutants are hypersensitive to abscisic acid regulation of germination and postgermination development. *Plant Physiology* 141: 243-256.

45. Pandey S, Monshausen G B, Ding L, Assmann S M. 2008. Regulation of root-wave response by extra large and conventional G proteins in I. *Plant Journal* 55: 311-322.

46. Pandey S, Nelson D C, Assmann S M. 2009. Two novel GPCR-type G proteins are abscisic acid receptors in *Arabidopsis. Cell* 136: 136-148.

47. Perfus-Barbeoch L, Jones A M, Assmann S M. 2004. Plant heterotrimeric G protein function: insights from *Arabidopsis* and rice mutants. *Current Opinion in Plant Biology* 7: 719-731.

48. Pigliucci M, Kolodynska A. 2002. Phenotypic plasticity and integration in response to flooded conditions in natural accessions of *Arabidopsis thaliana* (L.) Heynh (Brassicaceae). *Annals of Botany* 90: 199-207.

49. Pigliucci M, Schmitt J. 1999. Genes affecting phenotypic plasticity in *Arabidopsis*: pleiotropic effects and reproductive fitness of photomorphogenic mutants. *Journal of Evolutionary Biology* 12: 551-562.

50. Pigliucci M, Schmitt J. 2004. Phenotypic plasticity in response to foliar and neutral shade in gibberellin mutants of *Arabidopsis thaliana. Evolutionary Ecology Research* 6: 243-259.

51. Raser J M, O'Shea E K. 2005. Noise in gene expression: origins, consequences, and control. *Science* 309: 2010-2013.

52. Rice W R. 1989. Analyzing tables of statistical tests. *Evolution* 43: 223-225.

53. Rizhsky L, Liang H, Shuman J, Shulaev V, Davletova S, Mittler R. 2004. When defense pathways collide. The response of *Arabidopsis* to a combination of drought and heat stress. *Plant Physiology* 134: 1683-1696.

54. Schlichting C. 1986. The evolution of phenotypic plasticity in plants. *Annual Review of Ecology and Systematics* 17: 667-693.

55. Schmuths H, Bachmann K, Weber W E, Horres R, Hoffmann M H. 2006. Effects of preconditioning and temperature during germination for 73 natural accessions of *Arabidopsis thaliana. Annals of Botany* 97: 623-634.

56. Spiegel A M, Weinstein L S. 2004. Inherited diseases involving G proteins and G protein-coupled receptors. *Annual Review of Medicine* 55: 27-39.

57. Stanton M L, Thiede D A. 2005. Statistical convenience versus biological insight: consequences of data transformation for the analysis of fitness variation in heterogeneous environments. *New Phytologist* 166: 319-338.

58. Sultan S E. 1987. Evolutionary implications of phenotypic plasticity in plants. *Evolutionary Biology* 21: 127-178.

59. Temple B R, Jones A M. 2007. The plant heterotrimeric G-protein complex. *Annual Review of Plant Biology* 58: 249-266.

60. Trusov Y, Rookes J E, Chakravorty D, Armour D, Schenk P M, Botella J R. 2006. Heterotrimeric G proteins facilitate *Arabidopsis* resistance to necrotrophic pathogens and are involved in jasmonate signaling. *Plant Physiology* 140: 210-220.

61. Trusov Y, Zhang W, Assmann S M, Botella J R. 2008. Gγ1+Gγ2≠Gb: heterotrimeric G protein Gγ-deficient mutants do not recapitulate all phenotypes of Gβ-deficient mutants. *Plant Physiology* 147: 636-649.

62. Ullah H, Chen J G, Young J C, Im K H, Sussman M R, Jones A M. 2001. Modulation of cell proliferation by heterotrimeric G protein in *Arabidopsis*. *Science* 292: 2066-2069.

63. Ullah H, Chen J G, Wang S C, Jones A M. 2002. Role of a heterotrimeric G protein in regulation of *Arabidopsis* seed germination. *Plant Physiology* 129: 897-907.

64. Ullah H, Chen J G, Temple B, Boyes D C, Alonso J M, Davis K R, Ecker J R, Jones A M. 2003. The β-subunit of the *Arabidopsis* G protein negatively regulates auxin-induced cell division and affects multiple developmental processes. *Plant Cell* 15: 393-409.

65. Ungerer M C, Halldorsdottir S S, Purugganan M A, Mackay T F C. 2003. Genotype-environment interactions at quantitative trait loci affecting inflorescence development in *Arabidopsis thaliana*. *Genetics* 165: 353-365.

66. Van Buskirk J, Steiner U K. 2009. The fitness costs of developmental canalization and plasticity. *Journal of Evolutionary Biology* 22: 852-860.

67. Wang X Q, Ullah H, Jones A M, Assmann S M. 2001. G protein regulation of ion channels and abscisic acid signaling in *Arabidopsis* guard cells. *Science* 292: 2070-2072.

68. Wang S, Narendra S, Fedoroff N. 2007. Heterotrimeric G protein signaling in the *Arabidopsis* unfolded protein response. *Proceedings of the National Academy of Sciences, USA* 104: 3817-3822.

69. Weinstein L S, Chen M, Xie T, Liu J. 2006. Genetic diseases associated with heterotrimeric G proteins. *Trends in Pharmacological Sciences* 27: 260-266.

70. Weiss C A, Garnaat C W, Mukai K, Hu Y, Ma H. 1994. Isolation of cDNAs encoding guanine nucleotide-binding protein b-subunit homologues from maize (ZGB1) and *Arabidopsis* (AGB1). *Proceedings of the National Academy of Sciences, USA* 91: 9554-9558.

71. Wu R L. 1998. The detection of plasticity genes in heterogeneous environments. *Evolution* 52: 967-977.

72. Zhang L, Hu G, Cheng Y, Huang J. 2008a. Heterotrimeric G protein α and β subunits antagonistically modulate stomatal density in *Arabidopsis thaliana*. *Developmental Biology* 324: 68-75.

73. Zhang W, He S Y, Assmann S M. 2008b. The plant innate immunity response in stomatal guard cells invokes G-protein-dependent ion channel regulation. *Plant Journal* 56: 984-996.

```
RGA1 vs d1
Genbank RGA1 cDNA sequence:
Accession: D38232
GI: 540532
RGA1 coding region sequence:
```
SEQ ID NO: 1

```
ATGGGCTCATCCTGTAGCAGATCTCATTCTTTAAGTGAGGCTGAAACAACCAAAAATGCAAAATCTGCAGA

CATTGACAGGCGAATTTTGCAAGAGACAAAAGCAGAGCAACACATCCACAAGCTCTTACTTCTTGGTGCGG

GAGAATCAGGGAAGTCTACGATATTTAAACAGATTAAGCTCCTTTTCCAAACTGGCTTTGATGAGGCAGAA

CTTAGGAGCTACACATCAGTTATCCATGCAAACGTCTATCAGACAATTAAAATACTATATGAAGGAGCAAA

AGAACTCTCACAAGTGGAATCAGATTCCTCAAAGTATGTTATATCCCCAGATAACCAGGAAATTGGAGAAA

AACTATCAGATATTGATGGCAGGTTGGATTATCCACTGCTGAACAAAGAACTTGTACTCGATGTAAAAAGG

TTATGGCAAGACCCAGCCATTCAGGAAACTTACTTACGTGGAAGTATTCTGCAACTTCCTGATTGTGCACAA

TACTTCATGGAAAATTTGGATCGATTAGCTGAAGCAGGTTATGTGCCAACAAAGGAGGATGTGCTTTATGC

AAGAGTACGGACAAATGGTGTTGTACAAATACAATTTAGTCCTGTTGGAGAAAACAAAAGAGGTGGAGAG

GTATATAGGTTGTATGATGTAGGAGGCCAGAGGAATGAGAGGAGAAAGTGGATTCATCTTTTTGAAGGTG

TTAATGCGGTAATCTTTTGTGCTGCCATTAGCGAATATGATCAGATGCTATTTGAAGATGAGACAAAAACA

GAATGATGGAGACCAAGGAACTCTTTGACTGGGTTTTAAAGCAAAGATGTTTTGAGAAAACATCATTCATT

CTGTTTCTCAACAAATTTGATATATTCGAGAAGAAAATACAAAAGGTTCCTTTAAGTGTGTGCGAGTGGTTT

AAAGACTACCAGCCTATTGCACCTGGGAAACAGGAGGTTGAACATGCATATGAGTTTGTCAAGAAGAAGT

TTGAAGAGCTCTACTTCCAGAGCAGCAAGCCTGACCGTGTGGACCGCGTCTTCAAAATCTACAGAACTACG

GCCCTAGACCAGAAACTTGTAAAGAAGACATTCAAGTTGATTGATGAGAGCATGAGACGCTCCAGGGAAG

GAACTTGA
``` d1 coding region sequence (from our cDNA sequencing)

SEQ ID NO 2

```
ATGGGCTCATCCTGTAGCAGATCTCATTCTTTAAGTGAGGCTGAAACAACCAAAAATGCAAAATCTGCAGA

CATTGACAGGCGAATTTTGCAAGAGACAAAAGCAGAGCAACACATCCACAAGCTCTTACTTCTTGGTGCGG
```

```
GAGAATCAGGGAAGTCTACGATATTTAAACAGATTAAGCTCCTTTTCCAAACTGGCTTTGATGAGGCAGAA

CTTAGGAGCTACACATCAGTTATCCATGCAAACGTCTATCAGACAATTAAAATACTATATGAAGGAGCAAA

AGAACTCTCACAAGTGGAATCAGATTCCTCAAAGTATGTTATATCCCCAGATAACCAGGAAATTGGAGAAA

AACTATCAGATATTGATGGCAGGTTGGATTATCCACTGCTGAACAAAGAACTTGTACTCGATGTAAAAAGG

TTATGGCAAGACCCAGCCATTCAGGAAACTTACTTACGTGGAAGTATTCTGCAACTTCCTGATTGTGCACAA

TACTTCATGGAAAATTTGGATCGATTAGCTGAAGCAGGTTATGTGCCAACAAAGGAGGATGTGCTTTATGC

AAGAGTACGGACAAATGGTGTTGTACAAATACAATTTAGTCCTGTTGGAGAAAACAAAGAGGTGGAGAG

GTATATAGGTTGTATGATGTAGGAGGCCAGAGGAATGAGAGGAGAAAGTGGATTCATCTTTTTGAAGGTG

TTAATGCGGTAATCTTTTGTGCTGCCATTAGCGAATATGATCAGATGCTATTTGAAGATGAGACAAAAACA

GAATGATGGAGACCAAGGAACTCTTTGACTGGGTTTTAAAGCAAAGATGTTTTGAGAAAACATCATTCATT

CTGTTTCTCAACAAATTTGATATATTCGAGAAGAAAATACAAAAGGTTCCTTTAAGTGTGCGAGTGGTTTAA

AGACTACCAGCCTATTGCACCTGGGAAACAGGAGGTTGAACATGCATATGAGTTTGTCAAGAAGAAGTTTG

AAGAGCTCTACTTCCAGAGCAGCAAGCCTGACCGTGTGGACCGCGTCTTCAAAATCTACAGAACTACGGCC

CTAGACCAGAAACTTGTAAAGAAGACATTCAAGTTGATTGATGAGAGCATGAGACGCTCCAGGGAAGGAA

CTTGA

Genbank RGA1 protein sequence:
Accession: BAA07405
GI: 540533
RGA1 protein sequence:
                                                        SEQ ID NO: 3
MGSSCSRSHSLSEAETTKNAKSADIDRRILQETKAEQHIHKLLLLGAGESGKSTIFKQIKLLFQTGFDEAELRSYTSV

IHANVYQTIKILYEGAKELSQVESDSSKYVISPDNQEIGEKLSDIDGRLDYPLLNKELVLDVKRLWQDPAIQETYLR

GSILQLPDCAQYFMENLDRLAEAGYVPTKEDVLYARVRTNGVVQIQFSPVGENKRGGEVYRLYDVGGQRNERR

KWIHLFEGVNAVIFCAAISEYDQMLFEDETKNRMMETKELFDWVLKQRCFEKTSFILFLNKFDIFEKKIQKVPLSV

CEWFKDYQPIAPGKQEVEHAYEFVKKKFEELYFQSSKPDRVDRVFKIYRTTALDQKLVKKTFKLIDESMRRSREGTd1 predicted protein sequence (based on our cDNA sequencing)
                                                        SEQ ID NO: 4
MGSSCSRSHSLSEAETTKNAKSADIDRRILQETKAEQHIHKLLLLGAGESGKSTIFKQIKLLFQTGFDEAELRSYTSV

IHANVYQTIKILYEGAKELSQVESDSSKYVISPDNQEIGEKLSDIDGRLDYPLLNKELVLDVKRLWQDPAIQETYLR

GSILQLPDCAQYFMENLDRLAEAGYVPTKEDVLYARVRTNGVVQIQFSPVGENKRGGEVYRLYDVGGQRNERR

KWIHLFEGVNAVIFCAAISEYDQMLFEDETKNRMMETKELFDWVLKQRCFEKTSFILFLNKFDIFEKKIQKVPLSV

RVV-

MSU Rice Genome Annotation Project LOC_Os05g26890 (RGA1) genomic
sequence (Oryza sativa ssp japonica cv. Nipponbare - Sequence Release 7)
Sequence aligns 100% with the RGA1 sequence found within genbank clones:
Chromosome 5 clone OSJNBa0049D13 (accession AC144739)
Chromosome 5 clone OJ1005_D04 (accession AC117264)
RGA1 genomic sequence:
                                                        SEQ ID NO: 5
ATGGGCTCATCCTGTAGCAGATCTCATTCTTTAAGTGAGGCTGAAACAACCAAAAATGCAAAAGTAAGTTA

GCACTCGGACTTATTGAACAAGTAAATGCTAACTCAATTCTTGATTTGAGAGTTGCCACATTTGGTTTCTTCT

AATTCAGCTGGTAACAGTCTGCAGACATTGACAGGCGAATTTTGCAAGAGACAAAAGCAGAGCAACACAT

CCACAAGCTCTTACTTCTTGGTATTGCTAACTTTCCCAAATTTAAGTGGTCATTTTCCTTGTCACAATTATCTG

TGCTACCTTTAGTATCTATTGGTTCAGAAAATTAATTGTTTATGTTGTTCCTATTTACCTCTATAAAAAACCT

TTCTCATGTTATTTCCAAAAAAAAAGAAGATAAATAAATGTATCCTAGAAATTTTTAGTTTGAACTTGTTCTC

AATGTGGATCCATCCTTCTTTCTCTCTCAATTGCTTCTGTTTTAAGGTGCGGGAGAATCAGGGAAGTCTAC

GATATTTAAACAGGTGATGAATGTTATATTCCATGGAGAATCATAATCCGTACGCCGCTAGTTAGTCTGATG

TATTCTTACTGTTCACCTGCAGATTAAGCTCCTTTTCCAAACTGGCTTTGATGAGGCAGAACTTAGGAGCTA
```

-continued

```
CACATCAGTTATCCATGCAAACGTCTATCAGACAATTAAAGTATGCAATACTGGAAAGGGTGTGTCTTTTTT
TTCTTATTGCAAAGTGGGGATTATGTAGGAGATTCGACTAGGGATTTGTATTCTGTTCATAAGGAAATGCG
TTCATACTTTTCCTTTTTGTCGAGTAATGTGTTAAATGTTAACAGATACTATATGAAGGAGCAAAAGAACTCT
CACAAGTGGAATCAGATTCCTCAAAGTATGTTATATCCCCAGATAACCAGGTTTGTGCTTACTCTTTACTCAA
CAGTTAAAGCTAAATCTGTGCATATGAACATGTCTTGTTAAATCTGGGAATACAAACATTTTGATTTGCAAC
ATTTCTGTTGTAGTCAAGCTGCTCGGCTCTATGTTTTAACCTGTTAAGACCTTGTAGACTGTGCTCGGCTCTA
TTGTAGTCTTATATTTTACACGGTCATTCTATAATGAAAACTTGAAAAAGATATCTATTGAACCGTACAATGT
ACTGAACAAAGTAGAAAAGAACAATGAGATTTTGTAACATTTATTCTTCCTTGTTTATTTGATTGCTTCAGAC
AATTGTTGATATGCTAAAAATAACTTGGTATCAAATGTGGGTGTTATAAGATTCAATTTTTTCTCAACCAG
GTTAAAAAAAGTATACCTTTGTGCATTTACCTTGTTCCGTTGCTTTGGAACTTTAAAGGAAAACTGACTTTTC
TTAGGCATTGAAAGACAAATATCACCAGTTTCACACTGTACACCTTACCAACCAATTTTGTTTCTTAGATGTC
ATTTACTTTGTCATATCATCAGGAAATTGGAGAAAAACTATCAGATATTGATGGCAGGTTGGATTATCCACT
GCTGAACAAAGAACTTGTACTCGATGTAAAAAGGTTATGGCAAGACCCAGCCATTCAGGTGAAAACAAAT
AGCCATTCAAATCTTTTGAAGTTATATAGTTTTCCTGGCCAGGTGTGCTGAAGCAATGCTCTATACTGTAGG
AAACTTACTTACGTGGAAGTATTCTGCAACTTCCTGATTGTGCACAATACTTCATGGAAAATTTGGATCGAT
TAGCTGAAGCAGGTTATGTGCCAACAAAGGTGTGCTGTCCATGTTCATAGACAATTATTTACATATTCTCAG
ATATTTGTGCTGACACCATTTCATGTTGATTTTTAGTCTACTTAGTCAGAGGTTGTCAAATGGTTAACTATGT
GTACTGAGTCAGAGGTTGCCAAATAGTTTTAAAAGATGGGCATATGTTTATCCTTATCTTTTAAATAATATT
GGAGGCTATCCTTTAAAATTCAATATTAGGGAGGAGAAACTATTATTCTACCGTTATTACGCAGTCTACATA
ACGAAGGTAAAAAATGTCCCTGTGAAACATAGGGTGCAAAACTGCTGTGAATAAAACTCTACTTATCTAAG
CACCTTGAGCTTTTGAGTTCCCACATATTAATCTTATGACACTAGCATATATTTTTTTGTTCAGTTCCTTCAA
TAAGTTGCAAACCACAAATATGATCACTGTACCATCCACTTTTGCAACCATTTCCCGTCATTTCTTAAGCATA
GAAAATTGTTTGTCACTTGTTTAAGTCCACACTGCATCAAAATTCCAATTAACATTGTGTGCTAAGTGAA
GATATGACTCCATATTTCTGCATTTAGCAGTCTGATGGATAATTTGTGATTGTACCTTGTCTAATGGTTCGTT
TGAAAGGCTGGTAGTTGATCTTCCATACTTAAGAATGCTTGCAGTATTATAGTTGTCAATATTATGAGTCAT
TTTGCAGGAGGATGTGCTTTATGCAAGAGTACGGACAAATGGTGTTGTACAAATACAATTTAGGTAATCTG
CTGACACTATTTTTTGCACATTTTTTTGCTGGTTGCTCTACTATGTACAGAACGACAAGTTGAAGTCCTTTTTT
TCTCCCCTTTCACTTCTAAGATATGACCTGAGAGGTTCTGAATGTAGCTGTTTTAAGATGAGTTGAATCATCT
AGTTAACTGGGTTTCTTTCTGCAGTCCTGTTGGAGAAAACAAAAGAGGTGGAGAGGTATATAGGTTGTATG
ATGTAGGAGGCCAGAGGAATGAGAGGAGAAAGTGGATTCATCTTTTTGAAGGTGTTAATGCGGTAATCTT
TTGTGCTGCCATTAGCGAGTAAGTACAATTTTTTTGATTGTTGAACTTATCCTAATCTGCTAAGTTCTTCTCAT
AGGCTTCTTGTTCATTTCAGATATGATCAGATGCTATTTGAAGATGAGACAAAAAACAGAATGATGGAGAC
CAAGGAACTCTTTGACTGGGTTTTAAAGCAAAGATGTTTTGAGGTCTGCATGCATCCATCTCTGCAACCTTT
GTGCTCATGCTTTTTTTCTCATTTTGAAACTAATTACGGTGCTATATTGACCATCAGAAAACATCATTCATTCT
GTTTCTCAACAAATTTGATATATTCGAGAAGAAAATACAAAAGGTAAGGCCTGCTCTTTGTACCAATGCATA
GTTTAGTACTAAATGTTACCAACATTTATGTTTACGCTGGTTACGTAGGTTCCTTTAAGTGTGTGCGAGTGG
TTTAAAGACTACCAGCCTATTGCACCTGGGAAACAGGAGGTTGAACATGCATATGAGTGAGTGCACTACTC
GCCCTCTCAGATGAACATGGGCATTTGGCCATTTGTAATGTTGCTGCATGGTGCACTTATATGCCTTGATAA
GTTTTTCCATTCTAATGTTATATAGTATCAAACGTTCATCATTACTGTGGCTTATGGTCTGGAGTGACGTTTT
ACAGGTTTGTCAAGAAGAAGTTTGAAGAGCTCTACTTCCAGAGCAGCAAGCCTGACCGTGTGGACCGCGTC
```

TTCAAAATCTACAGAACTACGGCCCTAGACCAGAAACTTGTAAAGAAGACATTCAAGTTGATTGATGAGAG

CATGAGACGCTCCAGGGAAGGAACTTGA d1 allele sequence (from our genomic DNA sequencing)

SEQ ID NO: 6

ATGGGCTCATCCTGTAGCAGATCTCATTCTTTAAGTGAGGCTGAAACAACCAAAAATGCAAAAGTAAGTTA

GCACTCGGACTTATTGAACAAGTAAATGCTAACTCAATTCTTGATTTGAGAGTTGCCACATTTGGTTTCTTCT

AATTCAGCTGGTAACAGTCTGCAGACATTGACAGGCGAATTTTGCAAGAGACAAAAGCAGAGCAACACAT

CCACAAGCTCTTACTTCTTGGTATTGCTAACTTTCCCAAATTTAAGTGGTCATTTTCCTTGTCACAATTATCTG

TGCTACCTTTAGTATCTATTGGTTCAGAAAATTAATTGTTTATGTTGTTCCTATTTACCTCTATAAAAAACCT

TTCTCATGTTATTTCCAAAAAAAAGAAGATAAATAAATGTATCCTAGAAATTTTTAGTTTGAACTTGTTCTC

AATGTGGATCCATCCTTCTTTCTCTCTCAATTGCTTCTGTTTTAAGGTGCGGGAGAATCAGGGAAGTCTAC

GATATTTAAACAGGTGATGAATGTTATATTCCATGGAGAATCATAATCCGTACGCCGCTAGTTAGTCTGATG

TATTCTTACTGTTCACCTGCAGATTAAGCTCCTTTTCCAAACTGGCTTTGATGAGGCAGAACTTAGGAGCTA

CACATCAGTTATCCATGCAAACGTCTATCAGACAATTAAAGTATGCAATACTGGAAAGGGTGTGTCTTTTTT

TTCTTATTGCAAAGTGGGGATTATGTAGGAGATTCGACTAGGGATTTGTATTCTGTTCATAAGGAAATGCG

TTCATACTTTTCCTTTTTGTCGAGTAATGTGTTAAATGTTAACAGATACTATATGAAGGAGCAAAAGAACTCT

CACAAGTGGAATCAGATTCCTCAAAGTATGTTATATCCCCAGATAACCAGGTTTGTGCTTACTCTTTACTCAA

CAGTTAAAGCTAAATCTGTGCATATGAACATGTCTTGTTAAATCTGGGAATACAAACATTTTGATTTGCAAC

ATTTCTGTTGTAGTCAAGCTGCTCGGCTCTATGTTTTAACCTGTTAAGACCTTGTAGACTGTGCTCGGCTCTA

TTGTAGTCTTATGTTTTACACGGTCATTCTATAATGAAAACTTGAAAAAGATATCTATTGAACCGTACAATGT

ACTGAACAAAGTAGAAAAGAACAATGAGATTTTGTAACATTTATTCTTCCTTGTTTATTTGATTGCTTCAGAC

AATTGTTGATATGCTAAAAATAACTTGGTATCAAATGTGGGTGTTATAAGATTCAATTTTTTCTCAACCAG

GTTAAAAAAGTATACCTTTGTGCATTTACCTTGTTCCGTTGCTTTGGAACTTTAAAGGAAAACTGACTTTTC

TTAGGCATTGAAAGACAAATATCACCAGTTTCACACTGTACACCTTACCAACCAATTTTGTTTCTTAGATGTC

ATTTACTTTGTCATATCATCAGGAAATTGGAGAAAAACTATCAGATATTGATGGCAGGTTGGATTATCCACT

GCTGAACAAAGAACTTGTACTCGATGTAAAAAGGTTATGGCAAGACCCAGCCATTCAGGTGAAAACAAAT

AGCCATTCAAATCTTTTGAAGTTATATAGTTTTCCTGGCCAGGTGTGCTGAAGCAATGCTCTATACTGTAGG

AAACTTACTTACGTGGAAGTATTCTGCAACTTCCTGATTGTGCACAATACTTCATGGAAAATTTGGATCGAT

TAGCTGAAGCAGGTTATGTGCCAACAAAGGTGTGCTGTCCATGTTCATAGACAATTATTTACATATTCTCAG

ATATTTGTGCTGACACCATTTCATGTTGATTTTTAGTCTACTTAGTCAGAGGTTGTCAAATGGTTAACTATGT

GTACTGAGTCAGAGGTTGCCAAATAGTTTTAAAAGATGGGCATATGTTTATCCTTATCTTTTAAATAATATT

GGAGGCTATCCTTTAAAATTCAATATTAGGGAGGAGAAACTATTATTCTACCGTTATTACGCAGTCTACATA

ACGAAGGTAAAAAATGTCCCTGTGAAACATAGGGTGCAAAACTGCTGTGAATAAAACTCTACTTATCTAAG

CACCTTGAGCTTTTGAGTTCCCACATATTAATCTTATGACACTAGCATATATTTTTTTGTTCAGTTCCTTCAA

TAAGTTGCAAACCACAAATATGATCACTGTACCATCCACTTTTGCAACCATTTCCCGTCATTTCTTAAGCATA

GAAAATTGTTTGTCACTTGTTTAAGTCCACACTGCATCAAAATTCCAATTAACATTGTGTGCTAAGTGAA

GATATGACTCCATATTTCTGCATTTAGCAGTCTGATGGATAATTTGTGATTGTACCTTGTCTAATGGTTCGTT

TGAAAGGCTGGTAGTTGATCTTCCATACTTAAGAATGCTTGCAGTATTATAGTTGTCAATATTATGAGTCAT

TTTGCAGGAGGATGTGCTTTATGCAAGAGTACGGACAAATGGTGTTGTACAAATACAATTTAGGTAATCTG

CTGACACTATTTTTTGCACATTTTTTTGCTGGTTGCTCTACTATGTACAGAACGACAAGTTGAAGTCCTTTTTT

TCTCCCCTTTCACTTCTAAGATATGACCTGAGAGGTTCTGAATGTAGCTGTTTTAAGATGAGTTGAATCATCT

AGTTAACTGGGTTTCTTTCTGCAGTCCTGTTGGAGAAAACAAAAGAGGTGGAGAGGTATATAGGTTGTATG

```
ATGTAGGAGGCCAGAGGAATGAGAGGAGAAAGTGGATTCATCTTTTTGAAGGTGTTAATGCGGTAATCTT

TTGTGCTGCCATTAGCGAGTAAGTACAATTTTTTTGATTGTTGAACTTATCCTAATCTGCTAAGTTCTTCTCAT

AGGCTTCTTGTTCATTTCAGATATGATCAGATGCTATTTGAAGATGAGACAAAAAACAGAATGATGGAGAC

CAAGGAACTCTTTGACTGGTTTTAAAGCAAAGATGTTTTGAGGTCTGCATGCATCCATCTCTGCAACCTTT

GTGCTCATGCTTTTTTTCTCATTTTGAAACTAATTACGGTGCTATATTGACCATCAGAAAACATCATTCATTCT

GTTTCTCAACAAATTTGATATATTCGAGAAGAAAATACAAAAGGTAAGGCCTGCTCTTTGTACCAATGCATA

GTTTAGTACTAAATGTTACCAACATTTATGTTTACGCTGGTTACGTAGGTTCCTTTAAGTGTGCGAGTGGTTT

AAAGACTACCAGCCTATTGCACCTGGGAAACAGGAGGTTGAACATGCATATGAGTGAGTGCACTACTCGCC

CTCTCAGATGAACATGGGCATTTGGCCATTTGTAATGTTGCTGCATGGTGCACTTATATGCCTTGATAAGTT

TTTCCATTCTAATGTTATATAGTATCAAACGTTCATCATTACTGTGGCTTATGGTCTGGAGTGACGTTTTACA

GGTTTGTCAAGAAGAAGTTTGAAGAGCTCTACTTCCAGAGCAGCAAGCCTGACCGTGTGGACCGCGTCTTC

AAAATCTACAGAACTACGGCCCTAGACCAGAAACTTGTAAAGAAGACATTCAAGTTGATTGATGAGAGCAT

GAGACGCTCCAGGGAAGGAACTTGA
```
Other than the expected 2 bp deletion at 3245 and 3246, the
substitution at 1099 (located in the middle of an intron) is
the only polymorphism found between the MSU and our d1 sequences.

---

SEQUENCE LISTING

<160> NUMBER OF SEQ ID NOS: 6

<210> SEQ ID NO 1
<211> LENGTH: 1143
<212> TYPE: DNA
<213> ORGANISM: Oryza sativa

<400> SEQUENCE: 1

```
atgggctcat cctgtagcag atctcattct ttaagtgagg ctgaaacaac caaaaatgca      60
aaatctgcag acattgacag gcgaattttg caagagacaa aagcagagca acacatccac     120
aagctcttac ttcttggtgc gggagaatca gggaagtcta cgatatttaa acagattaag     180 ctcctttttcc aaactggctt tgatgaggca gaacttagga gctacacatc agttatccat     240
gcaaacgtct atcagacaat taaaatacta tatgaaggag caaagaact ctcacaagtg      300 gaatcagatt cctcaaagta tgttatatcc ccagataacc aggaaattgg agaaaaacta     360
tcagatattg atggcaggtt ggattatcca ctgctgaaca agaacttgt actcgatgta      420 aaaaggttat ggcaagaccc agccattcag gaaacttact tacgtggaag tattctgcaa     480
cttcctgatt gtgcacaata cttcatgaaa aatttggatc gattagctga agcaggttat    540
gtgccaacaa aggaggatgt gctttatgca agagtacgga caaatggtgt tgtacaaata    600
caatttagtc ctgttggaga aaacaaaaga ggtggagagg tatataggtt gtatgatgta    660
ggaggccaga ggaatgagag gagaaagtgg attcatcttt tgaaggtgt taatgcggta      720 atcttttgtg ctgccattag cgaatatgat cagatgctat ttgaagatga dacaaaaaac     780
agaatgatgg agaccaagga actctttgac tgggttttaa agcaaagatg ttttgagaaa     840
acatcattca ttctgtttct caacaaattt gatatattcg agaagaaaat acaaaaggtt     900
cctttaagtg tgtgcgagtg gtttaaagac taccagccta ttgcacctgg gaacaggag      960 gttgaacatg catatgagtt tgtcaagaag aagtttgaag agctctactt ccagagcagc    1020
aagcctgacc gtgtggaccg cgtcttcaaa atctacagaa ctacggccct agaccagaaa    1080
```

```
cttgtaaaga agacattcaa gttgattgat gagagcatga gacgctccag ggaaggaact    1140
tga                                                                 1143

<210> SEQ ID NO 2
<211> LENGTH: 1141
<212> TYPE: DNA
<213> ORGANISM: Oryza sativa

<400> SEQUENCE: 2
atgggctcat cctgtagcag atctcattct ttaagtgagg ctgaaacaac caaaaatgca     60
aaatctgcag acattgacag gcgaattttg caagagacaa aagcagagca acacatccac    120
aagctcttac ttcttggtgc gggagaatca gggaagtcta cgatatttaa acagattaag    180
ctccttttcc aaactggctt tgatgaggca gaacttagga gctacacatc agttatccat    240
gcaaacgtct atcagacaat aaaaatacta tatgaaggag caaagaaact ctcacaagtg    300
gaatcagatt cctcaaagta tgttatatcc ccagataacc aggaaattgg agaaaaacta    360
tcagatattg atggcaggtt ggattatcca ctgctgaaca agaacttgt actcgatgta     420 aaaaggttat ggcaagaccc agccattcag gaaacttact tacgtggaag tattctgcaa    480
cttcctgatt gtgcacaata cttcatgaaa aatttggatc gattagctga agcaggttat    540
gtgccaacaa aggaggatgt gctttatgca agagtacgga caaatggtgt tgtacaaata    600
caatttagtc ctgttggaga aaacaaaaga ggtggagagg tatataggtt gtatgatgta    660
ggaggccaga ggaatgagag gagaaagtgg attcatcttt ttgaaggtgt taatgcggta    720
atcttttgtg ctgccattag cgaatatgat cagatgctat ttgaagatga gacaaaaaac    780
agaatgatgg agaccaagga actctttgac tgggttttaa agcaaagatg tttgagaaa    840 acatcattca ttctgttcct caacaaattt gatatattcg agaagaaat acaaaaggtt    900 cctttaagtg tgcgagtggt ttaaagacta ccagcctatt gcacctggga acaggaggt    960 tgaacatgca tatgagtttg tcaagaagaa gtttgaagag ctctacttcc agagcagcaa   1020
gcctgaccgt gtggaccgcg tcttcaaaat ctacagaact acggccctag accagaaact   1080
tgtaaagaag acattcaagt tgattgatga gagcatgaga cgctccaggg aaggaacttg   1140
a                                                                  1141

<210> SEQ ID NO 3
<211> LENGTH: 380
<212> TYPE: PRT
<213> ORGANISM: Oryza sativa

<400> SEQUENCE: 3

Met Gly Ser Ser Cys Ser Arg Ser His Ser Leu Ser Glu Ala Glu Thr
1               5                   10                  15

Thr Lys Asn Ala Lys Ser Ala Asp Ile Asp Arg Arg Ile Leu Gln Glu
                20                  25                  30

Thr Lys Ala Glu Gln His Ile His Lys Leu Leu Leu Leu Gly Ala Gly
            35                  40                  45

Glu Ser Gly Lys Ser Thr Ile Phe Lys Gln Ile Lys Leu Leu Phe Gln
        50                  55                  60

Thr Gly Phe Asp Glu Ala Glu Leu Arg Ser Tyr Thr Ser Val Ile His
65                  70                  75                  80

Ala Asn Val Tyr Gln Thr Ile Lys Ile Leu Tyr Glu Gly Ala Lys Glu
                85                  90                  95

Leu Ser Gln Val Glu Ser Asp Ser Ser Lys Tyr Val Ile Ser Pro Asp
```

```
               100                 105                 110
Asn Gln Glu Ile Gly Glu Lys Leu Ser Asp Ile Asp Gly Arg Leu Asp
            115                 120                 125

Tyr Pro Leu Leu Asn Lys Glu Leu Val Leu Asp Val Lys Arg Leu Trp
130                 135                 140

Gln Asp Pro Ala Ile Gln Thr Tyr Leu Arg Gly Ser Ile Leu Gln
145                 150                 155                 160

Leu Pro Asp Cys Ala Gln Tyr Phe Met Glu Asn Leu Asp Arg Leu Ala
                165                 170                 175

Glu Ala Gly Tyr Val Pro Thr Lys Glu Asp Val Leu Tyr Ala Arg Val
            180                 185                 190

Arg Thr Asn Gly Val Val Gln Ile Gln Phe Ser Pro Val Gly Glu Asn
            195                 200                 205

Lys Arg Gly Gly Glu Val Tyr Arg Leu Tyr Asp Val Gly Gly Gln Arg
        210                 215                 220

Asn Glu Arg Arg Lys Trp Ile His Leu Phe Glu Gly Val Asn Ala Val
225                 230                 235                 240

Ile Phe Cys Ala Ala Ile Ser Glu Tyr Asp Gln Met Leu Phe Glu Asp
                245                 250                 255

Glu Thr Lys Asn Arg Met Met Glu Thr Lys Glu Leu Phe Asp Trp Val
            260                 265                 270

Leu Lys Gln Arg Cys Phe Glu Lys Thr Ser Phe Ile Leu Phe Leu Asn
        275                 280                 285

Lys Phe Asp Ile Phe Glu Lys Lys Ile Gln Lys Val Pro Leu Ser Val
    290                 295                 300

Cys Glu Trp Phe Lys Asp Tyr Gln Pro Ile Ala Pro Gly Lys Gln Glu
305                 310                 315                 320

Val Glu His Ala Tyr Glu Phe Val Lys Lys Phe Glu Glu Leu Tyr
                325                 330                 335

Phe Gln Ser Ser Lys Pro Asp Arg Val Asp Arg Val Phe Lys Ile Tyr
            340                 345                 350

Arg Thr Thr Ala Leu Asp Gln Lys Leu Val Lys Lys Thr Phe Lys Leu
            355                 360                 365

Ile Asp Glu Ser Met Arg Arg Ser Arg Glu Gly Thr
        370                 375                 380

<210> SEQ ID NO 4
<211> LENGTH: 307
<212> TYPE: PRT
<213> ORGANISM: Oryza sativa

<400> SEQUENCE: 4

Met Gly Ser Ser Cys Ser Arg Ser His Ser Leu Ser Glu Ala Glu Thr
1               5                   10                  15

Thr Lys Asn Ala Lys Ser Ala Asp Ile Asp Arg Arg Ile Leu Gln Glu
            20                  25                  30

Thr Lys Ala Glu Gln His Ile His Lys Leu Leu Leu Leu Gly Ala Gly
        35                  40                  45

Glu Ser Gly Lys Ser Thr Ile Phe Lys Gln Ile Lys Leu Leu Phe Gln
    50                  55                  60

Thr Gly Phe Asp Glu Ala Glu Leu Arg Ser Tyr Thr Ser Val Ile His
65                  70                  75                  80

Ala Asn Val Tyr Gln Thr Ile Lys Ile Leu Tyr Glu Gly Ala Lys Glu
                85                  90                  95
```

```
Leu Ser Gln Val Glu Ser Asp Ser Ser Lys Tyr Val Ile Ser Pro Asp
            100                 105                 110
Asn Gln Glu Ile Gly Glu Lys Leu Ser Asp Ile Asp Gly Arg Leu Asp
            115                 120                 125
Tyr Pro Leu Leu Asn Lys Glu Leu Val Leu Asp Val Lys Arg Leu Trp
    130                 135                 140
Gln Asp Pro Ala Ile Gln Glu Thr Tyr Leu Arg Gly Ser Ile Leu Gln
145                 150                 155                 160
Leu Pro Asp Cys Ala Gln Tyr Phe Met Glu Asn Leu Asp Arg Leu Ala
                165                 170                 175
Glu Ala Gly Tyr Val Pro Thr Lys Glu Asp Val Leu Tyr Ala Arg Val
            180                 185                 190
Arg Thr Asn Gly Val Val Gln Ile Gln Phe Ser Pro Val Gly Glu Asn
        195                 200                 205
Lys Arg Gly Gly Glu Val Tyr Arg Leu Tyr Asp Val Gly Gly Gln Arg
    210                 215                 220
Asn Glu Arg Arg Lys Trp Ile His Leu Phe Glu Gly Val Asn Ala Val
225                 230                 235                 240
Ile Phe Cys Ala Ala Ile Ser Glu Tyr Asp Gln Met Leu Phe Glu Asp
                245                 250                 255
Glu Thr Lys Asn Arg Met Met Glu Thr Lys Glu Leu Phe Asp Trp Val
            260                 265                 270
Leu Lys Gln Arg Cys Phe Glu Lys Thr Ser Phe Ile Leu Phe Leu Asn
        275                 280                 285
Lys Phe Asp Ile Phe Glu Lys Lys Ile Gln Lys Val Pro Leu Ser Val
    290                 295                 300
Arg Val Val
305

<210> SEQ ID NO 5
<211> LENGTH: 3640
<212> TYPE: DNA
<213> ORGANISM: Oryza sativa

<400> SEQUENCE: 5
atgggctcat cctgtagcag atctcattct ttaagtgagg ctgaaacaac caaaaatgca      60
aaagtaagtt agcactcgga cttattgaac aagtaaatgc taactcaatt cttgatttga     120
gagttgccac atttggtttc ttctaattca gctggtaaca gtctgcagac attgacaggc     180
gaattttgca agagacaaaa gcagagcaac acatccacaa gctcttactt cttggtattg     240
ctaactttcc caaatttaag tggtcatttt ccttgtcaca attatctgtg ctacctttag     300
tatctattgg ttcagaaaat taattgttta tgttgttcct atttacctct ataaaaaaac     360
ctttctcatg ttatttccaa aaaaaaagaa gataaataaa tgtatcctag aaattttag      420 tttgaacttg ttctcaatgt ggatccatcc ttctttctct ctctcaattg cttctgtttt     480
aaggtgcggg agaatcaggg aagtctacga tatttaaaca ggtgatgaat gttatattcc     540
atggagaatc ataatccgta cgccgctagt tagtctgatg tattcttact gttcacctgc     600
agattaagct ccttttccaa actggctttg atgaggcaga acttaggagc tacacatcag     660
ttatccatgc aaacgtctat cagacaatta agtatgcaa tactggaaag ggtgtgtctt      720
ttttttctta ttgcaaagtg gggattatgt aggagattcg actagggatt tgtattctgt     780
tcataaggaa atgcgttcat actttttcctt tttgtcgagt aatgtgttaa atgttaacag     840
atactatatg aaggagcaaa agaactctca caagtggaat cagattcctc aaagtatgtt     900
```

```
atatccccag ataaccaggt ttgtgcttac tctttactca acagttaaag ctaaatctgt    960
gcatatgaac atgtcttgtt aaatctggga atacaaacat tttgatttgc aacatttctg   1020
ttgtagtcaa gctgctcggc tctatgtttt aacctgttaa gaccttgtag actgtgctcg   1080
gctctattgt agtcttatat tttacacggt cattctataa tgaaaacttg aaaaagatat   1140
ctattgaacc gtacaatgta ctgaacaaag tagaaaagaa caatgagatt ttgtaacatt   1200
tattcttcct tgtttatttg attgcttcag acaattgttg atatgctaaa ataacttgg    1260
tatcaaatgt gggtgttata agattcaatt ttttttctcaa ccaggttaaa aaagtatac   1320
ctttgtgcat ttaccttgtt ccgttgcttt ggaactttaa aggaaaactg acttttctta   1380
ggcattgaaa gacaaatatc accagtttca cactgtacac cttaccaacc aattttgttt   1440
cttagatgtc atttactttg tcatatcatc aggaaattgg agaaaaacta tcagatattg   1500
atggcaggtt ggattatcca ctgctgaaca agaacttgt actcgatgta aaaaggttat    1560
ggcaagaccc agccattcag gtgaaaacaa atagccattc aaatcttttg aagttatata   1620
gttttcctgg ccaggtgtgc tgaagcaatg ctctatactg taggaaactt acttacgtgg   1680
aagtattctg caacttcctg attgtgcaca atacttcatg gaaaatttgg atcgattagc   1740
tgaagcaggt tatgtgccaa caaggtgtg ctgtccatgt tcatagacaa ttatttacat    1800
attctcagat atttgtgctg acaccatttc atgttgattt ttagtctact tagtcagagg   1860
ttgtcaaatg gttaactatg tgtactgagt cagaggttgc caaatagttt taaaagatgg   1920
gcatatgttt atccttatct tttaaataat attggaggct atcctttaaa attcaatatt   1980
agggaggaga aactattatt ctaccgttat tacgcagtct acataacgaa ggtaaaaaat   2040
gtccctgtga aacatagggt gcaaaactgc tgtgaataaa actctactta tctaagcacc   2100
ttgagctttt gagttcccac atattaatct tatgacacta gcatatattt ttttttgttca   2160
gttccttcaa taagttgcaa accacaaata tgatcactgt accatccact tttgcaacca   2220
tttcccgtca tttcttaagc atagaaaatt gtttgtcact tgtttaagtc cacactgcat   2280
caaaattcca attaacattg tgtgtgctaa gtgaagatat gactccatat ttctgcattt   2340
agcagtctga tggataattt gtgattgtac cttgtctaat ggttcgtttg aaaggctggt   2400
agttgatctt ccatacttaa gaatgcttgc agtattatag ttgtcaatat tatgagtcat   2460
tttgcaggag gatgtgcttt atgcaagagt acggacaaat ggtgttgtac aaatacaatt   2520
taggtaatct gctgacacta tttttttgcac atttttttgc tggttgctct actatgtaca   2580
gaacgacaag ttgaagtcct ttttttctcc cctttcactt ctaagatatg acctgagagg   2640
ttctgaatgt agctgtttta agatgagttg aatcatctag ttaactgggt ttctttctgc   2700
agtcctgttg gagaaaacaa aagaggtgga gaggtatata ggttgtatga tgtaggaggc   2760
cagaggaatg agaggagaaa gtggattcat ctttttgaag gtgttaatgc ggtaatcttt   2820
tgtgctgcca ttagcgagta agtacaattt ttttgattgt tgaacttatc ctaatctgct   2880
aagttcttct cataggcttc ttgttcattt cagatatgat cagatgctat ttgaagatga   2940
gacaaaaaac agaatgatgg agaccaagga actctttgac tgggttttaa agcaaagatg   3000
ttttgaggtc tgcatgcatc catctctgca acctttgtgc tcatgctttt tttctcattt   3060
tgaaactaat tacggtgcta tattgaccat cagaaaacat cattcattct gtttctcaac   3120
aaatttgata tattcgagaa gaaaatacaa aaggtaaggc ctgctctttg taccaatgca   3180
tagtttagta ctaaatgtta ccaacattta tgtttacgct ggttacgtag gttcctttaa   3240
```

```
gtgtgtgcga gtggtttaaa gactaccagc ctattgcacc tgggaaacag gaggttgaac   3300
atgcatatga gtgagtgcac tactcgccct ctcagatgaa catgggcatt tggccatttg   3360
taatgttgct gcatggtgca cttatatgcc ttgataagtt tttccattct aatgttatat   3420
agtatcaaac gttcatcatt actgtggctt atggtctgga gtgacgtttt acaggtttgt   3480
caagaagaag tttgaagagc tctacttcca gagcagcaag cctgaccgtg tggaccgcgt   3540
cttcaaaatc tacagaacta cggccctaga ccagaaactt gtaaagaaga cattcaagtt   3600
gattgatgag agcatgagac gctccaggga aggaacttga                         3640

<210> SEQ ID NO 6
<211> LENGTH: 3638
<212> TYPE: DNA
<213> ORGANISM: Oryza sativa

<400> SEQUENCE: 6
atgggctcat cctgtagcag atctcattct ttaagtgagg ctgaaacaac caaaaatgca     60
aaagtaagtt agcactcgga cttattgaac aagtaaatgc taactcaatt cttgatttga    120
gagttgccac atttggtttc ttctaattca gctggtaaca gtctgcagac attgacaggc    180
gaattttgca agagacaaaa gcagagcaac acatccacaa gctcttactt cttggtattg    240
ctaactttcc caaatttaag tggtcatttt ccttgtcaca attatctgtg ctacctttag    300
tatctattgg ttcagaaaat taattgttta tgttgttcct atttacctct ataaaaaaac    360 cttttctcatg ttatttccaa aaaaaaagaa gataaataaa tgtatcctag aaatttttag    420
tttgaacttg ttctcaatgt ggatccatcc ttctttctct ctctcaattg cttctgtttt    480
aaggtgcggg agaatcaggg aagtctacga tatttaaaca ggtgatgaat gttatattcc    540
atggagaatc ataatccgta cgccgctagt tagtctgatg tattcttact gttcacctgc    600
agattaagct ccttttccaa actggctttg atgaggcaga acttaggagc tacacatcag    660
ttatccatgc aaacgtctat cagacaatta agtatgcaa tactggaaag ggtgtgtctt     720 tttttttctta ttgcaaagtg gggattatgt aggagattcg actagggatt tgtattctgt    780
tcataaggaa atgcgttcat acttttcctt tttgtcgagt aatgtgttaa atgttaacag    840
atactatatg aaggagcaaa agaactctca caagtggaat cagattcctc aaagtatgtt    900
atatccccag ataaccaggt ttgtgcttac tctttactca acagttaaag ctaaatctgt    960
gcatatgaac atgtcttgtt aaatctggga atacaaacat tttgatttgc aacatttctg   1020
ttgtagtcaa gctgctcggc tctatgtttt aacctgttaa gaccttgtag actgtgctcg   1080
gctctattgt agtcttatgt tttacacggt cattctataa tgaaaacttg aaaaagatat   1140
ctattgaacc gtacaatgta ctgaacaaag tagaaaagaa caatgagatt ttgtaacatt   1200
tattcttcct tgtttatttg attgcttcag acaattgttg atatgctaaa aataacttgg   1260
tatcaaatgt gggtgttata agattcaatt ttttctcaa ccaggttaaa aaagtatac    1320 ctttgtgcat ttaccttgtt ccgttgcttt ggaactttaa aggaaaactg acttttctta   1380
ggcattgaaa gacaaatatc accagtttca cactgtacac cttaccaacc aattttgttt   1440
cttagatgtc atttactttg tcatatcatc aggaaattgg agaaaaacta tcagatattg   1500
atggcaggtt ggattatcca ctgctgaaca aagaacttgt actcgatgta aaaaggttat   1560
ggcaagaccc agccattcag gtgaaaacaa atagccattc aaatctttg aagttatata   1620
```

```
gttttcctgg ccaggtgtgc tgaagcaatg ctctatactg taggaaactt acttacgtgg    1680
aagtattctg caacttcctg attgtgcaca atacttcatg gaaaatttgg atcgattagc    1740
tgaagcaggt tatgtgccaa caaaggtgtg ctgtccatgt tcatagacaa ttatttacat    1800
attctcagat atttgtgctg acaccatttc atgttgattt ttagtctact tagtcagagg    1860
ttgtcaaatg gttaactatg tgtactgagt cagaggttgc caaatagttt taaaagatgg    1920
gcatatgttt atccttatct tttaaataat attggaggct atcctttaaa attcaatatt    1980
agggaggaga aactattatt ctaccgttat tacgcagtct acataacgaa ggtaaaaaat    2040
gtccctgtga aacatagggt gcaaaactgc tgtgaataaa actctactta tctaagcacc    2100
ttgagctttt gagttccacc atattaatct tatgacacta gcatatattt tttttgttca    2160
gttccttcaa taagttgcaa accacaaata tgatcactgt accatccact tttgcaacca    2220
tttcccgtca tttcttaagc atagaaaatt gtttgtcact tgtttaagtc cacactgcat    2280
caaaattcca attaacattg tgtgtgctaa gtgaagatat gactccatat ttctgcattt    2340
agcagtctga tggataattt gtgattgtac cttgtctaat ggttcgtttg aaaggctggt    2400
agttgatctt ccatacttaa gaatgcttgc agtattatag ttgtcaatat tatgagtcat    2460
tttgcaggag gatgtgcttt atgcaagagt acggacaaat ggtgttgtac aaatacaatt    2520
taggtaatct gctgacacta tttttttgcac atttttttgc tggttgctct actatgtaca    2580
gaacgacaag ttgaagtcct ttttttctcc cctttcactt ctaagatatg acctgagagg    2640
ttctgaatgt agctgtttta agatgagttg aatcatctag ttaactgggt ttctttctgc    2700
agtcctgttg gagaaaacaa aagaggtgga gaggtatata ggttgtatga tgtaggaggc    2760
cagaggaatg agaggagaaa gtggattcat cttttttgaag gtgttaatgc ggtaatcttt    2820
tgtgctgcca ttagcgagta agtacaattt ttttgattgt tgaacttatc ctaatctgct    2880
aagttcttct cataggcttc ttgttcattt cagatatgat cagatgctat ttgaagatga    2940
gacaaaaaac agaatgatgg agaccaagga actctttgac tgggttttaa agcaaagatg    3000
ttttgaggtc tgcatgcatc catctctgca acctttgtgc tcatgctttt tttctcattt    3060
tgaaactaat tacggtgcta tattgaccat cagaaaacat cattcattct gtttctcaac    3120
aaatttgata tattcgagaa gaaaatacaa aaggtaaggc ctgctctttg taccaatgca    3180
tagtttagta ctaaatgtta ccaacattta tgtttacgct ggttacgtag gttcctttaa    3240
gtgtgcgagt ggtttaaaga ctaccagcct attgcacctg ggaaacagga ggttgaacat    3300
gcatatgagt gagtgcacta ctcgccctct cagatgaaca tgggcatttg gccatttgta    3360
atgttgctgc atggtgcact tatatgcctt gataagtttt tccattctaa tgttatatag    3420
tatcaaacgt tcatcattac tgtggcttat ggtctggagt gacgttttac aggtttgtca    3480
agaagaagtt tgaagagctc tacttccaga gcagcaagcc tgaccgtgtg gaccgcgtct    3540
tcaaaatcta cagaactacg gccctagacc agaaacttgt aaagaagaca ttcaagttga    3600
ttgatgagag catgagacgc tccagggaag gaacttga                            3638
```

What is claimed is:

1. A genetically modified plant with improved seed production in drought conditions and/or improved survival at high planting densities compared to the seed production in drought conditions and/or survival at high planting densities, respectively, of a corresponding plant with no such modification, said modification comprising a heterologous polynucleotide that reduces G-protein activity in said plant, wherein said heterologous polynucleotide comprises a nucleotide selected from the group consisting of:

(a) a nucleotide sequence which encodes the amino acid sequence of SEQ ID NO: 4; or (b) a nucleotide sequence corresponding to SEQ ID NO:5, wherein said sequence comprises a deletion of nucleotides 3241 and 3242 compared to SEQ ID NO:5;

said modified plant having reduced G-protein activity when compared to a non-modified plant in the same conditions, said G-protein comprising G-protein alpha subunit (Gα).

2. The modified plant of claim 1 wherein said G-protein protein activity is created by introducing an inhibition construct to said plant or an ancestor thereof.

3. Seed of the plant of claim 1. wherein said seed comprises the heterologous polynucleotide that reduces G-protein activity in a plant produced from said seed.

4. The plant of claim 1 wherein said plant is a maize, cotton, soybean, wheat, barley, rice, rye, oat or sorghum plant.

5. The plant of claim 1 wherein said plant is a rice plant.

6. The plant of claim 1 wherein said modification is a loss of function modification.

7. The plant of claim 1 wherein said plant includes a heterologous construct that inhibits expression of a G-protein alpha subunit.

8. The plant of claim 1 wherein said plant includes a G-protein alpha subunit expression cassette that is an inhibitory cassette.

9. The plant of claim 1 wherein said G-protein alpha subunit sequence is SEQ ID NO: 1 or 5.

\* \* \* \* \*